US011007245B2

(12) United States Patent
Farrow et al.

(10) Patent No.: US 11,007,245 B2
(45) Date of Patent: May 18, 2021

(54) BOTULINUM NEUROTOXIN-SPECIFIC CAPTURE AGENTS, COMPOSITIONS, AND METHODS OF USING AND MAKING

(71) Applicants: California Institute of Technology, Pasadena, CA (US); Indi Molecular, Inc., Culver City, CA (US)

(72) Inventors: Blake Farrow, Pasadena, CA (US); James R. Heath, South Pasadena, CA (US); Heather Dawn Agnew, Culver City, CA (US)

(73) Assignees: INDI MOLECULAR, INC., Culver City, CA (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 78 days.

(21) Appl. No.: 15/420,596

(22) Filed: Jan. 31, 2017

(65) Prior Publication Data

US 2017/0218021 A1    Aug. 3, 2017

Related U.S. Application Data

(62) Division of application No. 15/072,039, filed on Mar. 16, 2016, now Pat. No. 9,913,875.

(60) Provisional application No. 62/133,891, filed on Mar. 16, 2015.

(51) Int. Cl.
| | |
|---|---|
| C07B 59/00 | (2006.01) |
| A61K 38/00 | (2006.01) |
| A61K 38/12 | (2006.01) |
| A61K 38/06 | (2006.01) |
| C07K 7/52 | (2006.01) |
| C07K 5/083 | (2006.01) |
| A61K 38/08 | (2019.01) |
| C07K 7/06 | (2006.01) |
| G01N 33/531 | (2006.01) |
| A61K 47/60 | (2017.01) |
| C07K 7/08 | (2006.01) |
| G16B 5/00 | (2019.01) |

(52) U.S. Cl.
CPC .......... *A61K 38/005* (2013.01); *A61K 38/06* (2013.01); *A61K 38/08* (2013.01); *A61K 38/12* (2013.01); *A61K 47/60* (2017.08); *C07B 59/008* (2013.01); *C07K 5/0808* (2013.01); *C07K 7/06* (2013.01); *C07K 7/08* (2013.01); *C07K 7/52* (2013.01); *G01N 33/531* (2013.01); *A61K 38/00* (2013.01); *C07B 2200/05* (2013.01); *C07K 2319/01* (2013.01); *C07K 2319/70* (2013.01); *G01N 2333/33* (2013.01); *G16B 5/00* (2019.02); *Y02A 50/30* (2018.01)

(58) Field of Classification Search
None
See application file for complete search history.

(56) References Cited

U.S. PATENT DOCUMENTS

| | | | |
|---|---|---|---|
| 4,899,755 | A | 2/1990 | Lauffer et al. |
| 5,474,756 | A | 12/1995 | Tweedle et al. |
| 5,846,519 | A | 12/1998 | Tweedle et al. |
| 6,143,274 | A | 11/2000 | Tweedle et al. |
| 6,667,158 | B1 | 12/2003 | Bavari et al. |
| 2010/0009896 | A1 | 1/2010 | Agnew et al. |

FOREIGN PATENT DOCUMENTS

| | | | | |
|---|---|---|---|---|
| EP | 2719706 A1 | * | 4/2014 | ............ C07K 16/32 |
| WO | 1986006605 A1 | | 11/1986 | |
| WO | 1991003200 A1 | | 3/1991 | |
| WO | 1995028179 A1 | | 10/1995 | |
| WO | 1995028967 A1 | | 11/1995 | |
| WO | 1996023526 A2 | | 8/1996 | |
| WO | 1997036619 A2 | | 10/1997 | |
| WO | 1998018496 A2 | | 5/1998 | |
| WO | 1998018497 A2 | | 5/1998 | |
| WO | 1998046612 A1 | | 10/1998 | |
| WO | 1999017809 A2 | | 4/1999 | |
| WO | 2009155420 A1 | | 12/2009 | |
| WO | 2012106671 A1 | | 8/2012 | |
| WO | 2013009869 A2 | | 1/2013 | |
| WO | WO-2013009869 A2 | * | 1/2013 | ......... A61K 49/0043 |
| WO | 2013033561 A1 | | 3/2013 | |
| WO | 2014074907 A1 | | 5/2014 | |

OTHER PUBLICATIONS

Alexander et al. (Aug. 1998) "Intracranial black-blood MR angiography with high-resolution 3D fast spin echo," Magn. Reson. Med. 40(2)298-310.
Altschul et al. (1997) "Gapped BLAST and PSI-BLAST: a new generation of protein database search programs," Nucleic Acids Res. 25(17):3389-402.
Bremer et al. (Aug. 1, 2014) "Benzoquinones as Inhibitors of Botulinum Neurotoxin Serotype A," Bioorg Med Chem. 22(15):3971-3981.
Bundgaard (1985) "Design of Prodrugs," Elsevier, Amsterdam. pp. 7-9, 21-24.
CLaverie et al. (1993) "Information enhancement methods for large scale sequence analysis," Computers & Chemistry. 17(2):191-201.
Coppock et al. (May 22, 2014) "Peptide-based protein capture agents with high affinity, selectivity, and stability as antibody replacements in biodetection assays," Proc. of SPIE. Smart Biomedical and Physiological Sensor Technology XI. 9107:910711. pp. 1-6.

(Continued)

*Primary Examiner* — Jeanette M Lieb
(74) *Attorney, Agent, or Firm* — Pabst Patent Group LLP

(57) ABSTRACT

The present application provides stable peptide-based Botulinum neurotoxin (BoNT) serotype A capture agents and methods of use as detection and diagnosis agents and in the treatment of diseases and disorders. The application further provides methods of manufacturing BoNT serotype A capture agents using iterative on-bead in situ click chemistry.

17 Claims, 32 Drawing Sheets

Specification includes a Sequence Listing.

(56) References Cited

OTHER PUBLICATIONS

Edelman et al. (1990) "Extracranial carotid arteries: evaluation with 'black blood' MR angiography," Radiology. 177(1):45-50.

Farrow et al. (Apr. 29, 2015) "Epitope Targeting of Tertiary Protein Structure Enables Target-Guided Synthesis of a Potent In-Cell Inhibitor of Botulinum Neurotoxin," Angew. Chem., Int. Ed. 54(24):7114-7119.

Goodrich et al. (1996) "A Quantitative Study of Ramped Radio Frequency, Magnetization Transfer, and Slab Thickness in Three-Dimensional Time-of-Flight Magnetic Resonance Angiography in a Patient Population," Invest. Radial. 31(6):323-32.

International Search Report with Written Opinion corresponding to International Patent Application No. PCT/US2016/022693, dated May 27, 2016.

Ma et al. (2006) "A cyclic peptide-polymer probe for the detection of Clostridium botulinum neurotoxin serotype A," Toxicon. 47(8):901-908.

Meyers et al. (1988) "Optimal alignments in linear space," Computer Applications in the Biosciences. 4(1):11-17.

Non-Final Rejection corresponding to U.S. Appl. No. 15/072,039, dated May 11, 2017.

The University of Arizona (2000) "Antibody Structure," The Biology Project. [Available online at http://www.biology.arizona.edu/immunology/tutorials/antibody/structure.html, accessed on May 5, 2017].

Wootton et al. (1993) "Statistics of local complexity in amino acid sequences and sequence databases," Computers & Chemistry. 17(2):149-163.

Zuniga et al. (2010) "Iterative structure-based peptide-like inhibitor design against the botulinum neurotoxin serotype A," PloS one. 5(6):e11378.

* cited by examiner

| $X_1$ | $X_2$ | $X_3$ | $X_4$ | $X_5$ | $X_6$ | $X_7$ |
|---|---|---|---|---|---|---|
| Pra | - | N | W | W | K | I |
| Pra | - | N | Y | Q | W | T |
| Pra | - | N | Y | Y | R | A |
| Pra | - | N | Y | R | W | L |
| Pra | - | Y | H | Q | R | L |
| Pra | - | Y | Q | R | W | ? |
| Pra | - | N | R | Y | P | Y |
| Pra | - | H | N | R | W | ? |
| Pra | - | G | P | R | ? | W |

SEQUENCE LISTING

<160> NUMBER OF SEQ ID NOS: 12

<210> SEQ ID NO 1
<211> LENGTH: 1209
<212> TYPE: PRT
<213> ORGANISM: Clostridium botulinum

<400> SEQUENCE: 1

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Glu Glu Phe
        115                 120                 125

Asn Thr Asn Ile Ala Ser Val Thr Val Asn Lys Ile Ser Asn Pro Gly
    130                 135                 140

Glu Val Glu Arg Lys Lys Gly Ile Phe Ala Asn Ile Ile Phe Gly Pro
145                 150                 155                 160

Gly Pro Val Asn Glu Asn Glu Thr Ile Asp Ile Gly Ile Gln Asn His
                165                 170                 175

Phe Ala Ser Arg Glu Gly Phe Gly Gly Ile Met Gln Met Lys Phe Cys
            180                 185                 190

Pro Glu Tyr Val Ser Val Phe Asn Asn Val Gln Glu Asn Lys Gly Ala
        195                 200                 205

Ser Ile Phe Asn Arg Arg Gly Tyr Phe Ser Asp Pro Ala Ile Met His
    210                 215                 220

Glu Ile His Val His Gly Tyr Gly Ile Lys Val Asp Asp Pro Ile Val
225                 230                 235                 240

Pro Asn Glu Lys Lys Phe Phe Met Gln Ser Thr Asp Ala Ile Gln Ala
                245                 250                 255

Glu Glu Tyr Thr Phe Gly Gly Gln Asp Pro Ser Ile Ile Thr Pro Ser
            260                 265                 270

Thr Asp Lys Ser Ile Tyr Asp Lys Val Gln Asn Phe Arg Gly Ile Val
        275                 280                 285

Asp Arg Asn Lys Val Val Cys Ile Ser Asp Pro Asn Ile Asn Ile Asn
    290                 295                 300

Ile Tyr Lys Asn Lys Phe Lys Asp Lys Tyr Lys Phe Val Glu Asp Ser
305                 310                 315                 320

Glu Gly Lys Tyr Ser Ile Asp Val Glu Ser Phe Asp Lys Tyr Lys Ser
                325                 330                 335

Met Phe Gly Phe Thr Glu Thr Asn Ile Ala Glu Asn Tyr Lys Ile Lys
            340                 345                 350

Thr Arg Ala Ser Tyr Phe Ser Asp Ser Pro Val Lys Ile Lys Asn
        355                 360                 365

-continued

```
Asp Asn Glu Ile Tyr Thr Ile Glu Glu Gly Phe Asn Ile Ser Asp Lys
    370                 375                 380
Asp Met Glu Lys Glu Tyr Arg Gly Gln Asn Lys Ala Ile Asn Lys Gln
385                 390                 395                 400
Ala Tyr Glu Glu Ile Ser Lys Glu His Ala Val Tyr Lys Ile Gln Met
                405                 410                 415
Cys Lys Ser Val Lys Ala Pro Gly Ile Cys Ile Asp Val Asp Asn Glu
            420                 425                 430
Asp Phe Phe Ile Ala Asp Lys Asn Ser Phe Ser Asp Ser Lys Asn
        435                 440                 445
Glu Arg Ile Glu Tyr Asn Thr Lys Asn Ile Tyr Ile Glu Asn Tyr Phe
    450                 455                 460
Ser Ile Asn Glu Ile Asp Thr Asp Ile Ser Gly Ile Glu Pro Ser Glu
465                 470                 475                 480
Asn Thr Glu Ser Thr Asp Phe Asn Val Asp Val Pro Val Tyr Glu Lys
                485                 490                 495
Gln Pro Ala Ile Lys Lys Ile Phe Thr Asp Glu Asn Thr Ile Phe Gln
            500                 505                 510
Tyr Tyr Ser Gln Thr Phe Pro Asp Ile Arg Asp Ile Ser Thr Ser Ser
        515                 520                 525
Phe Asp Asp Ala Phe Ser Asn Lys Val Tyr Ser Phe Ser Met Asp
    530                 535                 540
Tyr Ile Lys Thr Ala Asn Lys Val Val Glu Ala Gly Phe Ala Gly Trp
545                 550                 555                 560
Val Lys Gln Ile Ile Asp Asp Phe Val Ile Glu Ala Asn Lys Ser Ser
                565                 570                 575
Thr Met Asp Lys Ile Ala Asp Ile Ser Ile Val Pro Tyr Ile Gly Ala
            580                 585                 590
Asn Val Gly Asn Glu Thr Ala Lys Gly Asn Phe Glu Asn Ala Phe Glu
        595                 600                 605
Ile Ala Gly Ala Ser Ile Leu Leu Glu Phe Ile Pro Glu Leu Leu Ile
    610                 615                 620
Pro Val Val Gly Ala Phe Glu Ser Tyr Ile Asp Asn Lys Asn Lys Ile
625                 630                 635                 640
Ile Lys Thr Ile Asp Asn Ala Thr Lys Arg Val Glu Lys Trp Ile Asp
                645                 650                 655
Met Tyr Gly Ile Val Ala Gln Trp Ser Thr Val Asn Thr Gln Phe Tyr
            660                 665                 670
Thr Ile Lys Glu Gly Met Tyr Lys Ala Asn Tyr Gln Ala Gln Ala Glu
        675                 680                 685
Glu Ile Ile Lys Tyr Lys Tyr Asn Ile Tyr Ser Glu Lys Glu Lys Asn
    690                 695                 700
Ile Asn Ile Asp Phe Asn Asp Ile Asn Ser Lys Asn Glu Gly Ile Asn
705                 710                 715                 720
Gln Ala Ile Asp Asn Ile Asn Asn Phe Ile Asn Glu Cys Ser Val Ser
                725                 730                 735
Tyr Met Lys Lys Met Ile Pro Ala Ile Glu Lys Asp Phe Asp Asn Ala
            740                 745                 750
Lys Lys Asn Asn Tyr Ile Asp Glu Asn Lys Tyr Ile Gly Ser Val Glu
        755                 760                 765
Glu Glu Lys Ser Lys Val Asp Lys Phe Phe Lys Thr Ile Ile Pro Phe
    770                 775                 780
Asp Ser Met Tyr Thr Asn Asn Thr Ile Ile Glu Met Val Asn Lys Tyr
```

```
                785                 790                 795                 800
Asn Ser Glu Ile Asn Asn Ile Ile Asn Arg Tyr Arg Asp Asn Asn Ile
                    805                 810                 815
Asp Ser Ser Gly Tyr Gly Ala Lys Val Glu Val Tyr Asn Gly Val Glu
                    820                 825                 830
Asn Asp Lys Asn Gln Phe Lys Thr Ser Ser Ala Asn Ser Lys Ile Lys
                    835                 840                 845
Val Thr Gln Asn Gln Asn Ile Thr Phe Asn Ser Met Phe Asp Phe Ser
850                 855                 860
Val Ser Phe Trp Ile Arg Ile Pro Lys Tyr Lys Asn Asp Gly Ile Gln
865                 870                 875                 880
Asn Tyr Ile His Asn Glu Tyr Thr Ile Ile Asn Cys Met Lys Asn Asn
                    885                 890                 895
Ser Gly Trp Lys Ile Ser Ile Arg Gly Asn Arg Ile Ile Trp Thr Thr
                    900                 905                 910
Asp Ile Asn Gly Lys Thr Lys Ser Val Phe Phe Glu Tyr Ser Ile Arg
                    915                 920                 925
Glu Asp Ile Ser Asp Tyr Ile Asn Arg Trp Phe Phe Val Thr Ile Thr
930                 935                 940
Asn Asn Asp Asn Ala Lys Ile Tyr Ile Asn Gly Lys Glu Ser Asn Ile
945                 950                 955                 960
Asp Ile Arg Asp Ile Arg Glu Val Ile Val Asn Gly Glu Ile Ile Phe
                    965                 970                 975
Lys Asp Gly Glu Ile Asp Arg Thr Gln Phe Ile Trp Met Lys Tyr Phe
                    980                 985                 990
Ser Ile Phe Asn Thr Glu Ser Gln Ser Asn Val Lys Glu Ile Tyr Lys
                    995                 1000                1005
Ile Gln Ser Tyr Ser Lys Tyr Lys Asp Phe Trp Gly Asn Pro Met
            1010                1015                1020
Tyr Asn Lys Glu Tyr Tyr Met Phe Asn Ala Gly Asn Lys Asn Ser
            1025                1030                1035
Tyr Ile Lys Val Lys Asp Ser Ser Val Gly Glu Ile Thr Arg Ser
            1040                1045                1050
Lys Tyr Asn Gln Asn Ser Asn Tyr Ile Asn Tyr Arg Asn Tyr Ile
            1055                1060                1065
Gly Glu Lys Phe Ile Ile Arg Arg Lys Ser Ser Gln Ser Ile
            1070                1075                1080
Ser Asp Asp Ile Val Arg Lys Glu Asp Tyr Ile Tyr Asp Phe Phe
            1085                1090                1095
Asn Ser Asn Arg Glu Trp Arg Val Tyr Ala Tyr Lys Asn Phe Lys
            1100                1105                1110
Gly Gln Glu Glu Lys Phe Ala Asn Ile Tyr Asp Ser Asn Glu Phe
            1115                1120                1125
Tyr Lys Thr Ile Gln Ile Lys Glu Tyr Asp Glu Gln Pro Thr Tyr
            1130                1135                1140
Ser Cys Gln Phe Lys Lys Asp Glu Glu Ser Thr Asp Glu Ile Gly
            1145                1150                1155
Ile Gly Ile His Asn Phe Tyr Glu Ser Gly Ile Phe Lys Asp Tyr
            1160                1165                1170
Lys Asp Tyr Phe Cys Ile Ser Lys Trp Tyr Lys Glu Val Lys Lys
            1175                1180                1185
Lys Pro Tyr Ser Ser Asn Gly Cys Asn Trp Gln Phe Ile Pro Lys
            1190                1195                1200
```

Asp Glu Gly Trp Thr Glu
    1205

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Diaminobutyric Acid
<220> FEATURE:
<221> NAME/KEY: MISC_FEATURE
<222> LOCATION: (1)..(1)
<223> OTHER INFORMATION: Dinitrophenol is attached to Diaminobutyric
      Acid
<220> FEATURE:
<221> NAME/KEY: MISC_FEATURE
<222> LOCATION: (3)..(3)
<223> OTHER INFORMATION: Azide is attached to lysine
<220> FEATURE:
<221> NAME/KEY: VARIANT
<222> LOCATION: (5)..(5)
<223> OTHER INFORMATION: Diaminobutyric Acid
<220> FEATURE:
<221> NAME/KEY: VARIANT
<222> LOCATION: (6)..(6)
<223> OTHER INFORMATION: Propargylglycine
<220> FEATURE:
<221> NAME/KEY: MISC_FEATURE
<222> LOCATION: (7)..(7)
<223> OTHER INFORMATION: One or more undefined chemical moieties may be
      attached to leucine

<400> SEQUENCE: 2

Xaa Arg Lys Thr Xaa Xaa Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Diaminobutyric Acid
<220> FEATURE:
<221> NAME/KEY: MISC_FEATURE
<222> LOCATION: (1)..(1)
<223> OTHER INFORMATION: Dinitrophenol is attached to Diaminobutyric
      Acid
<220> FEATURE:
<221> NAME/KEY: VARIANT
<222> LOCATION: (5)..(5)
<223> OTHER INFORMATION: Diaminobutyric Acid
<220> FEATURE:
<221> NAME/KEY: MISC_FEATURE
<222> LOCATION: (5)..(5)
<223> OTHER INFORMATION: Undefined chemical moiety may be attached to
      Diaminobutyric Acid
<220> FEATURE:
<221> NAME/KEY: VARIANT
<222> LOCATION: (6)..(6)
<223> OTHER INFORMATION: Propargylglycine
<220> FEATURE:
<221> NAME/KEY: MISC_FEATURE
<222> LOCATION: (8)..(8)
<223> OTHER INFORMATION: One or more chemical moieties may be attached
      to lysine

<400> SEQUENCE: 3

```
Xaa Arg Lys Thr Xaa Xaa Leu Lys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Diaminobutyric Acid
<220> FEATURE:
<221> NAME/KEY: MISC_FEATURE
<222> LOCATION: (1)..(1)
<223> OTHER INFORMATION: Dinitrophenol is attached to Diaminobutyric
      Acid
<220> FEATURE:
<221> NAME/KEY: MISC_FEATURE
<222> LOCATION: (3)..(3)
<223> OTHER INFORMATION: Azide is attached to lysine
<220> FEATURE:
<221> NAME/KEY: VARIANT
<222> LOCATION: (5)..(5)
<223> OTHER INFORMATION: Diaminobutyric Acid
<220> FEATURE:
<221> NAME/KEY: VARIANT
<222> LOCATION: (6)..(6)
<223> OTHER INFORMATION: Propargylglycine
<220> FEATURE:
<221> NAME/KEY: MISC_FEATURE
<222> LOCATION: (8)..(8)
<223> OTHER INFORMATION: Biotin is attached to lysine
<220> FEATURE:
<221> NAME/KEY: MISC_FEATURE
<222> LOCATION: (9)..(9)
<223> OTHER INFORMATION: Azide is attached to lysine

<400> SEQUENCE: 4

Xaa Arg Lys Thr Xaa Xaa Leu Lys Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Propargylglycine
<220> FEATURE:
<221> NAME/KEY: MISC_FEATURE
<222> LOCATION: (1)..(1)
<223> OTHER INFORMATION: Undefined chemical moiety may be attached to
      propargylglycine
<220> FEATURE:
<221> NAME/KEY: MISC_FEATURE
<222> LOCATION: (7)..(7)
<223> OTHER INFORMATION: Azide is atached to lysine

<400> SEQUENCE: 5

Xaa Asn Tyr Arg Trp Leu Lys
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: VARIANT
<222> LOCATION: (1)..(1)
<223> OTHER INFORMATION: Propargylglycine
<220> FEATURE:
<221> NAME/KEY: VARIANT
<222> LOCATION: (2)..(2)
<223> OTHER INFORMATION: Propargylglycine
<220> FEATURE:
<221> NAME/KEY: MISC_FEATURE
<222> LOCATION: (3)..(7)
<223> OTHER INFORMATION: Any Xaa is any natural amino acid
<220> FEATURE:
<221> NAME/KEY: MISC_FEATURE
<222> LOCATION: (8)..(8)
<223> OTHER INFORMATION: Azide is attached to lysine

<400> SEQUENCE: 6

Xaa Xaa Xaa Xaa Xaa Xaa Xaa Lys Thr Gly
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Propargylglycine
<220> FEATURE:
<221> NAME/KEY: MISC_FEATURE
<222> LOCATION: (2)..(6)
<223> OTHER INFORMATION: Any Xaa is any natural amino acid
<220> FEATURE:
<221> NAME/KEY: VARIANT
<222> LOCATION: (7)..(7)
<223> OTHER INFORMATION: Propargylglycine
<220> FEATURE:
<221> NAME/KEY: MISC_FEATURE
<222> LOCATION: (13)..(13)
<223> OTHER INFORMATION: Azide is attached to lysine

<400> SEQUENCE: 7

Xaa Xaa Xaa Xaa Xaa Xaa Xaa Asn Tyr Arg Trp Leu Lys Thr Gly
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Diaminobutyric Acid
<220> FEATURE:
<221> NAME/KEY: MISC_FEATURE
<222> LOCATION: (1)..(1)
<223> OTHER INFORMATION: Dinitrophenol is attached to Diaminobutyric
      Acid
<220> FEATURE:
<221> NAME/KEY: VARIANT
<222> LOCATION: (5)..(5)
<223> OTHER INFORMATION: Diaminobutyric Acid
<220> FEATURE:
<221> NAME/KEY: MISC_FEATURE
<222> LOCATION: (7)..(7)
<223> OTHER INFORMATION: One or more chemical moieties may be attached
      to leucine

<400> SEQUENCE: 8
```

```
Xaa Arg Trp Thr Xaa Met Leu
1               5

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Azide is attached to lysine
<220> FEATURE:
<221> NAME/KEY: MISC_FEATURE
<222> LOCATION: (13)..(13)
<223> OTHER INFORMATION: One or more chemical moieties may be attached
      to asparagine

<400> SEQUENCE: 9

Lys Ser Phe Gly His Glu Val Leu Asn Leu Thr Arg Asn
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Azide is attached to lysine
<220> FEATURE:
<221> NAME/KEY: MISC_FEATURE
<222> LOCATION: (13)..(13)
<223> OTHER INFORMATION: One or more undefined chemical moieties may be
      attached to histidine

<400> SEQUENCE: 10

Lys Asn Gly Thr Leu Phe Asn Leu Ser Glu Val Arg His
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Azide and one ore more additional undefined
      chemical moieties may be attached to lysine

<400> SEQUENCE: 11

Lys Pro Leu Ile Tyr Leu Arg Leu Leu Arg Gly Gln Phe
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Gln Arg Ala Thr Lys Met Leu
1               5
```

BOTULINUM NEUROTOXIN-SPECIFIC CAPTURE AGENTS, COMPOSITIONS, AND METHODS OF USING AND MAKING

RELATED APPLICATIONS

This application claims priority from U.S. Provisional Patent Application No. 62/133,891, filed on Mar. 16, 2015, which is incorporated herein by reference in its entirety.

STATEMENT OF GOVERNMENT INTEREST

This invention was made with government support under Grant No. W911 NF-09-D-0001 awarded by the U.S. Army. The government has certain rights in the invention.

BACKGROUND

Botulinum neurotoxin (BoNT) serotype A is the most lethal known toxin. BoNT is produced by some species of the bacterial genus Clostridium and is a chemodenervating zinc-dependent protease that prevents the $Ca^{2+}$-triggered release of acetylcholine in neuromuscular junctions by cleaving one of the three SNARE proteins required for synaptic vesicle formation and release. BoNT/A intoxication proceeds with selective binding to neuronal receptors, cell entry through receptor-mediated endocytosis, endosome escape via pH-induced translocation, and finally, cleavage of its SNAP-25 substrate in the cytosol. BoNT/A is comprised of a receptor-binding heavy chain and disulfide-linked catalytic light chain (LC). This disulfide bond must be intact for the toxin to poison neurons, but must be broken for the LC to act catalytically in the cytosol. A subdomain (the 'belt') structurally occludes the intact holotoxin active site so that drug-induced inhibition only occurs after belt release, which is promoted by the reduction of the disulfide link by the cytosolic environment. The rapid sequestration of BoNT toxins into motor neurons limits current antibody based therapies, while molecular inhibitors cannot access the occluded active site of circulating BoNT. BoNT is a potentially deadly bioweapon, but is also a therapeutic and cosmetic agent, with an accompanying risk of accidental overdosing. Potent and effective inhibitors are needed.

SUMMARY

The present disclosure relates to chemically synthesized capture agents (called protein-catalyzed capture agents, or PCC Agents) that are designed to bind botulinum neurotoxin (BoNT) serotype A, methods for making said capture agents, methods for using said capture agents to inhibit BoNT serotype A and treat or prevent botulism or botulin toxin poisoning.

In one aspect, provided herein is a stable, synthetic capture agent that specifically binds to BoNT serotype A, wherein the botulinum neurotoxin serotype A protein comprises a heavy chain and a light chain, wherein the light chain comprises an enzymatic active site, wherein the capture agent comprises an anchor ligand and a secondary ligand and wherein the ligands selectively bind BoNT serotype A.

In another aspect, provided herein is a composition comprising one or more synthetic capture agents of the invention that specifically binds BoNT serotype A.

In another aspect, provided herein is a method for detecting BoNT serotype A in a biological sample, comprising the step of treating the biological sample with one or more capture agents of the invention.

In another aspect, provided herein is method of inhibiting SNAP-25 cleavage mediated by botulinum neurotoxin serotype A protein in one or more neurons in a subject in need thereof, the method comprising administering to the neurons an effective amount of one or more capture agents of the invention.

In another aspect, provided herein is method treating botulism in a subject in need thereof, the method comprising administering a therapeutically effective amount of one or more capture agents of the invention.

Anchor Ligand

In one embodiment of the capture agent, the anchor ligand specifically binds to the enzymatic active site of BoNT serotype A. In another embodiment, the anchor ligand comprises a cyclic peptide of the formula of Dab(DNP)-R-Lys(N3)-T-Dab-Pra-L-NH— (SEQ ID NO: 2), wherein the N3 and Pra moieties together represent a Tz4 or a Tz5 linkage. In another embodiment, the anchor ligand comprises a molecule of formula Inh-1

Inh-1 wherein $R^1$ is absent or is a linker to the secondary ligand.

Secondary Ligand

In one embodiment, the secondary ligand specifically binds to a site on the botulinum neurotoxin serotype A protein that is 3-10 angstroms away from the enzymatic active site of the botulinum neurotoxin serotype A protein. In another embodiment, the secondary ligand specifically binds the botulinum neurotoxin serotype A light chain. In another embodiment, the secondary ligand specifically binds an occluded conformation of the botulinum neurotoxin serotype A holotoxin. In another embodiment, the secondary ligand specifically binds residues 166-179 of the botulinum neurotoxin serotype A light chain. In another embodiment, the secondary ligand comprises a cyclic peptide of the formula of -Pra-NYRWL-Lys(N3) (SEQ ID NO:5), wherein the N3 and Pra moieties together represent a Tz4 or a Tz5 linkage. In another embodiment, the secondary ligand comprises a molecule of formula L2 wherein R² is absent or is a linker to the anchor ligand.

In another embodiment, the secondary ligand is selected from an epitope made up of residues 166-179 of the BoNT light chain screened against a 1.1 million element library of macrocyclic 5-mer peptides. In another embodiment, the library is anti-screened against a scrambled version of the same epitope.

Linkers

In one embodiment, the capture agents described herein comprise a linker. In certain embodiments, the linker is a tripeptide. For example, the linker can comprise the amino acid sequence of Gly-Aib-Leu or Leu-Aib-Gly. In other embodiments, the linker comprises PEG₄.

In certain embodiments, the anchor ligand and/or the secondary ligand are linked to the linker via a 1,4-substituted-1,2,3-triazole residue (Tz4) or via a 1,5-substituted-1,2,3-triazole residue (Tz5). In other embodiments, the anchor ligand is linked to the linker via a Tz4.

In certain embodiments, the linker is 3-10 angstroms in length. In other embodiments, the linker is 5-8 angstroms in length. In other embodiments, the linker has a length between 100 and 110% percent of the distance between the anchor ligand and the secondary ligand.

Triazole Linkage

In one embodiment of the capture agent, the anchor ligand and secondary ligand are linked together via a 1,4-substituted-1,2,3-triazole residue (Tz4). In another embodiment, the secondary ligand and the tertiary ligand are linked together via a 1,4-substituted-1,2,3-triazole residue (Tz4). In yet another embodiment, the tertiary ligand and the quarternary ligand are linked together via a 1,4-substituted-1,2,3-triazole residue (Tz4). In yet another embodiment, the anchor ligand and secondary ligand are linked together via a 1,4-substituted-1,2,3-triazole residue, and the secondary ligand and the tertiary ligand are linked together via a 1,4-substituted-1,2,3-triazole residue. In yet another embodiment, the anchor ligand and secondary ligand are linked together via a 1,4-substituted-1,2,3-triazole residue, the secondary ligand and the tertiary ligand are linked together via a 1,4-substituted-1,2,3-triazole residue and the tertiary ligand and the quarternary ligand are linked together via a 1,4-substituted-1,2,3-triazole residue.

Biligands

In one embodiment, a capture agent of the invention is a biligand, comprising an anchor ligand and a secondary ligand. Non-limiting examples of secondary ligands are also disclosed in FIG. 16.

In certain embodiments, the capture agent comprises a molecule of formula Inh-2 wherein R³ is hydrogen, a capping group (e.g., an amide), or comprises a label or a spontaneously translocating peptide.

Properties

In certain embodiments, the BoNT serotype A capture agents provided herein are stable across a wide range of temperatures, pH's, storage times, storage conditions, and reaction conditions, and in certain embodiments the capture agents are more stable than a comparable antibody or biologic. In certain embodiments, the capture agents are stable in storage as a lyophilized powder. In certain embodiment, the capture agents are stable in storage at a temperature of about −80° C. to about 60° C. In certain embodiments, the capture agents are stable at room temperature. In certain embodiments, the capture agents are stable in human serum for at least 24 hours. In certain embodiments, the capture agents are stable at a pH in the range of about 3 to about 12. In certain embodiments, the capture agents are stable as a powder for two months at a temperature of about 60° C.

Detectable Labels

In some embodiments, the capture agent is labeled with a label selected from the group consisting of biotin, copper-DOTA, biotin-PEG3, aminooxyacetate, $^{19}$FB, $^{18}$FB, FITC-PEG3, fluorescein and fluorescein derivatives (e.g., 5-carboxy fluorescein). In other embodiments, the capture agent is labeled with the detectable moiety consisting of $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In other embodiments, the label is a fluorescent label. In a particular embodiment, the detectable label is $^{18}$F.

Translocating Peptides

In some embodiments, the capture agent comprises a translocating peptide. These translocating peptides allow the capture agents to enter eukaryotic cells. In certain embodiments, these eukaryotic cells are mammalian cells. In specific embodiments, these mammalian cells are human cells. In certain embodiments, the translocating peptide is a spontaneously translocating peptide. Optionally, the spontaneously translocating peptide comprises the amino acid sequence of pliylrllrGqf (SEQ ID NO:11).

Other translocating peptides that can be used include HIV-TAT, penetratin, SynB1, SynB2, PTD-4, PTD-5, FHV Coar (35-49), BMV Gag (7-25), HTLV-II Rex (4-16), D-Tat, R9-Tat, transportan, MAP, SBP, FBP, MPG, Pep-1, Pep-2, polyarginines, or polylysines. Any sequence at least 90% identical to any of the translocating peptides or fragments thereof may be used.

Methods and Uses

Provided herein is a method of inhibiting SNAP-25 cleavage mediated by botulinum neurotoxin serotype A protein in one or more neurons in a subject in need thereof comprising administering to the neurons an effective amount of the capture agent as provided herein. In certain embodiments, inhibition of BoNT serotype A activity results in treatment or prevention of botulism or botulin toxin poisoning.

Synthesis of Capture Agents

Provided herein are methods for making (i.e., synthesizing) the BoNT serotype A capture agents of the invention. In one embodiment, the method comprises the steps of:
 a. identifying an anchor ligand and a secondary ligand that bind to the same target peptide at distinct epitopes;
 b. identifying the binding sites of the anchor ligand and the secondary ligand on the target peptide;
 c. calculating the distance between the binding site of the anchor ligand and the secondary ligand; and
 d. selecting a linker to connect the anchor ligand to the secondary ligand, thereby generating a capture agent, wherein the dissociation constant of the capture agent for binding to the target protein is lower than the dissociation constant of either the anchor ligand or the secondary ligand for binding to the target protein.

In one embodiment, the method further comprises the step of:
 e. synthesizing the capture agent comprising the anchor ligand and secondary ligand of step (a) and the linker of step (d).

In one embodiment, the linking of the anchor ligand and the secondary ligand is performed using a linker. In certain embodiments, the linker has a length that is between 100 and 110% percent of the distance between the anchor ligand and the secondary ligand when both ligands are bound to the botulinum neurotoxin serotype A protein.

Also provided herein are methods for making (i.e., synthesizing) the BoNT serotype A capture agents of the invention. In one embodiment, the method comprises the steps of:
 a. selecting an anchor ligand that specifically binds to the enzymatic active site of the botulinum neurotoxin serotype A protein;
 b. selecting a secondary ligand that specifically binds at a distinct epitope from the anchor ligand within 5-10 angstroms on the botulinum neurotoxin serotype A protein; and
 c. linking the anchor ligand and secondary ligand together, wherein, the secondary ligand must bind to an epitope so that it specifically binds to an occluded conformation of the botulinum neurotoxin serotype A holotoxin, thereby synthesizing the capture agent for inhibiting SNAP-25 cleavage mediated by botulinum neurotoxin serotype A protein in one or more neurons.

BRIEF DESCRIPTION OF DRAWINGS

FIG. 3A) Inhibition curve (left axis) and fluorescence polarization binding curve (right axis) of Inh-1. An IC$_{50}$ value of inhibition of 70±10 nM and a k$_D$ value of 68±29 nM were obtained by Hill curve fitting. FIG. 3B) Inhibition curve (left axis) and fluorescence polarization binding curve (right axis) of compound L2. No inhibition was observed, and a $k_D$ value of 78±8 nM was determined. FIG. 3C) Inhibition curves comparing Inh-1 (pink) to Inh-2 (red). $IC_{50}$ values of 60±11 nM and 165±15 pM, respectively, were observed. FIG. 3D) Single-point ELISA binding data of compounds to the reduced (available active site) and intact (occluded by belt) BoNT/A holotoxins. Error bars indicate standard deviation of replicates.

FIG. 4A) Top shows western blots of neuron lysates for B-tubulin (control) and SNAP (cleaved and uncleaved). The cleaved SNAP product appears as a longer running band below the intact SNAP in the western blot. Assays were performed with various concentrations of compounds Inh-1 and Inh-2 along with a known endocytosis-inhibiting polyclonal sheep anti-BoNT heavy-chain antibody. The plot below shows the percentage of intact SNAP as a function of ligand concentration. This percentage was calculated as the ratio of the integrated intact band intensity to the total integrated intensity of the bands. FIG. 4B) Top shows representative epifluorescence images of live neurons after FM1-43 synaptic vesicle stain loading and after depolarization with and without prior BoNT intoxication; scale bars: 40 μm. The plot below shows the average integrated synaptic vesicle stain intensity on a per-cell basis for all conditions with 1 μM added compound where relevant. Error bars indicate standard deviation of replicates.

FIG. 5A) Experimental timeline of 55 U bolus toxin exposure (i) and 24 our incubation with 2 U toxin (ii). The protection effect was evaluated by pre-incubation of the toxin with 1 μm inhibiting anti-BoNT pAb or Inh-2-STP, and the rescue effect was evaluated 1, 3, and 12 hours after exposure to toxin by lysing cells and quantitating SNAP cleavage by western blot analysis and densitometry. In all cases, the cells were lysed 24 hours after toxin exposure. FIG. 5B) Representative western blots of neuron lysates for B-tubulin (control) and SNAP (cleaved and uncleaved) after the rescue experiments shown in FIG. 5A. The cleaved SNAP product appears as a longer running band below the intact SNAP in the western blot. FIG. 5C) Percentage of intact SNAP as a function of exposure time before treatment. The percentage was calculated as the ratio of the integrated intact band intensity to the total integrated intensity of the bands. Error bars indicate standard deviation of replicates.

FIG. 12: Preliminary ELISA curves of inhibitory ligands. Candidate substrate mimic ligand BoNT LC binding was evaluated by sandwich ELISA and compared to the literature inhibitor (blue).

FIGS. 13A-13C: Representative in vitro BoNT LC activity assays. Typical time-fluorescence traces showing cleavage of SNAP-25 FRET substrate with various concentrations of BoNT LC, with the initial 2000 seconds zoomed in and fit to a Vmax initial slope to gather kinetics data. Vmax observed as a function of BoNT LC concentration shown.

FIG. 16: List of hit sequences of epitope targeted screen. Beads were sequenced by Edman degredation and colors indicate similar sidechain residues to better illustrate homology, dashes indicate amino acids involved in the click cycle.

FIG. 19: Single point sandwich ELISA comparing BoNT ligand variants. Peptides were immobilized on neutravidin resin at 1 μM concentration and blocked in 3% BSA for 3 hours. Bound ligands were incubated with 50 nM BoNT LC-GST conjugate or buffer blank for three hours. ELISAs were probed with anti-GST-HRP mAb as detailed in protocols and developed.

FIG. 22A) FM1-43 labeled control cells, no depolarization FIG. 22B) FM1-43 labeled BoNT intoxicated cells, after depolarization, FIG. 22C) FM1-43 labeled control cells, after depolarization, FIG. 22D) Unlabeled BoNT intoxicated cells. All labeling and depolarization is described in the SI procedures.

DETAILED DESCRIPTION

Figure 1:
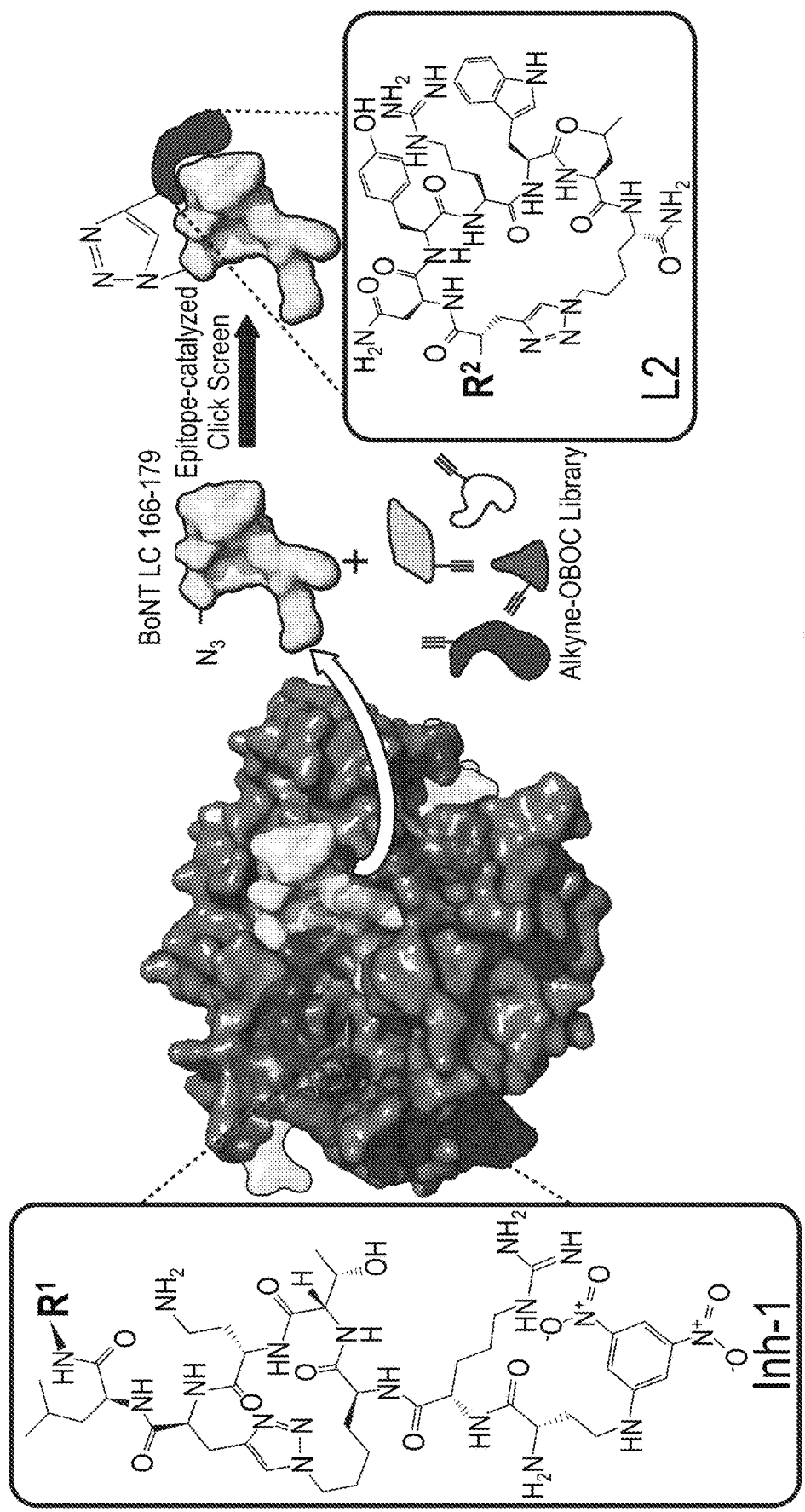
FIG. 1: The development of a biligand inhibitor of BoNT/A. Inh-1 (orange, Dab(DNP)-R-Lys(N3)-T-Dab-Pra-L-R1 (SEQ ID NO:2)) is based on the natural peptide substrate for BoNT LC and previous structural studies of peptidomimetic substrate mimics. Epitope targeting was used to screen for a secondary ligand targeted to a nearby unstructured epitope (BoNT LC 166-179, green) exposed in the presence of the holotoxin's occluding belt (red). The ligand selected (L2, red, R2-Pra-NYRWL-Lys(N3) (SEQ ID NO:5)) was selected from a 1 100000 member macrocyclic peptide library.

Provided herein is a capture agent that specifically binds botulinum neurotoxin serotype A and inhibits its ability to cleave SNAP-25 in neurons. In one embodiment, the capture agent comprises at least two ligands. One of the two ligands specifically binds to the enzymatic active site located on the light chain of botulinum neurotoxin serotype A and the other ligand binds at distinct location on the botulinum neurotoxin serotype A protein. According to certain embodiments, the second binding site is within 3-10 angstroms from the first binding site. According to other embodiments, the ligand that binds to the second binding site is able to specifically bind the occluded conformation of the botulinum neurotoxin serotype A holotoxin. According to other embodiments, the second binding site is also on the light chain of botulinum neurotoxin serotype A.

According to certain embodiments, an anchor ligand is chosen that binds to the enzyme active site of botulinum neurotoxin serotype A protein. This enzyme active site is located on the light chain of the protein. According to certain embodiments, the anchor ligand inhibits the activity of the enzyme active site of botulinum neurotoxin serotype A protein. According to some embodiments, the anchor protein inhibits the activity of botulinum neurotoxin serotype A protein at an inhibition constant of between 10 and 1000 nM. According to other embodiments, the inhibition constant is between 10 and 200 nM. According to other embodiments, the inhibition constant is between 30 and 100 nM, 50 and 80 nM or 65 and 75 nM. According to certain embodiments, the inhibition constant is about 70 nM.

According to certain embodiments, a secondary ligand is chosen that also binds to the botulinum neurotoxin serotype A protein. In certain embodiments, the secondary ligand is able to bind the occluded conformation of the botulinum neurotoxin serotype A holotoxin. In certain embodiments, the secondary ligand binds to an epitope close enough to the binding site of the anchor ligand that a linker can be provided to connect the two ligands. In certain embodiments, the secondary ligand is chosen as a result of screening a combinatorial library.

According to certain embodiments, a linker is chosen that connects the two ligands. In certain embodiments, the linker is rigid and similar in length to the distance between at least one portion of the two ligands when they are bound to the botulinum neurotoxin serotype A protein. In certain embodiments, the portions of the ligands are the N- or C-termini. In one embodiment, the linker is about the length equal to the root mean square average separation of the two binding sites. In certain embodiments, the linker is chosen as a result of screening a combinatorial linker library.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, the terms "capture agent of the invention", and "capture agents of the invention" refer to synthetic protein-catalyzed capture agents which bind botulinum neurotoxin serotype A, as described herein.

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Aminocarbonyl" refers to a radical of the formula —C(=O)NR$_a$R$_a$, where each R$_a$ is independently H, alkyl or a linker moiety.

"α-amino carbonyl" refers to a radical of the formula —C(=O)CR$_b$(NR$_a$R$_a$)—, where each R$_a$ is independently H, alkyl or a linker moiety and R$_b$ is H or alkyl. In some embodiments, an alpha amino carbonyl is part of a cyclic moiety (e.g., peptide) where the carbonyl is within the ring and the amino (NR$^a$R$^a$) is exocyclic. For example, in certain embodiments and alpha aminocarbonyl is useful for Edman degradation of cyclic peptides.

"α-amido carbonyl" refers to a radical of the formula —C(=O)CR$_b$(N(C=O)R$_a$R$_a$)—, where each R$_a$ is independently H, alkyl or a linker moiety and R$_b$ is H or alkyl. In some embodiments, an alpha amido carbonyl is part of a cyclic moiety (e.g., peptide) where the carbonyl is within the ring and the amido (N(C=O)R$^a$R$^a$) is exocyclic.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2,2,1]heptanyl, and the like. Unless otherwise stated specifically in the specification, a cycloalkyl group may be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —RbRf where Rb is an alkylene chain as defined above and Rf is a heteroaryl radical as defined above. Unless stated otherwise specifically in the specification, a heteroarylalkyl group may be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O) NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with C(=O)R$_g$, C(=O)OR$_g$, C(=O)NR$_g$R$_h$, CH$_2$SO$_2$R$_g$, CH$_2$SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable peptides of structure (I) or (I') being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively.

These radiolabelled compounds could be useful to help determine or measure the effectiveness of the compounds, by characterizing, for example, the site or mode of action, or binding affinity to pharmacologically important site of action. Certain isotopically-labelled peptides of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled peptides can generally be prepared by conventional techniques known to those skilled in the art or by processes analogous to those described in the Preparations and Examples as set out below using an appropriate isotopically-labeled reagent in place of the non-labeled reagent previously employed.

"Mammal" includes humans and both domestic animals such as laboratory animals and household pets (e.g., cats, dogs, swine, cattle, sheep, goats, horses, rabbits), and non-domestic animals such as wildlife and the like.

"Mutant" or "Variant" refers to a protein that has high homology to a wild-type amino acid sequence, but not 100% identity with the wild-type amino acid sequence. High homology associated with mutants or variants is higher than 95, 96, 97, 98 or 99% but less than 100%. In certain embodiments, a mutant or variant differs from a wild-type sequence at 1, 2, 3, 4, 5, 6, 7, 8, 9 or 10 amino acids.

In certain embodiments, the sequence of BoNT serotype A refers to the amino acid sequence (SEQ ID NO:1) shown below.

```
   1 mpvtinnfny ndpidnnnii mmeppfargt gryykafkit driwiipery tfgykpedfn
  61 kssgifnrdv ceyydpdyln tndkkniflq tmiklfnrik skplgeklle miingipylg
 121 drrvpleefn tniasvtvnk lisnpgever kkgifanlii fgpgpvlnen etidigiqnh
 181 fasregfggi mqmkfcpeyv svfnnvqenk gasifnrrgy fsdpalilmh elihvlhgly
 241 gikvddlpiv pnekkffmqs tdaiqaeely tfggqdpsii tpstdksiyd kvlqnfrgiv
 301 drlnkvlvci sdpnininiy knkfkdkykf vedsegkysi dvesfdklyk slmfgftetn
 361 iaenykiktr asyfsdslpp vkiknlldne iytieegfni sdkdmekeyr gqnkainkqa
 421 yeeiskehla vykiqmcksv kapgicidvd nedlffiadk nsfsddlskn erieyntkni
 481 yienyfsine lildtdlisg ielpsentes ltdfnvdvpv yekqpaikki ftdentifqy
 541 lysqtfpldi rdisltssfd dallfsnkvy sffsmdyikt ankvveaglf agwvkqiidd
 601 fvieanksst mdkiadisli vpyiglalnv gnetakgnfe nafeiagasi llefipelli
 661 pvvgaflles yidnknkiik tidnaltkrv ekwidmygli vaqwlstvnt qfytikegmy
 721 kalnyqaqal eeiikykyni ysekeklnin idfndinskl neginqaidn innfinecsv
 781 sylmkkmipl aieklldfdn alkknllnyi denklyligs veeekskvdk ffktiipfdl
 841 smytnntili emvnkynsei lnniilnlry rdnnlidssg ygakvevyng velndknqfk
 901 ltssanskik vtqnqnitfn smfldfsvsf wiripkyknd giqnyihney tiincmknns
 961 gwkisirgnr iiwtltding ktksvffeys iredisdyin rwffvtitnn ldnakiying
1021 klesnidird irevivngei ifkldgeidr tqfiwmkyfs ifntelsqsn vkeiykiqsy
1081 skylkdfwgn plmynkeyym fnagnknsyi klvkdssvge iltrskynqn snyinyrnly
1141 igekfiirrk sssqsisddi vrkedyiyld ffnsnrewrv yayknfkgqe eklflaniyd
1201 snefyktiqi keydeqptys cqllfkkdee stdeigligi hnfyesgilf kdykdyfcis
1261 kwylkevkkk pyssnlgcnw qfipkdegwt e
```

The above sequence is the full sequence of the holoenzyme. This holoenzyme is cleaved into light chain and heavy chain peptides. In certain embodiments, the light chain is made up of amino acids 1-448 above and the heavy chain is made of amino acids 449-1291.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, The invention disclosed herein is also meant to encompass the in vivo metabolic products of the disclosed peptides. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds (peptides) of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G".

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

The term "capture agent" as used herein refers to a composition that comprises one or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent (PCC).

The term "epitope" as used herein refers to a distinct molecular surface of a protein (e.g., the BoNT serotype A protein). Typically, the epitope is a polypeptide and it can act on its own as a finite sequence of 10-40 amino acids. In the present disclosure, at least two epitopes are bound. The first epitope involves the enzymatic active site of the epitope BoNT serotype A. In certain embodiments, the anchor ligand binds this enzymatic active site with high affinity so that its activity is inhibited. In certain embodiments, the second epitope is a portion of the BoNT serotype A holotoxin that is solvent exposed in the occluded conformation. For example, this epitope can be amino acids 166-179 of the BoNT serotype A (light chain).

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods. Non-natural amino acids can include 2-aminoisobutyric acid (Aib) and propargylglycine (Pra).

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-5}$M, such as approximately less than $10^{-6}$ M, $10^{-7}$ M, $10^{-8}$ M, $10^{-9}$ M or $10^{-10}$ M or even lower.

The term "$K_D$" as used herein refers to the dissociation equilibrium constant of a particular capture agent-antigen interaction. Typically, the capture agents of the invention bind to BoNT serotype A protein with a dissociation equilibrium constant ($K_D$) of less than approximately $10^{-6}$ M, $10^{-7}$ M, $10^{-8}$ M, $10^{-9}$ M or $10^{-10}$ M or even lower, for example, as determined using surface plasmon resonance (SPR) technology in a Biacore instrument using the capture agent as the ligand and the BoNT serotype A protein as the analyte, and bind to a BoNT serotype A protein with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the capture agent, so that when the $K_D$ of the capture agent is very low (that is, the capture agent is highly specific), then the amount with which the affinity for the antigen is lower than the affinity for a non-specific antigen may be at least 10,000 fold.

The term "$k_d$" (sec$^{-1}$) as used herein refers to the dissociation rate constant of a particular capture agent-antigen interaction. Said value is also referred to as the $k_{off}$ value.

The term "$k_a$" (M$^{-1}$×sec$^{-1}$) as used herein refers to the association rate constant of a particular capture agent-antigen interaction.

The term "KD" (M) as used herein refers to the dissociation equilibrium constant of a particular capture agent-antigen interaction.

The term "$K_A$" (M$^{-1}$) as used herein refers to the association equilibrium constant of a particular capture agent-antigen interaction and is obtained by dividing the $k_a$ by the $k_d$.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event. In specific embodiments, the condition is botulism or botulin toxin poisoning.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a capture agent may vary according to factors such as the disease state, age, sex, and weight of the individual, and the ability of the capture agent to elicit a desired response in the individual.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab, Fv, Fab', F(ab')$_2$ and the like. A monoclonal antibody is an antibody that specifically binds to and is thereby defined as complementary to a single particular spatial and polar organization of another biomolecule which is termed an "epitope." In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "stable" as used herein with regard to a capture agent protein catalyzed capture agent or pharmaceutical formulation thereof refers to the agent or formulation retaining structural and functional integrity for a sufficient period of time to be utilized in the methods described herein.

The term "synthetic" as used herein with regard to a protein catalyzed capture agent or capture agent refers to the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

As used herein in the context of cyclic peptides, it will be understood that N3 and Pra moieties together represent a Tz4 or a Tz5 linkage.

Development of BoNT Serotype A Capture Agents

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: USSN 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand may be identified by screening the protein against a large (>10$^6$ element) one-bead-one-compound (OBOC) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described, most require detailed structural information on the target to guide the screening strategy, and most (such as the original in situ click approach), are optimized for low-diversity small molecule libraries.

The present embodiment further generalizes the in situ click application to find a linker that links two ligands to a single protein. This method uses cooperative binding to make a capture ligand with higher affinity than either of its component ligands.

BoNT Serotype A Capture Agents

In one aspect, provided herein is a stable, synthetic capture agent that specifically binds BoNT Serotype A, wherein the capture agent comprises a designed anchor ligand, a designed secondary ligand, optionally a designed tertiary ligand, and optionally a designed quarternary ligand, and wherein the ligands selectively bind BoNT Serotype A. In one embodiment, the capture agent specifically binds the enzymatic active site of BoNT Serotype A. In another embodiment, the capture agent specifically binds a site of BoNT Serotype A that is accessible on the occluded conformation of the holotoxin.

In certain embodiments, provided herein are biligand BoNT Serotype A capture agents comprising two target-binding moieties. The first target-binding moiety is referred to as an anchor ligand, and the second is referred to as a secondary ligand. Also provided are triligand and tetraligand capture agents, wherein the third target-binding moiety is referred to as a tertiary ligand, and the fourth target-binding moiety is referred to as a quarternary ligand.

In certain embodiments, a target-binding moiety comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azioalkyl, substituted and unsubstituted polyethyleneglycolyl, and substituted and unsubstituted 1,2,3-triazole.

In certain embodiments, the anchor ligand and secondary ligand are linked to one another via a covalent linkage to form a capture agent biligand. In certain of these embodiments, the anchor ligand and secondary ligand are linked to one another via an amide bond or a 1,4-disubstituted-1,2,3-triazole linkage as shown below:

1,4-disubstituted-1,2,3-triazole linkage.

In those embodiments where the anchor and secondary ligands are linked to one another via a 1,4-disubstituted-1,2,3-triazole linkage, the 1,4-disubstituted-1,2,3-riazole linkage may be formed by Cu-Catalyzed Azide/Alkyne Cycloaddition (CuAAC).

In certain embodiments, the anchor and secondary ligands are linked to one another by a Tz4 linkage having the following structure:

In certain embodiments, the anchor and secondary ligands are linked to one another by a Tz5 linkage having the following structure:

[Structure drawing of an amino acid derivative with a triazole-linked side chain]

In certain embodiments, the tertiary and/or quarternary ligand is linked to the capture agent biligand by a covalent linkage, preferably via the secondary ligand in the biligand. In certain of these embodiments, the tertiary ligand and the biligand and/or the quarternary ligand and the tertiary ligand are linked to one another by a Tz4 linkage.

In those embodiments wherein one or more of the anchor, secondary, tertiary, and/or quarternary ligands are linked to one another via amide bonds, the amide bond may be formed by coupling a carboxylic acid group and an amine group in the presence of a coupling agent (e.g., O-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In certain embodiments, the capture agents provided herein are stable across a range of reaction conditions and/or storage times. A capture agent that is "stable" as used herein maintains the ability to specifically bind to a target protein. In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the capture agents provided herein are stable at a pH range from about 3.0 to about 8.0. In certain embodiments, the range is about 4.0 to about 7.0. In certain embodiments, the range is about 7.0 to about 8.0.

In certain embodiments, the capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein. In certain embodiments, the capture agents are stable as a powder for two months at a temperature of about 60° C.

In certain embodiments, the capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C, $^{76}$Br, $^{123}$I, $^{131}$I, $^{67}$Ga, $^{111}$In and $^{99m}$Tc, or other radiolabeled products that may include gamma emitters, proton emitters, positron emitters, tritium, or covered tags detectable by other methods (i.e., gadolinium) among others. In a particular embodiment, the detection label is $^{18}$F. In certain embodiments, the capture agents may be modified to be used as imaging agents. The imaging agents may be used as diagnostic agents.

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Methods of Making/Screening Capture Agents

Provided herein in certain embodiments are methods of screening target-binding moieties and/or making capture agents that comprise these target-binding moieties. Methods for screening target-binding moieties and/or making capture agents that comprise these target-binding moieties can also be found in International Publication Nos. WO 2012/106671, WO 2013/033561, WO 2013/009869 and WO 2014/074907, each of which is incorporated by reference, herein, in their entireties.

The capture agent production methods disclosed herein begin with identification of a short-chain anchor peptide, then proceed by adding additional covalently coupled peptide ligands via a process that is promoted by the target protein. The specificity and inhibitory potency of the final multiligand capture agent are augmented by the peripheral peptide ligands.

In Vitro

For detection of BoNT Serotype A in solution, a capture agent of the invention can be detectably labeled, then contacted with the solution, and thereafter formation of a complex between the capture agent and the BoNT Serotype A target can be detected. As an example, a fluorescently labeled capture agent can be used for in vitro BoNT Serotype A detection assays, wherein the capture agent is added to a solution to be tested for BoNT Serotype A under conditions allowing binding to occur. The complex between the fluorescently labeled capture agent and the BoNT Serotype A target can be detected and quantified by, for example, measuring the increased fluorescence polarization arising from the complex-bound peptide relative to that of the free peptide.

Alternatively, a sandwich-type "ELISA" assay can be used, wherein a capture agent is immobilized on a solid support such as a plastic tube or well, then the solution suspected of containing BoNT Serotype A is contacted with the immobilized binding moiety, non-binding materials are washed away, and complexed polypeptide is detected using a suitable detection reagent for recognizing BoNT Serotype A.

For detection or purification of soluble BoNT Serotype A from a solution, capture agents of the invention can be immobilized on a solid substrate such as a chromatographic support or other matrix material, then the immobilized binder can be loaded or contacted with the solution under conditions suitable for formation of a capture agent/BoNT Serotype A complex. The non-binding portion of the solution can be removed and the complex can be detected, for example, using an anti-BoNT Serotype A antibody, or an anti-binding polypeptide antibody, or the BoNT Serotype A can be released from the binding moiety at appropriate elution conditions.

In Vivo Diagnostic Imaging

A particularly preferred use for the capture agents of the invention is for creating visually readable images of BoNT Serotype A or BoNT Serotype A-expressing cells in a biological fluid. The BoNT Serotype A capture agents disclosed herein can be converted to imaging reagents by conjugating the capture agents with a label appropriate for diagnostic detection. Preferably, a capture agent exhibiting much greater specificity for BoNT Serotype A than for other proteins is conjugated or linked to a label appropriate for the detection methodology to be employed. For example, the capture agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In another embodiment, rather than directly labeling a capture agent with a detectable label or radiotherapeutic construct, one or more peptides or constructs of the invention can be conjugated with for example, avidin, biotin, or an antibody or antibody fragment that will bind the detectable label or radiotherapeutic.

A. Magnetic Resonance Imaging

The BoNT Serotype A capture agents described herein can advantageously be conjugated with a paramagnetic metal chelate in order to form a contrast agent for use in MRI. Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, $Gd^{3+}$, is particularly preferred for MRI contrast agents, due to its high relaxivity and low toxicity, with the further advantage that it exists in only one biologically accessible oxidation state, which minimizes undesired metabolysis of the metal by a patient. Another useful metal is $Cr^{3+}$, which is relatively inexpensive. Gd (III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclo-tetradecane-1,4,7,10-tetraacetic acid (DOTA), 1-substituted 1,4,7,-tricarboxymethyl-1,4,7,10-teraazacyclododecane (DO-3A), ethylenediaminetetraacetic acid (EDTA), and 1,4,8,11-tetra-azacyclotetradecane-1,4,8,11-tetraacetic acid (TETA). Additional chelating ligands are ethylene bis-(2-hydroxyphenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTNA); derivatives of 1,5,10?N,N',N''-tris(2,3-dihydroxybenzoyl)-tricatecholate (LICAM); and 1,3,5-N,N',N''-tris(2,3-dihydroxybenzoyl)aminomethylbenzene (MECAM). A preferred chelator for use in the present invention is DTPA, and the use of DO3A is particularly preferred. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, all of which are hereby incorporated by reference.

In accordance with the present invention, the chelator of the MRI contrast agent is coupled to the BoNT Serotype A capture agent. The positioning of the chelate should be selected so as not to interfere with the binding affinity or specificity of the BoNT Serotype A capture agent. The chelate also can be attached anywhere on the capture agent.

In general, the BoNT Serotype A capture agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the BoNT Serotype A binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the BoNT Serotype A capture agent using such linkers (WO 95/28967, WO 98/18496, WO 98/18497 and discussion therein). The BoNT Serotype A binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity.

MRI contrast reagents prepared according to the disclosures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40: 298-310) and flow-spoiled gradient echo sequences (Edelman, R. et al., 1990. Radiology, 177: 45-50). These methods also include flow independent techniques that enhance the difference in contrast, such as inversion-recovery prepared or saturation-recovery prepared sequences that will increase the contrast between BoNT Serotype A positive tissue and negative tissues. Finally, magnetization transfer preparations also can improve contrast with these agents (Goodrich, K. et al., 1996. Invest. Radia, 31: 323-32).

Therapeutic Applications

Provided herein in certain embodiments are methods of using the BoNT Serotype A capture agents disclosed herein to inhibit the activity of BoNT Serotype A in vitro or in vivo. The BoNT Serotype A capture agents disclosed herein can be used to treat botulinism or improve one or more symptoms associated with botulinism.

In certain embodiments, the BoNT Serotype A capture agents disclosed herein are able to bind the occluded conformation of the BoNT Serotype A holotoxin.

This occluded conformation is removed when BoNT Serotype A is translocated inside of a cell, for example a neuron. This allows access for inhibitors to the enzymatic active site of BoNT Serotype A. In certain embodiments, the BoNT Serotype A capture agent binds to the protein before it is internalized into a cell, providing access for the active site binding portion of the capture agent when it is transferred into the cell along with the BoNT Serotype A protein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Screening Strategy for Botulinum Neurotoxin-Specific Ligand

Figure 2:
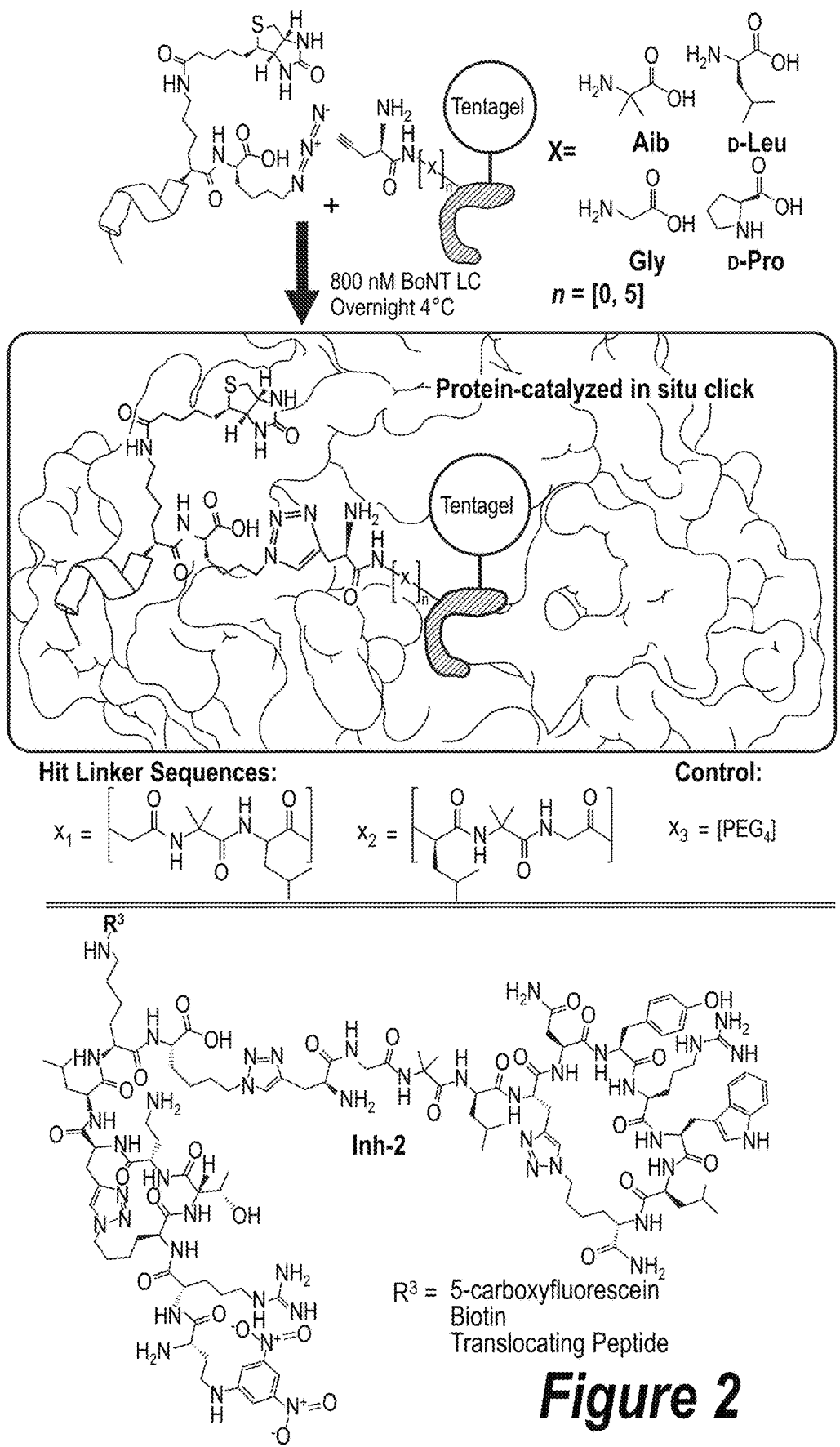
FIG. 2: Linker screen for divalent ligand development. Inh-1 was synthesized with a C-terminal azide and a biotin tag for readout of the in situ click screen and used in solution whereas L2 was synthesized with an N-terminal alkyne and a comprehensive linker library of oligopeptides of one to five units on Tentagel resin. An in situ protein-catalyzed click screen was performed to select for a minimally perturbative correctly oriented linker and resulted in hit sequences Gly-Aib-Leu and Leu-Aib-Gly. A PEG$_4$ linker was also used in preliminary assays as a comparison (See FIGS. 18 and 19). Inh-2 was the biligand chosen for all future assays.
Figure 6:
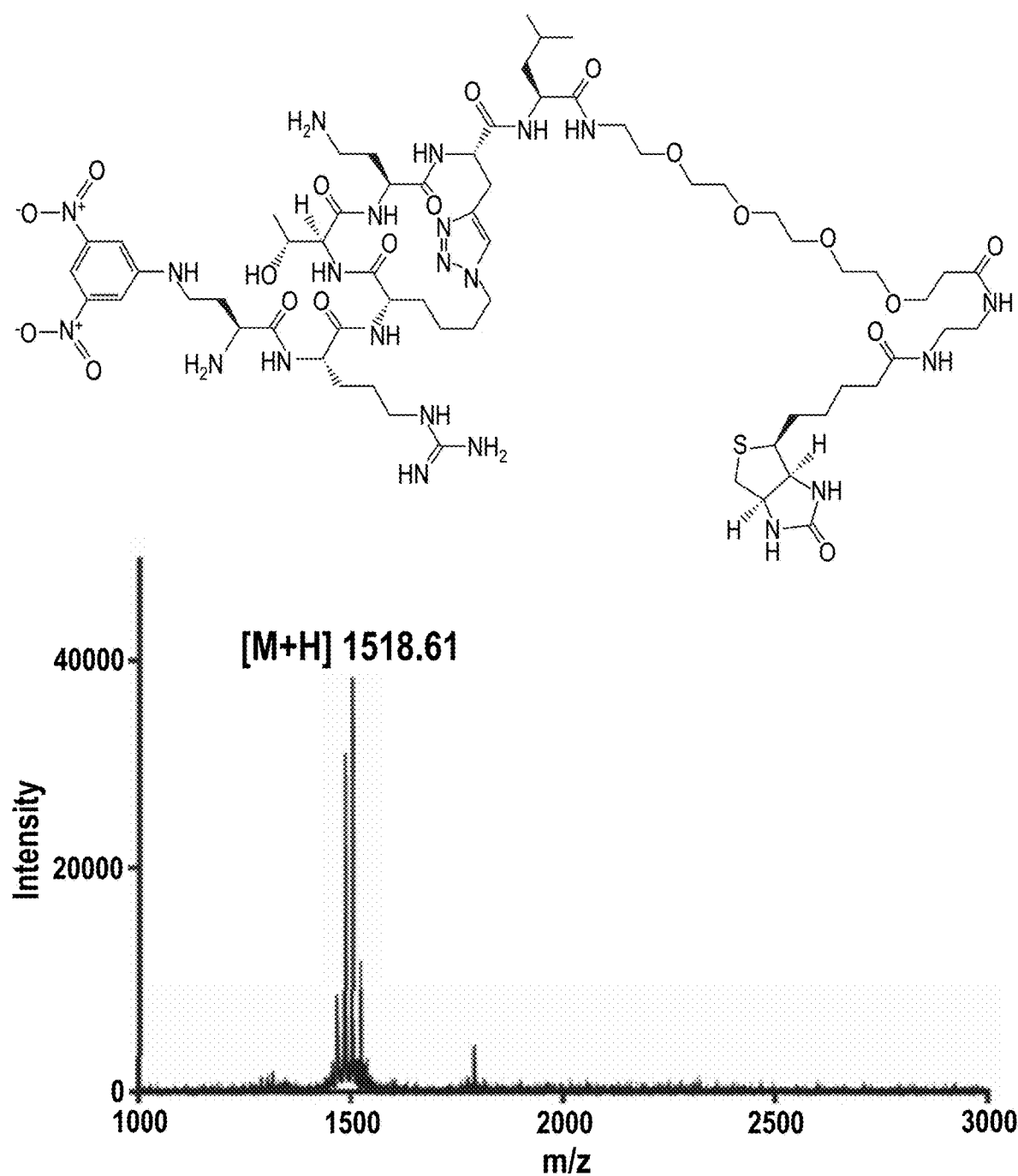
FIG. 6: Click cyclized BoNT LC inhibitor (Inh-1) (Biotinylated). Sequence Dab(DNP)-R-[Lys(N3)-T-Dab-Pra]-L-PEG$_4$-Biotin (SEQ ID NO:2) where square brackets indicate a closed cycle. Expected m/z 1518.77, observed m/z 1518.61.
Figure 7:
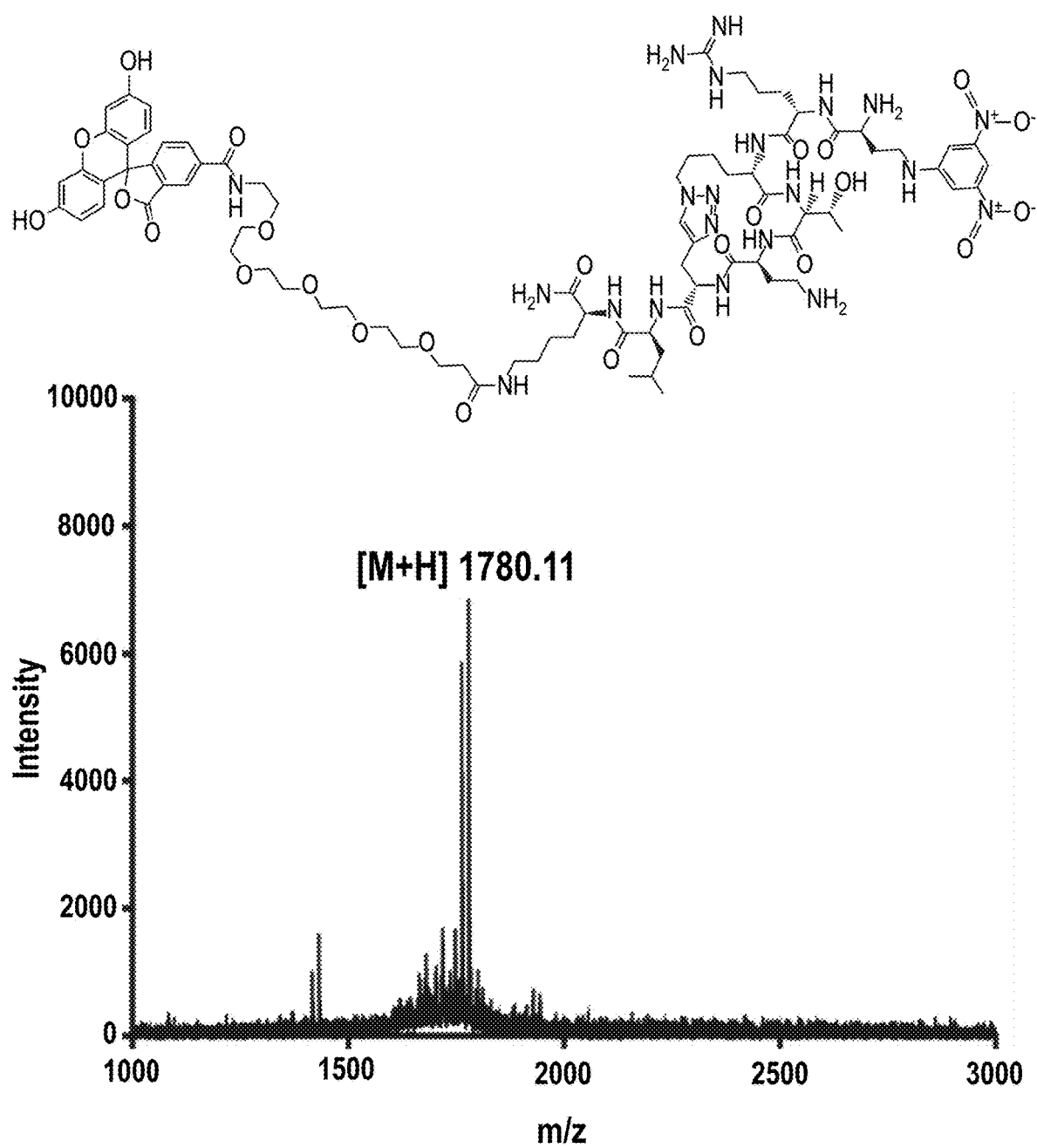
FIG. 7: Click cyclized BoNT LC inhibitor (Inh-1) (Fluorescein). Sequence Dab(DNP)-R-[Lys(N3)-T-Dab-Pra]-L-Lys(PEG$_5$-Biotin) (SEQ ID NO:3) where square brackets indicate a closed cycle. Expected m/z 1779.82, observed m/z 1780.11.
Figure 8:
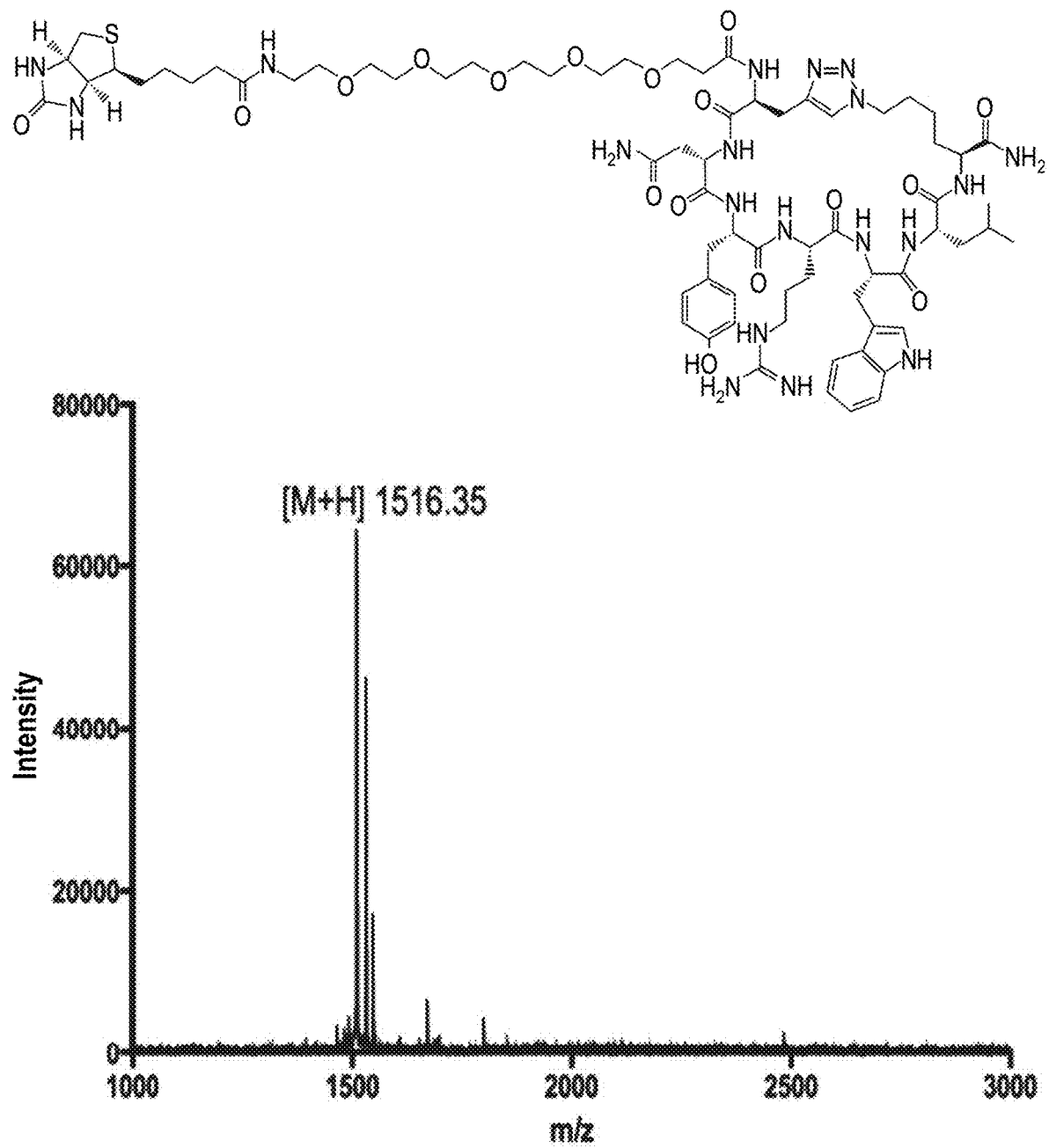
FIG. 8: L-2 cyclic secondary binder (Biotinylated). Sequence Biotin-PEG$_5$-[Pra-NYRWL-Lys(N3)] (SEQ ID NO:5) where square brackets indicate a closed cycle. Expected m/z 1516.75, observed m/z 1516.35.
Figure 9:
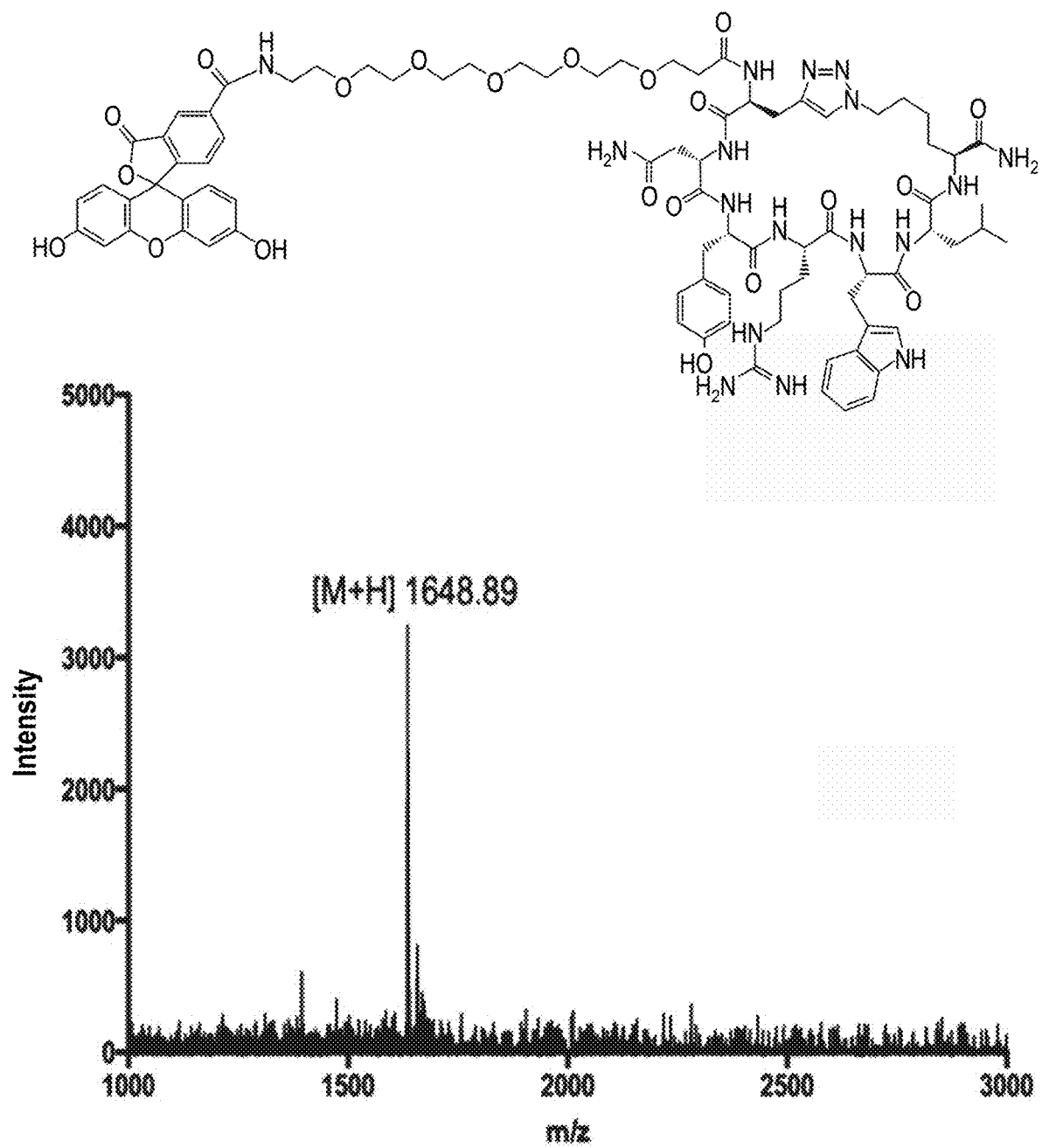
FIG. 9: L-2 cyclic secondary binder (Fluorescein). Sequence Fluorescein-PEG$_5$-Pra-NYRWL-Lys(N3) (SEQ ID NO:5) where square brackets indicate a closed cycle. Expected m/z 1648.72, observed m/z 1648.89.
Figure 10:
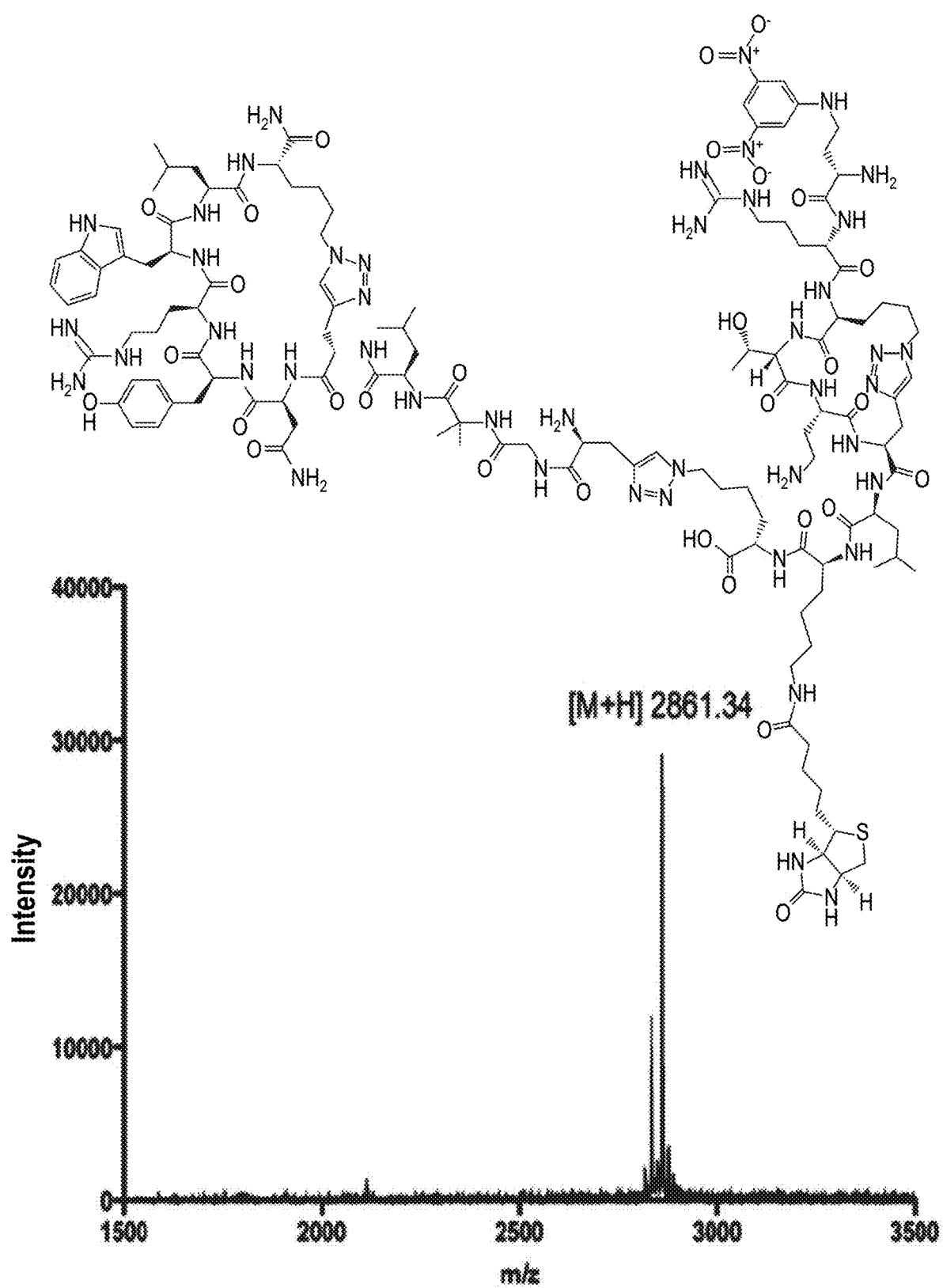
FIG. 10: Divalent Inhibitor with in situ selected G-Aib-L linker (Inh-2). Sequence NH$_2$-Dab(DNP)-R-[Lys(N3)-T-Dab-Pra]-L-Lys(Biotin)-T$_z$A-G-Aib-L-[Pra-NYRWL-Lys(N3)] ((SEQ ID NO:3)-T$_z$A-G-Aib-L-(SEQ ID NO:5)) where square brackets indicate a closed cycle. Expected m/z 2848.44, observed m/z 2851.23.

A macrocyclic peptide ligand was developed (Inh-1, FIGS. 6 and 7) that is a substrate mimic for BoNT. Inh-1 binds to the active site with a approximatlely 70 nM binding affinity ($k_D$) and similar inhibition constant. An all synthetic in situ click epitope targeting approach (shown in FIG. 1) was employed to identify a second peptide macrocycle (L2, FIGS. 8 and 9) that binds to a site a few angstroms away in the folded protein structure from the active site. L2 exhibits a $k_D$ of approximately 80 nM, but no inhibitory effects. Finally, an in situ click screen was utilized, promoted by the BoNT LC, to identify a linear peptide that connects the two macrocycles (shown in FIG. 2). The final divalent ligand (Inh-2, FIG. 10) inhibits the BoNT LC with an IC50 of 165±15 pM. Inh-2 is also carried into neuronal cells by BoNT itself, and inhibits the holotoxin in live cells. This technique provides a potentially general route for the development of peripheral and active site binders from naive libraries for combination through in situ click target-guided synthesis.

Figure 3A:
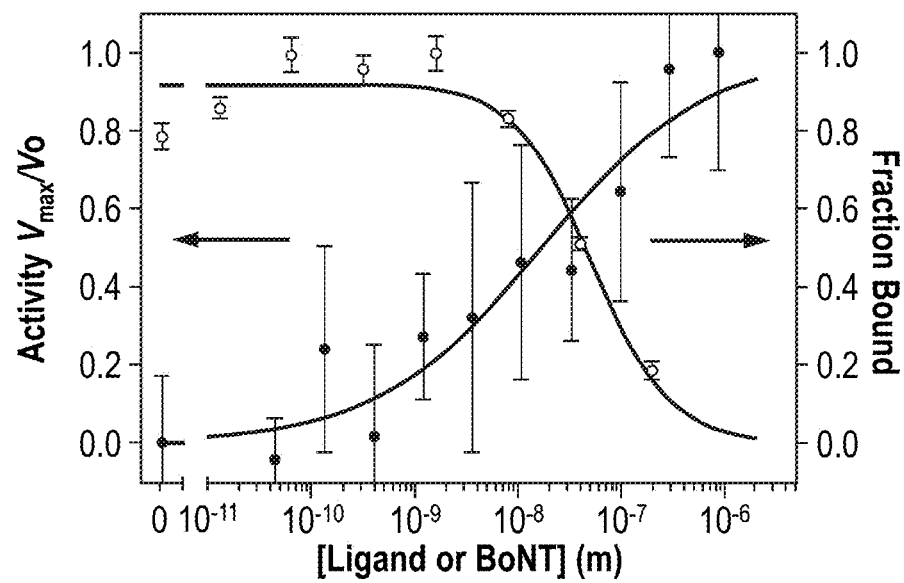
FIGS. 3A-3D: Characterization of ligand binding and inhibition in vitro.
Figure 11:
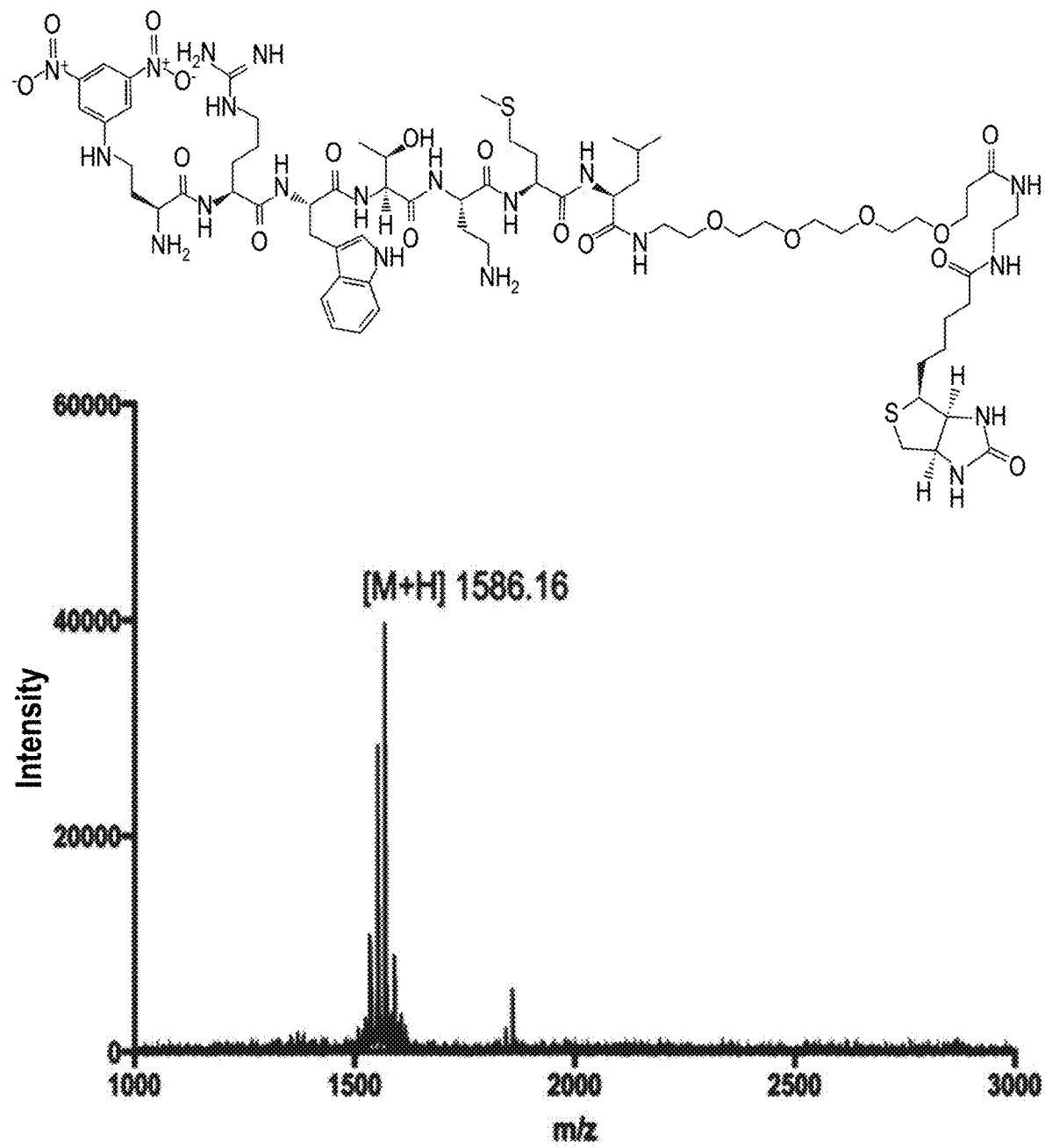
FIG. 11: Literature 310 helical BoNT LC inhibitor (biotinylated). Sequence Dab(DNP)-RWT-Dab-ML-PEG$_4$-Biotin (SEQ ID NO:8). Expected m/z 1586.81, observed m/z 1586.16.
Figure 12:
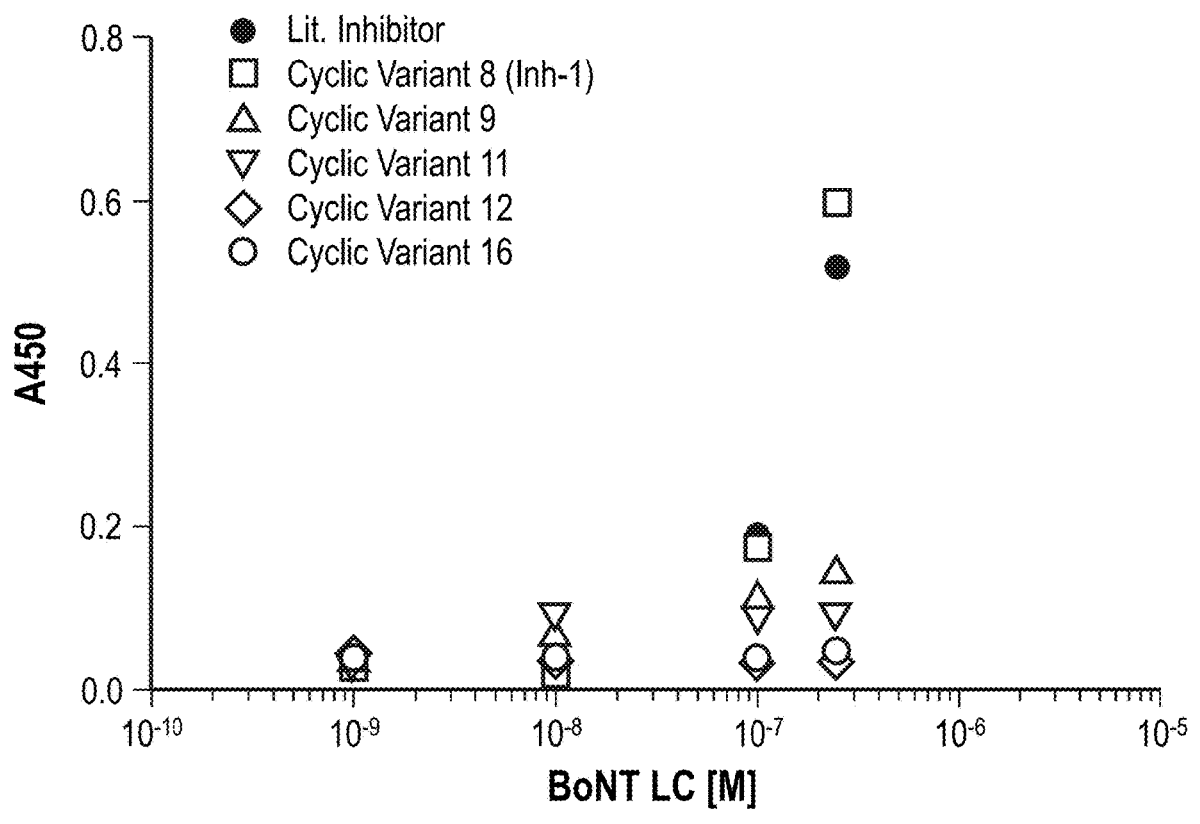
Figure 13A:
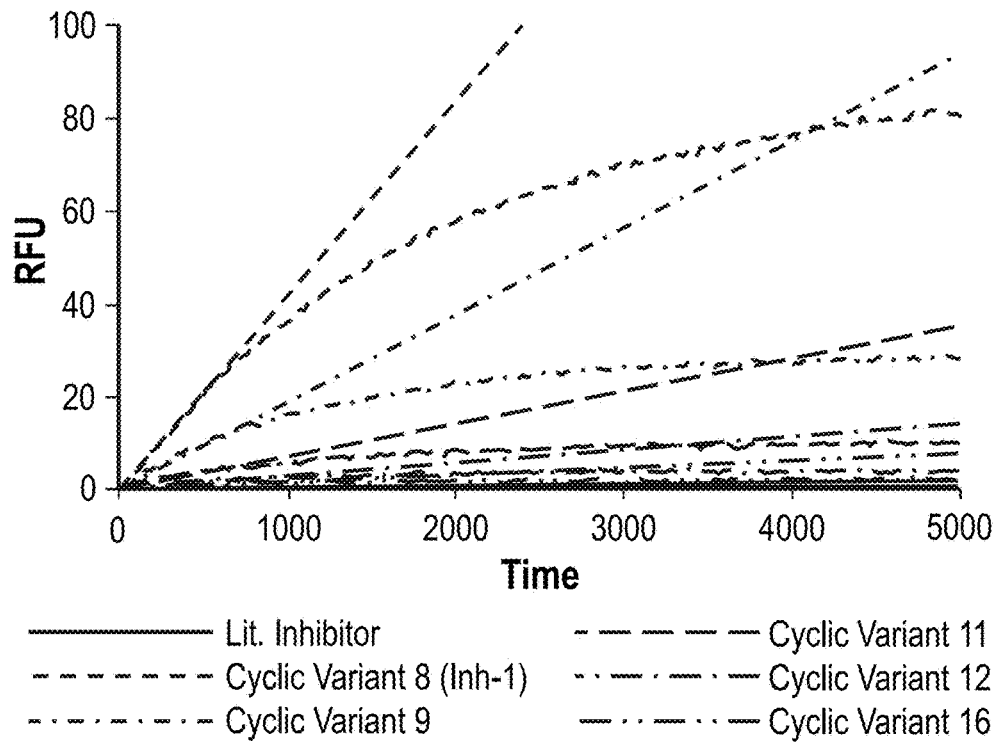
Figure 13B:
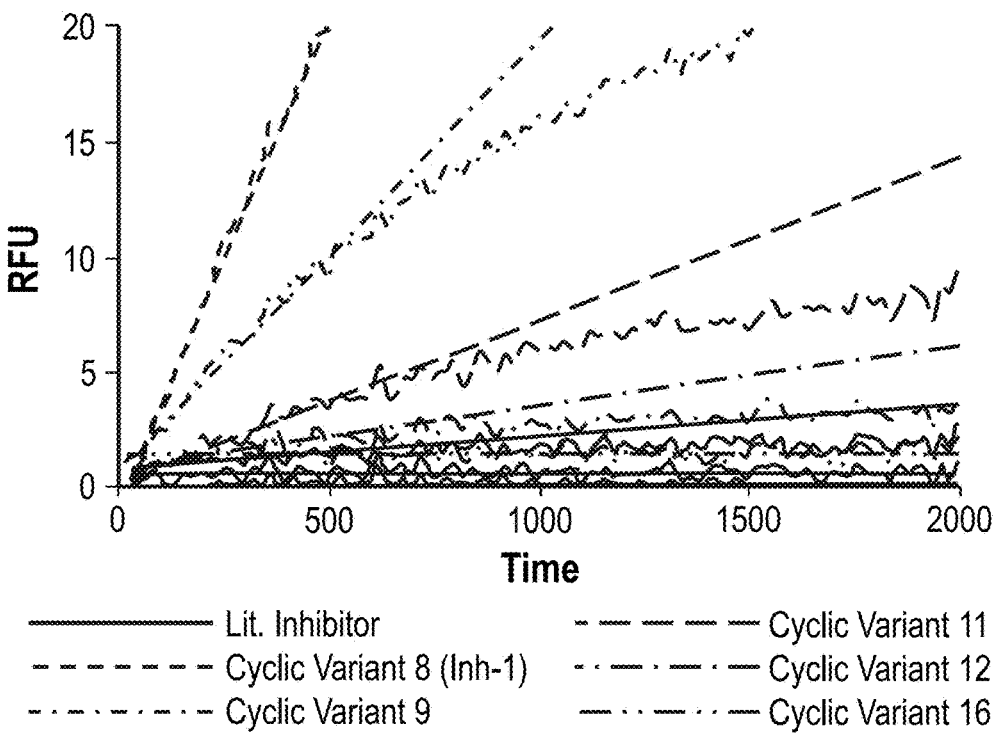
Figure 13C:
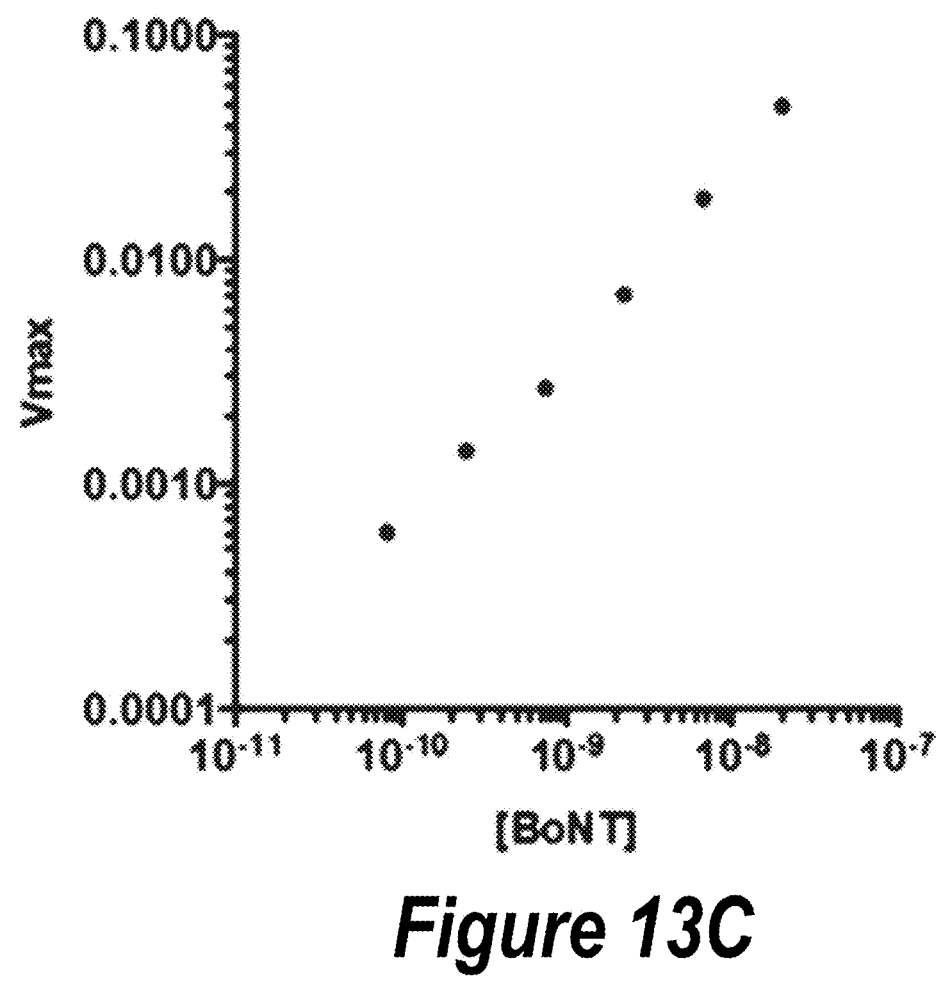

The active site of the catalytic BoNT/A LC recognizes the 7-residue QRATKML (SEQ ID NO:12) sequence of the SNAP-25 protein. Many inhibitors based on this motif have been reported. One peptidomimetic inhibitor variant resulting from a structure-based search binds BoNT in a tight $3_{10}$ helical conformation with low nanomolar inhibition of BoNT LC in vitro (FIGS. 11 and 12). In an effort to reinforce this conformation in solution and increase chemical and biological stability of this compound, a small library of (i, i+3)-click cyclized derivatives was synthesized. One compound (Inh-1) inhibited BoNT/A LC with a 70±8 nM inhibition constant measured in vitro using a FRET-based substrate cleavage assay (FIGS. 13A-13C) and 68±29 nM binding affinity using fluorescence polariNation (FIG. 3A). However, inhibiting the full BoNT holotoxin with the occluded LC active site is more challenging. Single point ELISA binding data (FIG. 3D) shows that the Inh-1 exhibits minimal binding to the holotoxin despite tight binding to the LC. Thus, Inh-1 was expanded to include a moiety that binds to a non-occluded region of BoNT LC adjacent to the active site. For this purpose, an epitope which is solvent exposed in the occluded conformation of the holotoxin was selected for screening with epitope-catalyed in situ click.

Figure 3B:
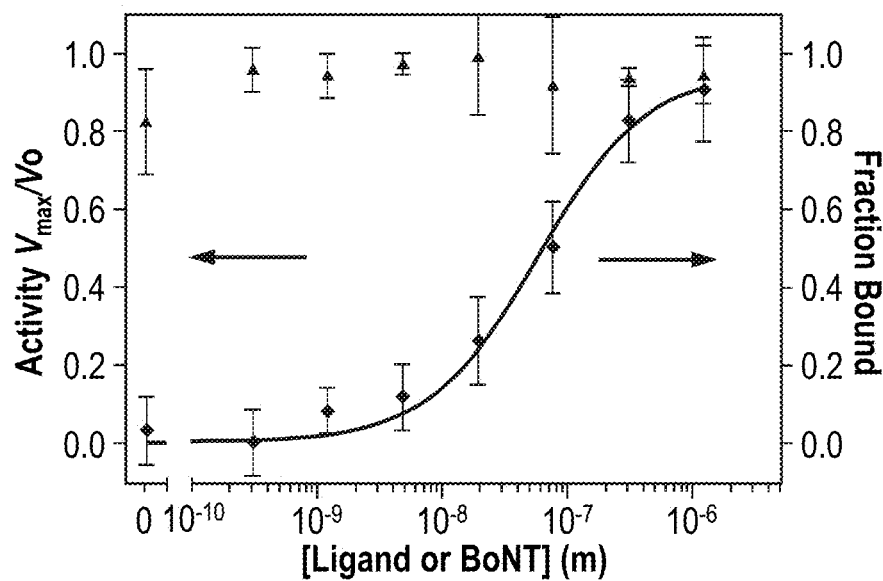
Figure 14:
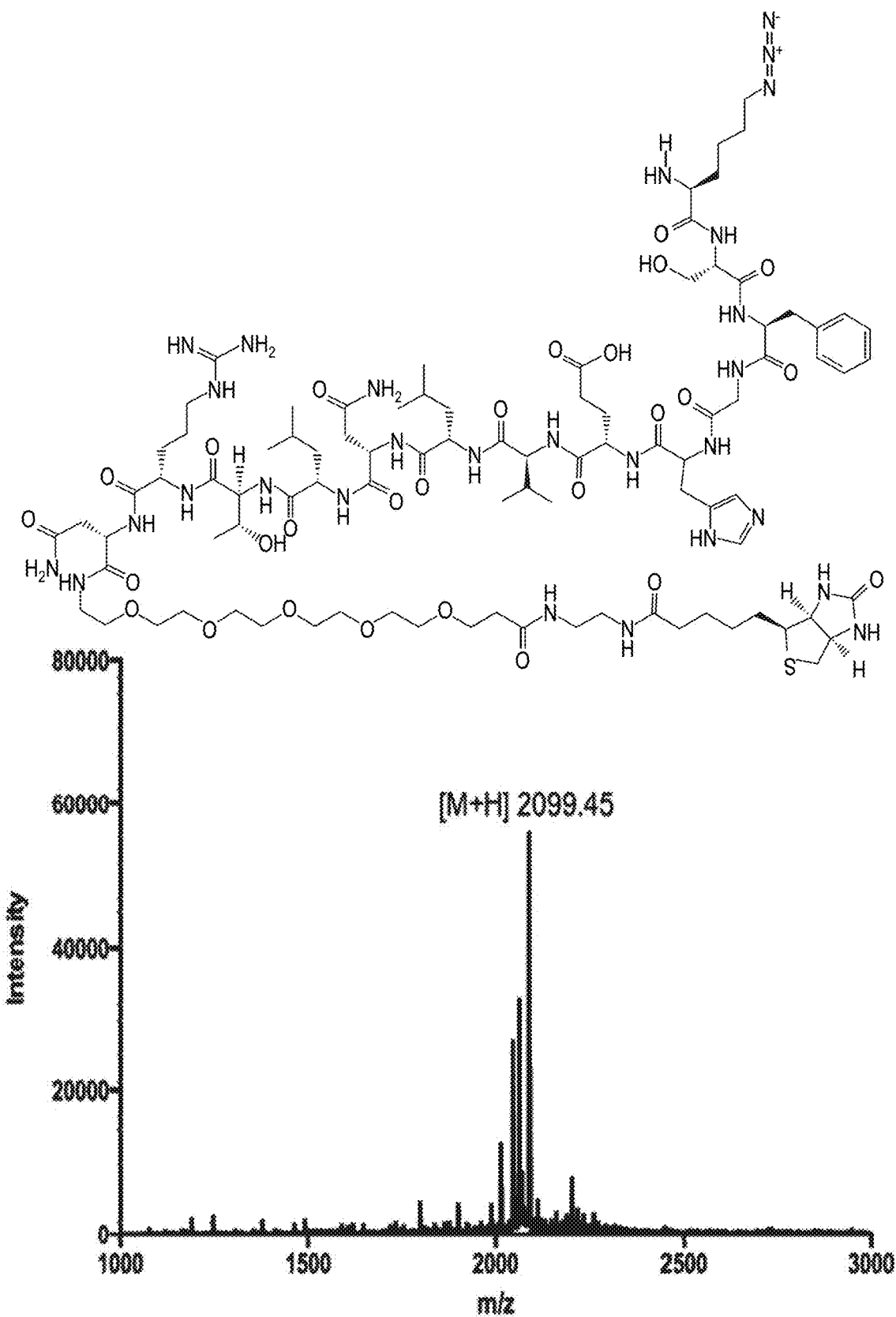
FIG. 14: MALDI-TOF spectrum of biotinylated BoNT LC fragment. Amino acids 166-179 of BoNT LC. Sequence Lys(N3)-SFGHEVLNLTRN-PEG$_4$-Biotin (SEQ ID NO:9). Expected m/z 2099.09, observed m/z 2099.45.
Figure 15:
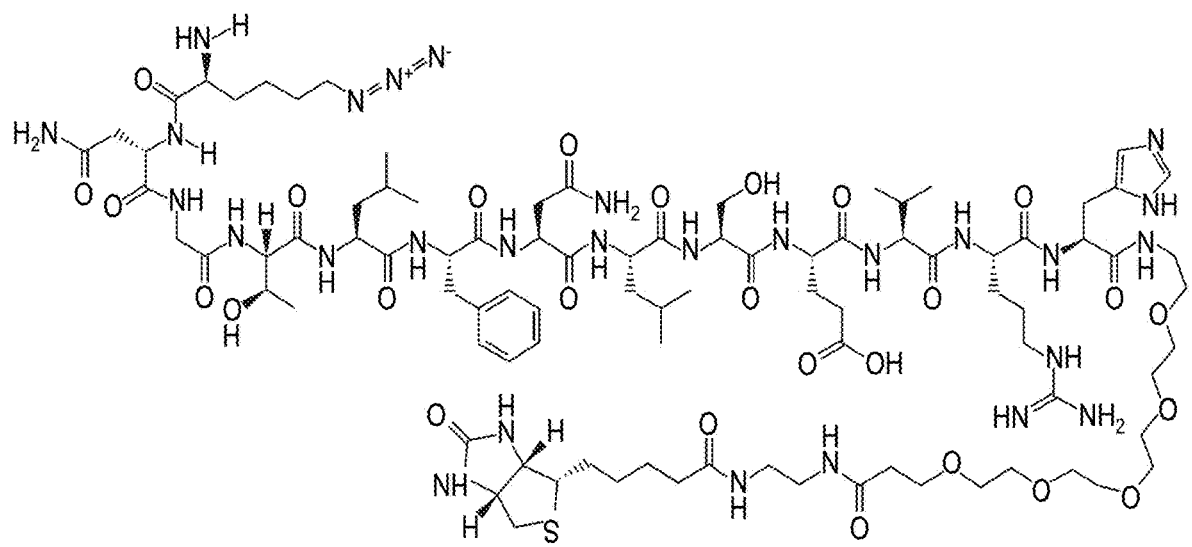
FIG. 15: MALDI-TOF spectrum of biotinylated scrambled fragment. Sequence Lys(N3)-NGTLFNL-SEVRH-PEG$_4$-Biotin (SEQ ID NO:10). Expected m/z 2099.09, observed m/z 2098.06.
Figure 15:
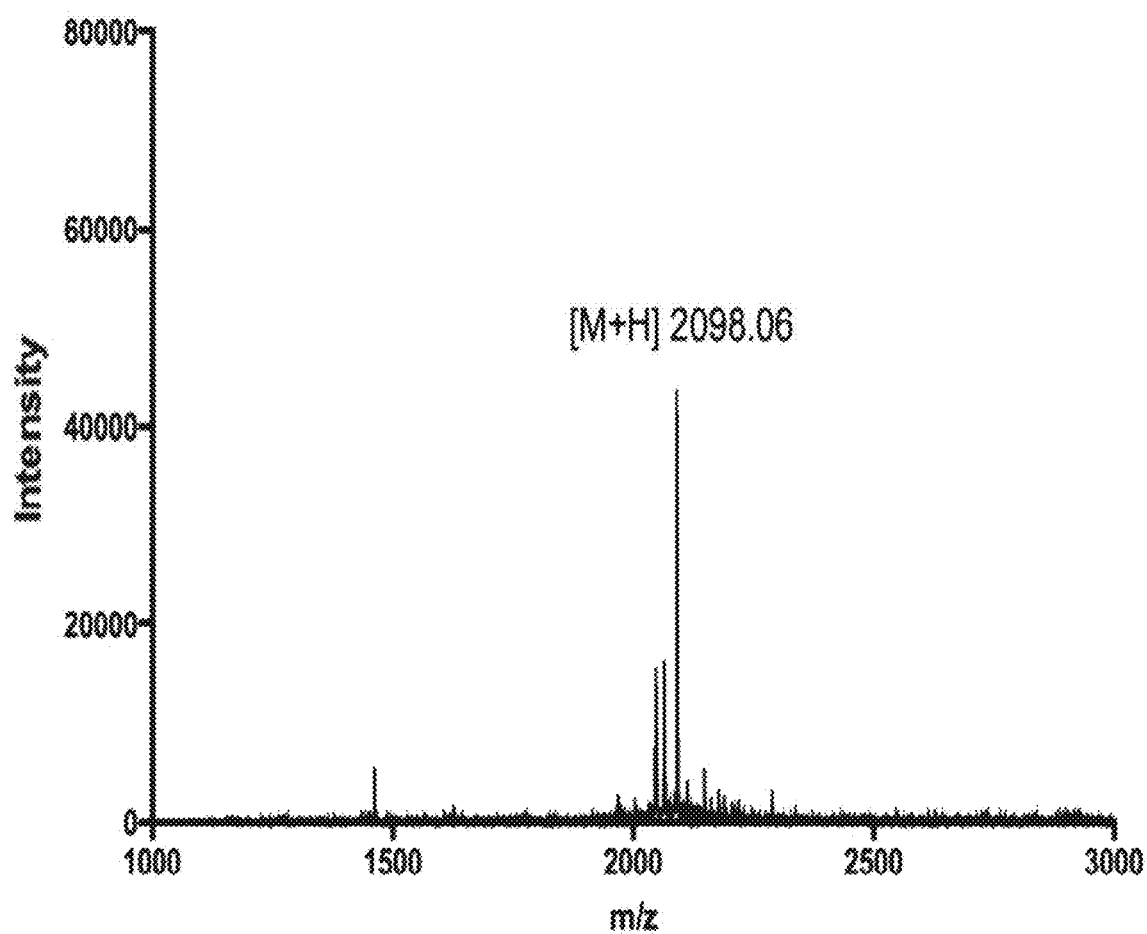

The epitope (BoNT LC residues 166-179, FIG. 14) was synthesized with an N-terminal azidolysine and a C-terminal biotin and was screened against a 1.1M element library of macrocyclic 5-mer peptides synthesized on Tentagel resin substituted with an N-terminal propargylglycine (shown in FIG. 2) and anti-screened against a scrambled version of the same epitope (FIG. 15). This constrained macrocyclic peptide library was used due to the increased stability and decreased entropic penalty of binding relative to linear peptides. After incubation with the target epitope, beads were stripped, probed and developed with an alkaline phosphatase anti-biotin mAb. Nine hit beads were sequenced using Edman degradation and found to have significant sequence homology (FIG. 16). L2 was selected after fluorescence polarization showed a 78±13 nM binding affinity to both the BoNT LC and the BoNT holotoxin, but no measurable LC inhibition (FIG. 3B).

Figure 17:
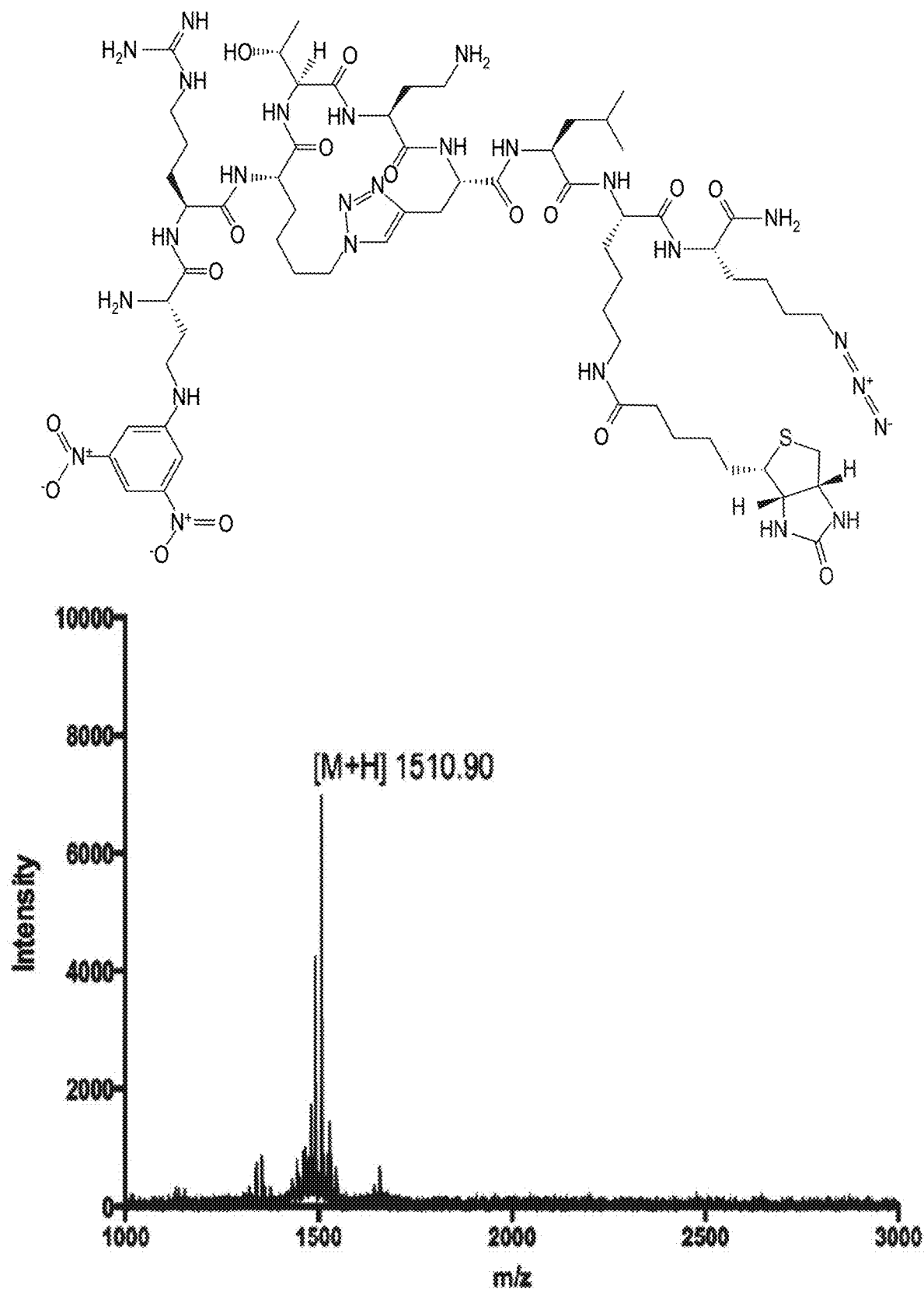
FIG. 17: Click cyclized BoNT LC inhibitor (Inh-1) for target-guided screen. Sequence Dab(DNP)-R-[Lys(N3)-T-Dab-Pra]-L-Lys(Biotin)-Lys(N3) (SEQ ID NO:4). Expected m/z 1510.77, observed m/z 1510.90.
Figure 18:
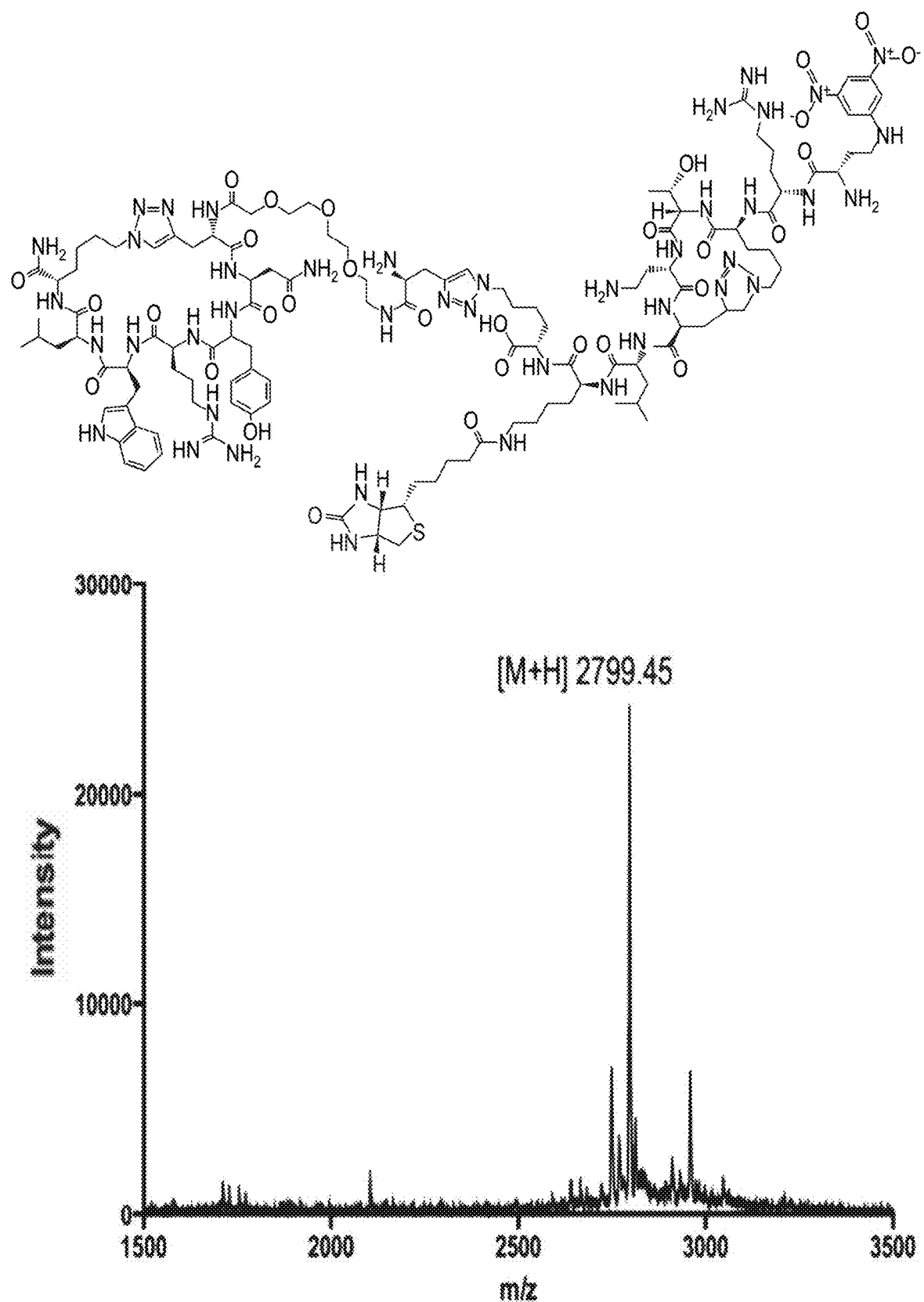
FIG. 18: Divalent Inhibitor (Inh-2) with PEG$_4$ linker. Sequence NH$_2$-Dab(DNP)-R-[Lys(N3)-T-Dab-Pra]-L-Lys(Biotin)-T$_z$4-PEG$_4$-[Pra-NYRWL-Lys(N3)] ((SEQ ID NO:3)-T$_z$4-PEG$_4$-(SEQ ID NO:5)). Expected m/z 2801.38, observed m/z 2799.45.
Figure 19:
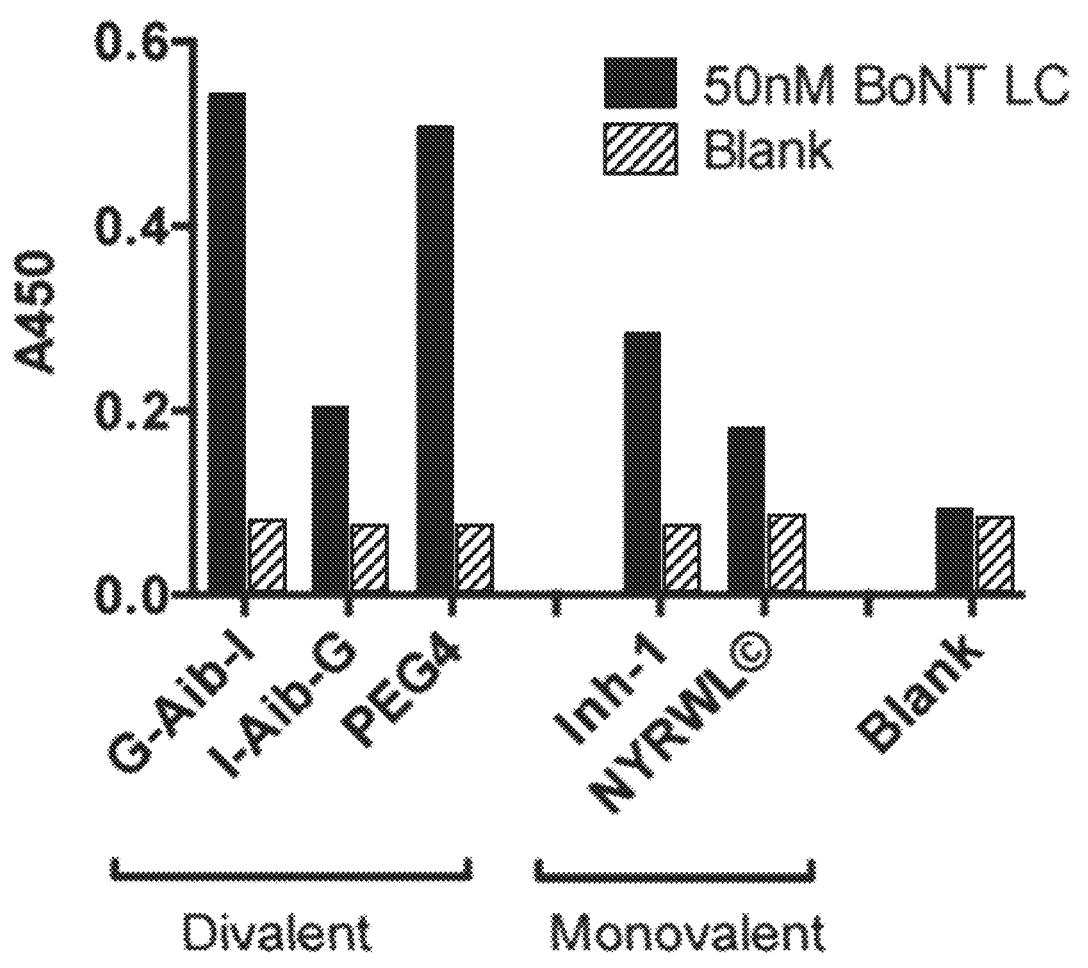
Figure 20:
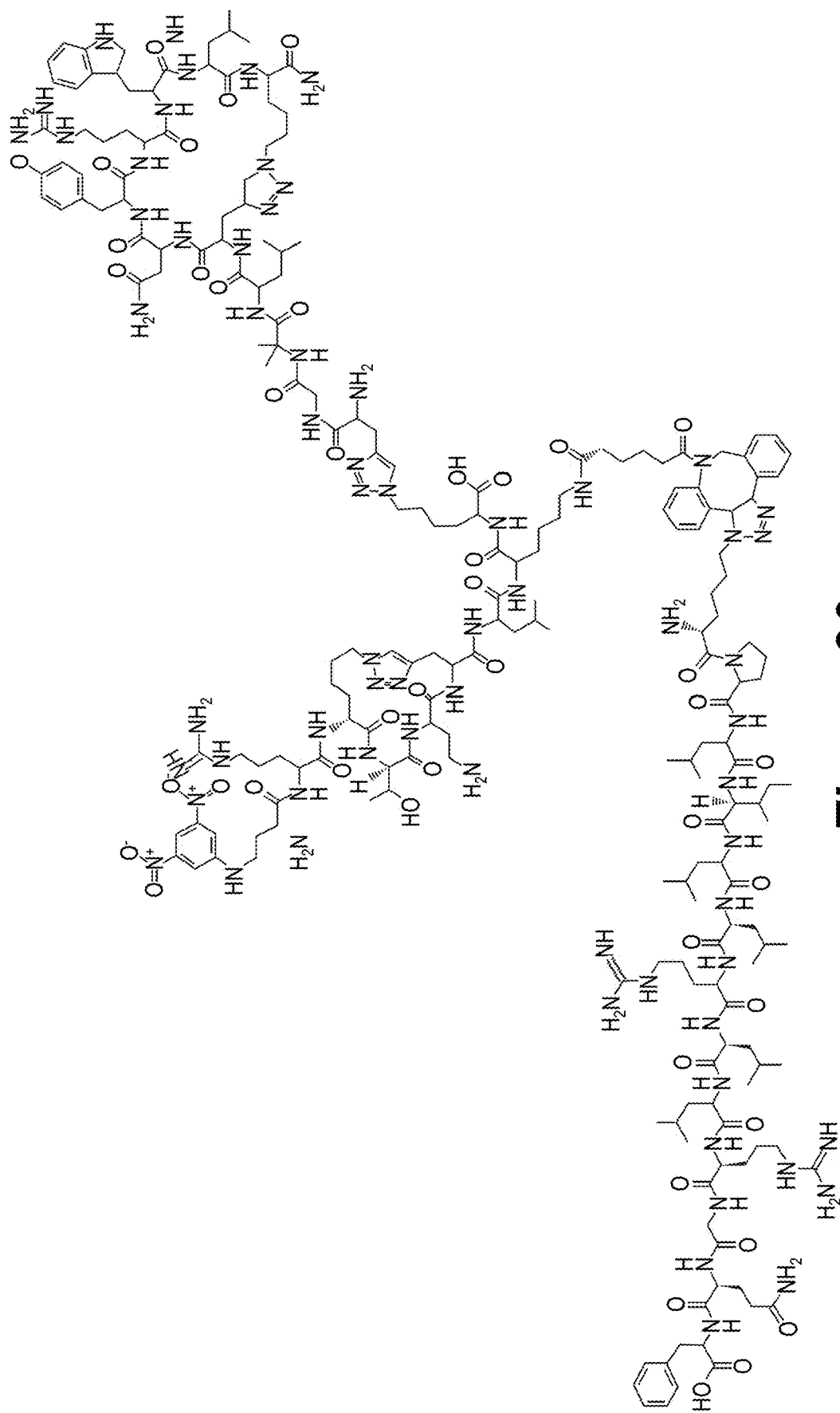
FIG. 20: Divalent Inhibitor with G-Aib-L linker and STP (Inh-2-STP). Sequence NH$_2$-Dab(DNP)-R-[Lys(N3)-T-Dab-Pra]-L-Lys(DBCO-STP)-T$_z$4-G-Aib-L-[Pra-NYRWL-Lys(N3)] ((SEQ ID NO:3)-T$_z$4-G-Aib-L-(SEQ ID NO:5)), where STP is D-peptide Lys(N3)-pliylrllrGqf (SEQ ID NO:11). Expected m/z 4533.21, observed m/z 4536.45.
Figure 20:
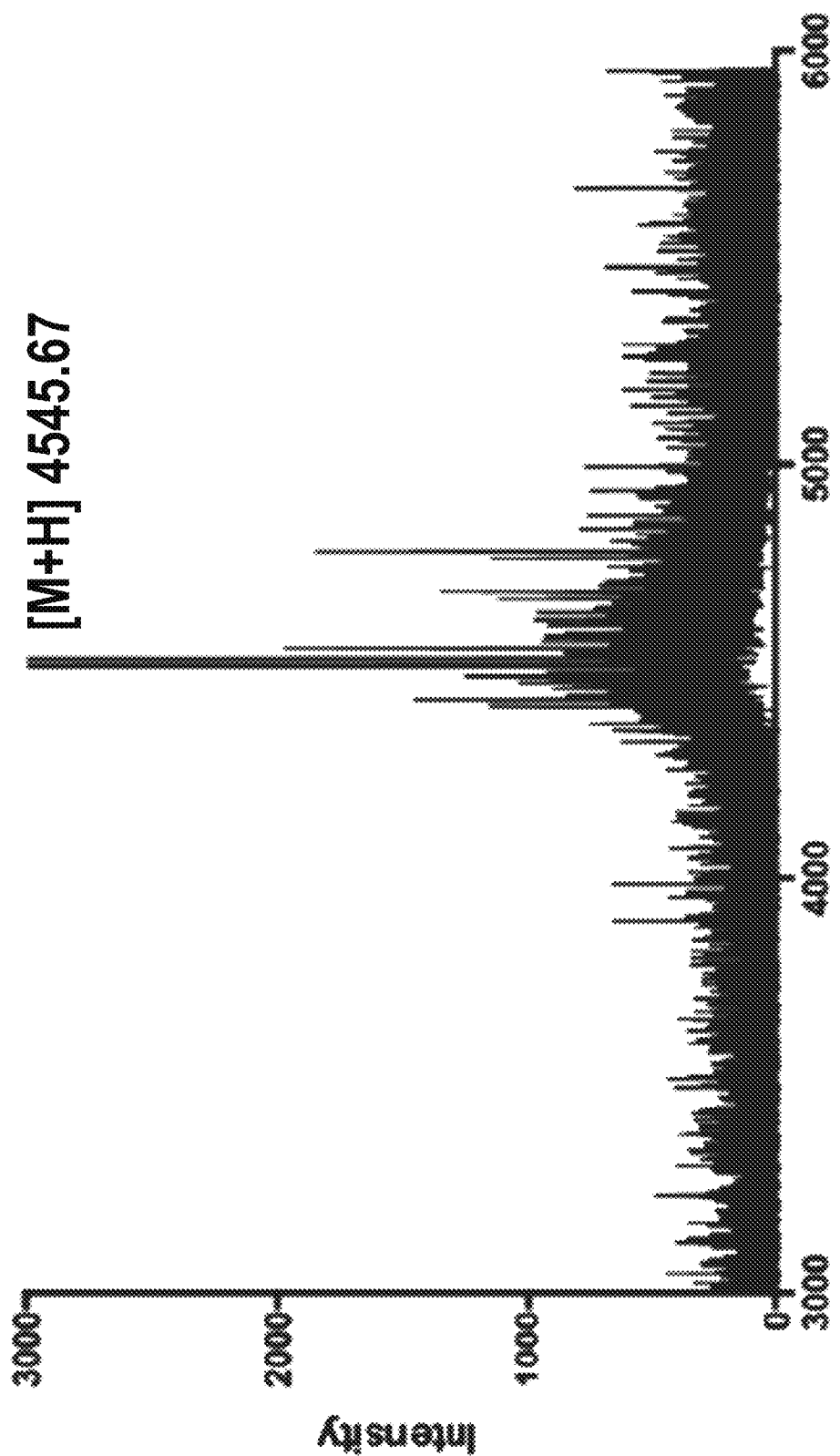

To optimally combine Inh-1 with L2, kinetic in situ target-guided synthesis was used with a combinatorial linker library, (shown in FIG. 2) to identify an optimized molecular bridge. To this end, L2 was synthesized on Tentagel resin and appended with an N-terminal linker library that was terminated with a propargylglycine. This appended library was comprehensive from zero to five residues in four non-canonical and alternate chirality amino acids that were selected for structural rigidity. The rational for this library was to maximize the avidity enhancement that can be achieved when combining two independent binders. That enhancement is maximized with a rigid linker of length equal to the root mean square average separation of the two binding sites. Inh-1 was synthesized with a C-terminal azidolysine and a biotin assay handle (FIG. 17). The BoNT LC was added to promote the target guided synthesis of a bivalent ligand by bringing the reactive azide and alkyne groups in close proximity. After screening, beads were stripped, probed and developed with an alkaline phosphatase anti-biotin mAb. Hit beads were sequenced using Edman degradation and resulted in a consensus of two linker sequences: Gly-Aib-Leu and Leu-Aib-Gly (shown in FIG. 2). A control bivalent ligand was synthesized with a $PEG_4$ linker of similar RMSD length to compare to the linkers selected through target-guided synthesis (FIGS. 18 and 19). Candidate bivalent ligands were scaled up and evaluated as inhibitors of BoNT LC in vitro as above. Inh-2 was selected for all subsequent assays and demonstrated an inhibition constant of 165±15 pM against BoNT LC. Variants of this ligand were synthesized with a fluorescein dye for fluorescence polarization, a biotin for binding assays and a spontaneously translocating peptide (STP) reported for the delivery of polar cargo to the cytosol (FIG. 20).

Figure 4A:
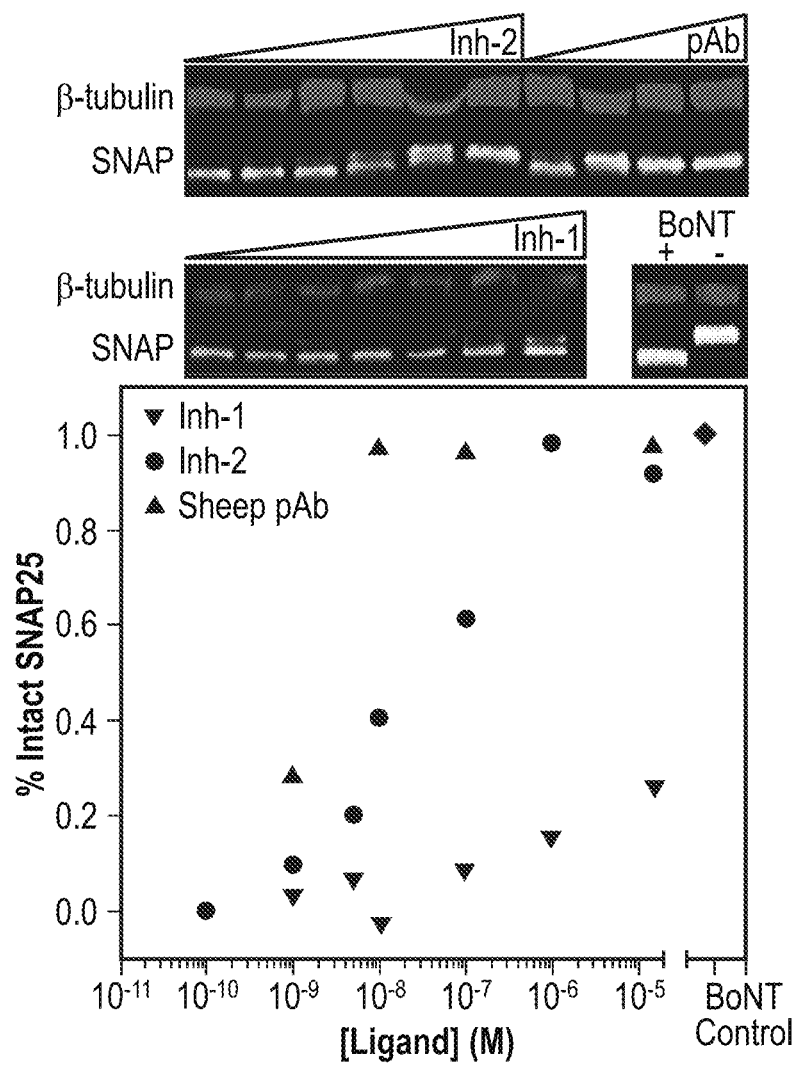
FIGS. 4A and 4B: Ligand inhibition effect in a hiPSC-derived neuron system with BoNT holotoxin.
Figure 21:
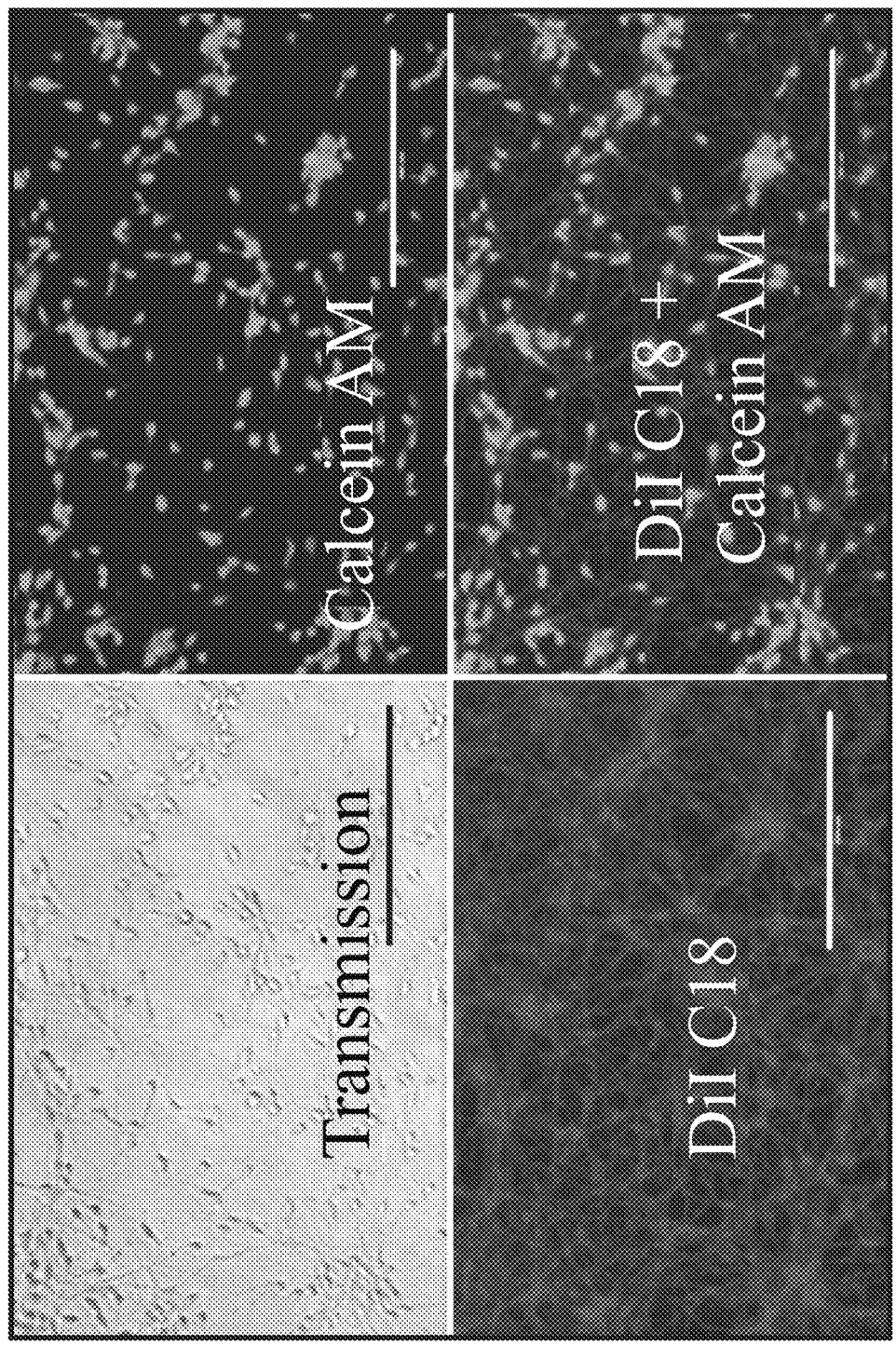
FIG. 21: Neurite outgrowth in iCell Neurons. Neurons 4 days after plating were stained according to the manufacturers instructions with Neurite Outgrowth and Viability stains (Life Technologies), consisting of a Calcein viability stain (green) and a Dil C18 membrane stain (blue). All cells show a morphology consistent with neuronal outgrowth.
Figure 22A:
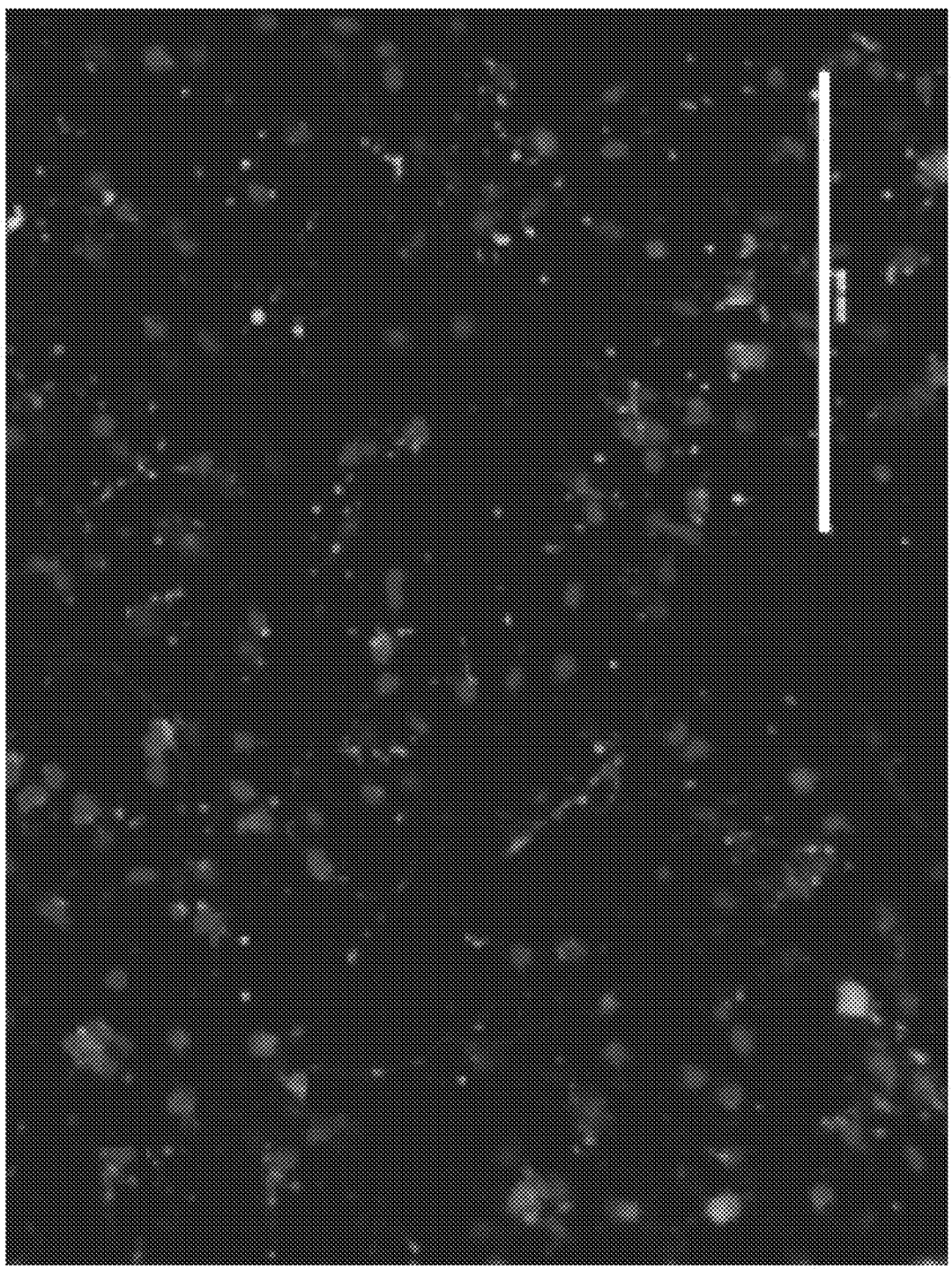
FIGS. 22A-22D: Synaptic vesicle recycling in iCell Neurons. FM1-43 stain (yellow) and nuclear stains (red) on live neurons after 15 days post-plating.
Figure 22B:
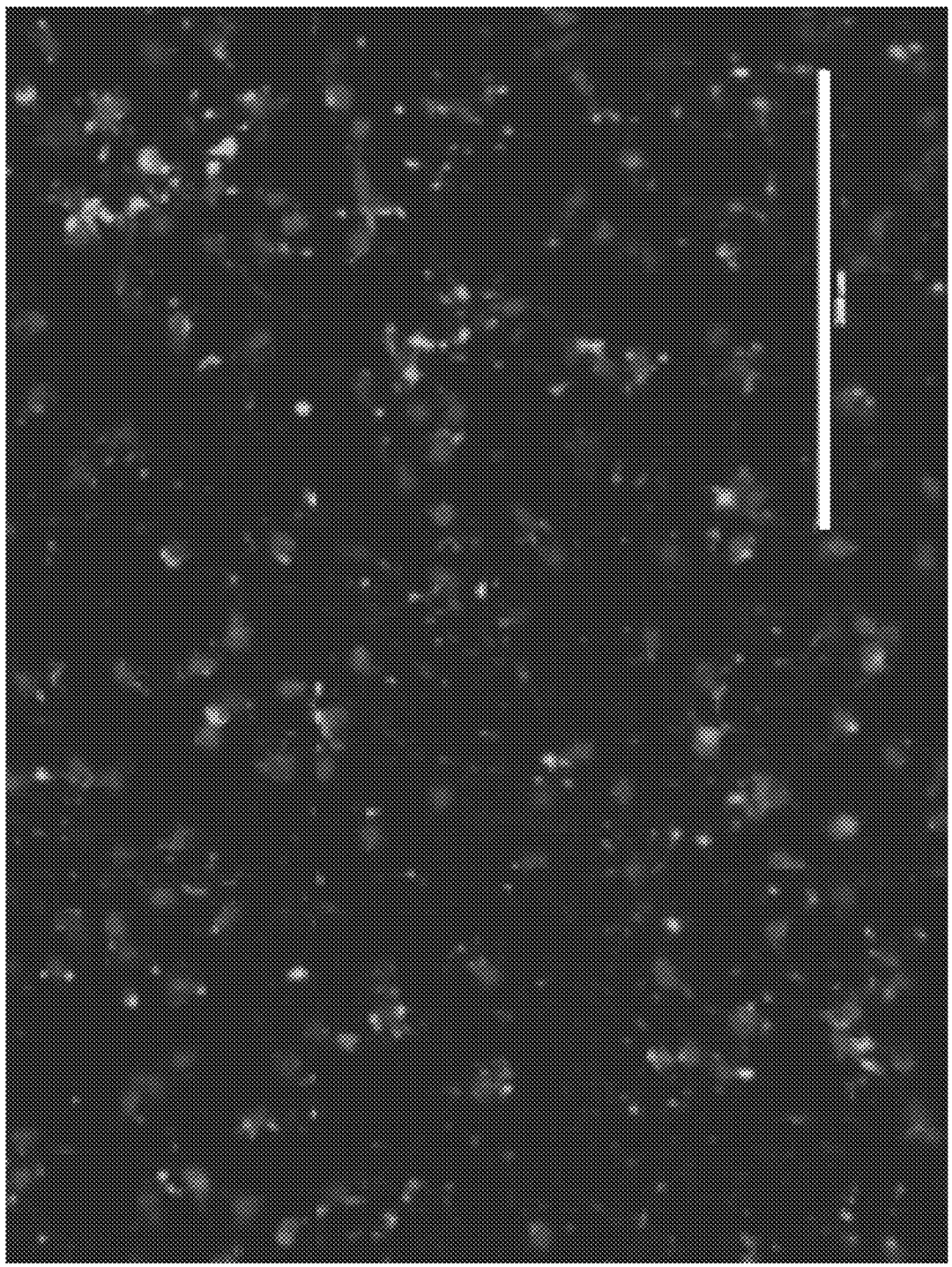
Figure 22C:
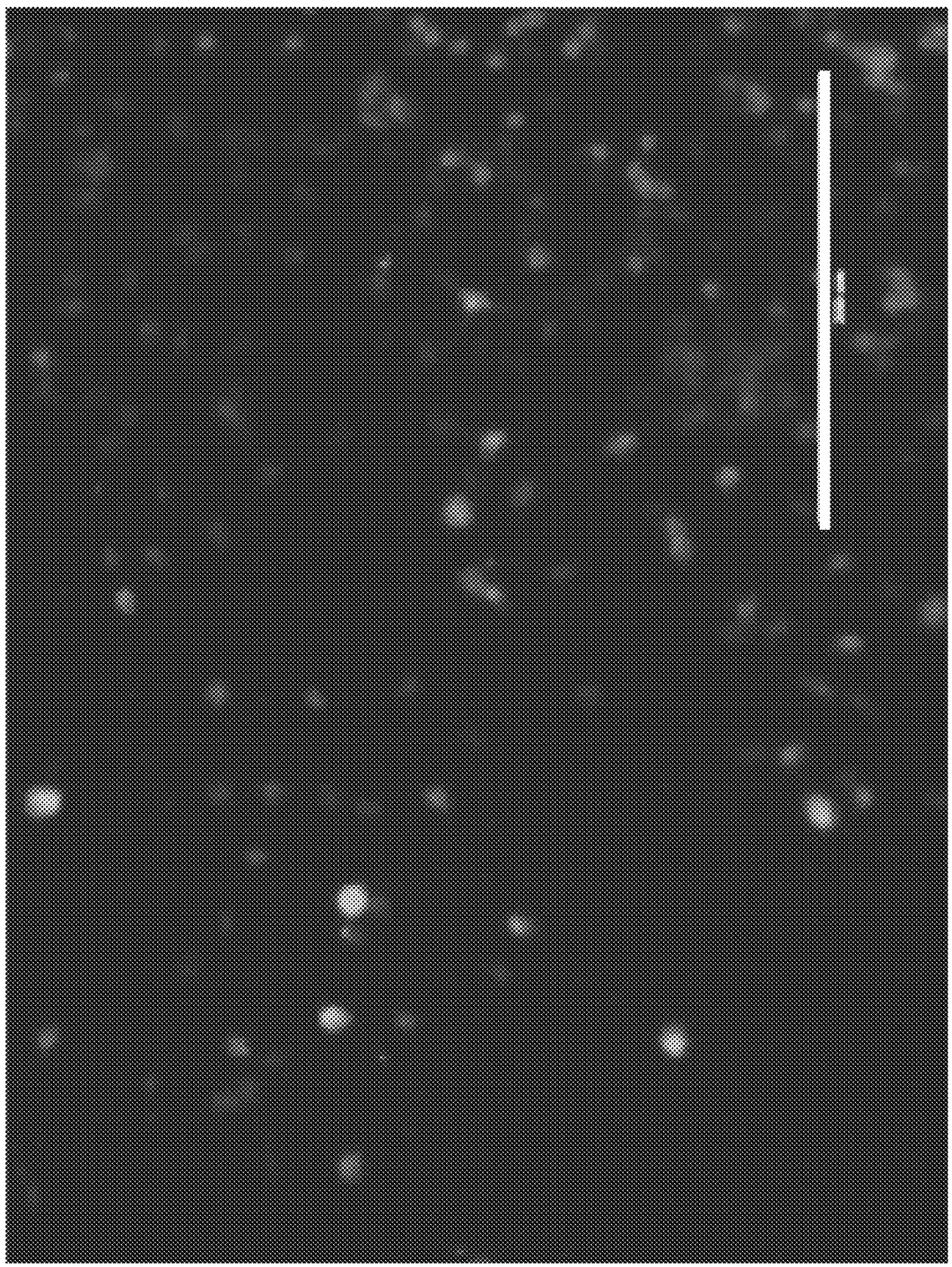
Figure 22D:
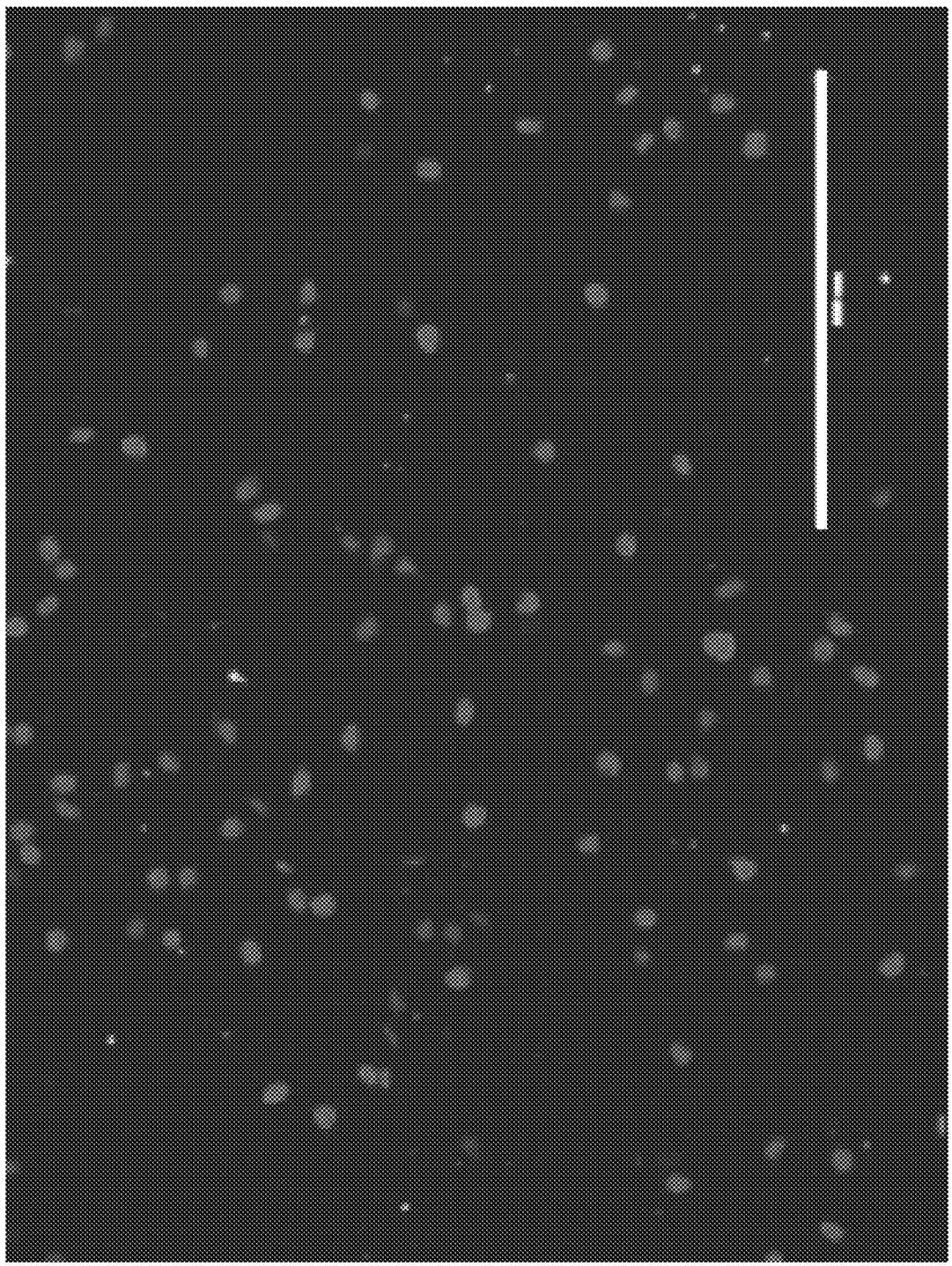

The ability of Inh-2 to protect and rescue BoNT intoxication in human neurons was tested (FIGS. 4A-4B and 5A-5C respectively). Used was a type of human induced pluripotent stem cell derived neurons known as iCell neurons, which have been reported as a sensitive model for monitoring SNAP-25 cleavage by BoNT in the complex environment of living cells (FIG. 21). Cells were plated on poly-D-lysine coated 96-well plates with a laminin matrix and exposed to 2 mouse $LD_{50}$ units (U) of BoNT pre-incubated with various concentrations of Inh-1 and Inh-2. All cells were lysed after 24 hours and evaluated for SNAP-25 cleavage by western blotting. Cleaved SNAP-25 appeared as a second band under the intact SNAP-25 band (FIG. 4A). Western blotting data was quantified by densitometry to extract a dose-response behavior of the ligands in protection against BoNT intoxication. Inh-1 exhibited negligible protective effects at up to 10 μM dosing. This is likely due to the occluded active site being unavailable for binding until BoNT enters the cytosol, and the membrane impermeable nature of Inh-1. Inh-2 is also impermeable to cell membranes, but demonstrated significant protective effect to BoNT intoxication at concentrations as low as 100 nM. This type of protection has been reported for inhibitors of the BoNT LC active site in neuron models, but only at inhibitor concentrations in the mid micromolar range. As a comparison, a polyclonal antibody acquired from the Army Critical Reagents program repository with known significant antitoxin effect was evaluated. This antibody protects against BoNT intoxication by interrupting the heavy chain receptor-mediated endocytosis and provides significant protection into the low to mid nanomolar range.

Figure 4B:
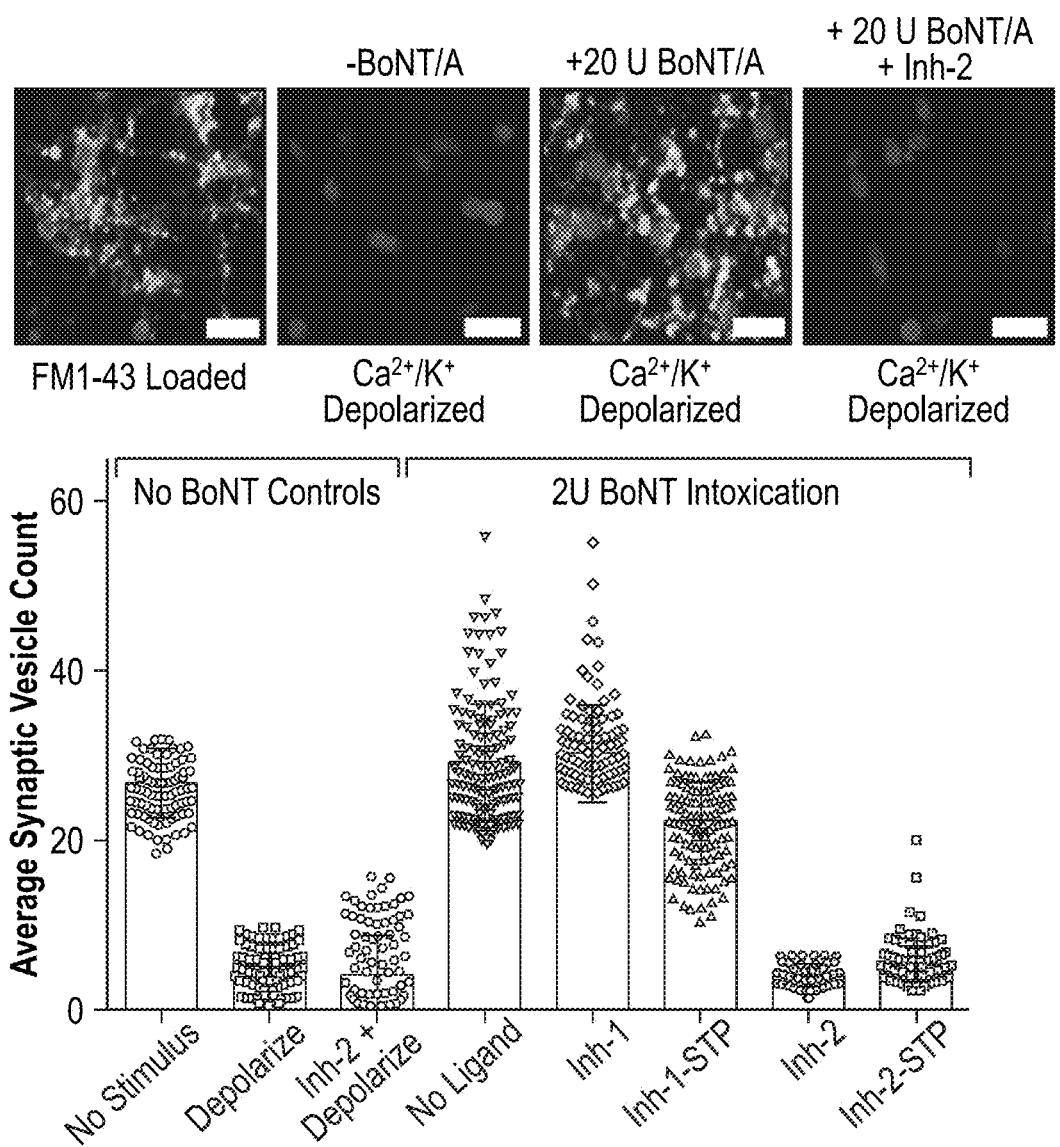
Figure 23:
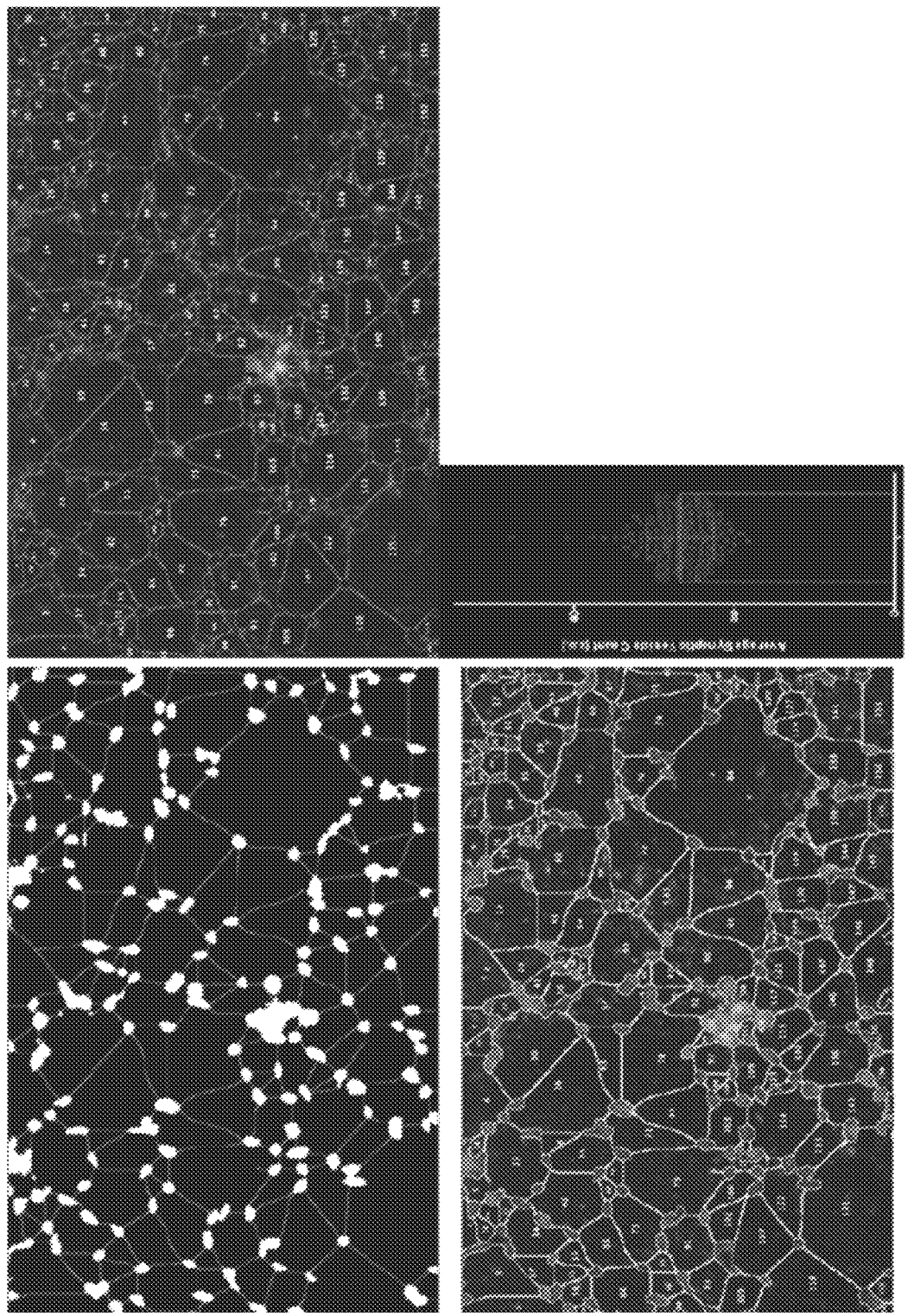
FIG. 23: Image analysis of synaptic vesicle intensity. Images were analyzed by ImageJ. A watershed analysis was used to find the edges of neuron cell bodies in the transmission channel and allocate a given intercellular area to each cell. These areas were then mapped onto the FM1-43 layer and puncta were counted in each area using the PunctaAnalyzer package while ignoring the previously identified cell bodies to find only synaptic vesicle puncta along neurites. The puncta count for each cell was averaged over two wells with two fields of view per well.
Figure 24:
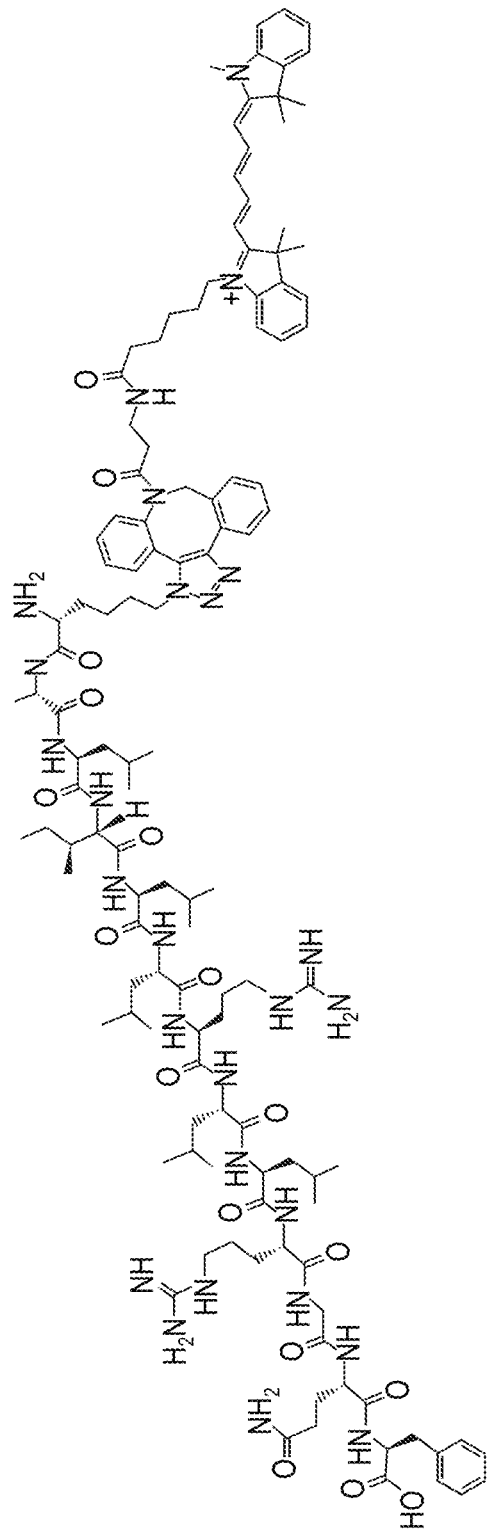
FIG. 24: Evaluation of cytosolic delivery of STP with polar cargo. Sequence of peptide is Cy5-DBCO-Lys(N3)-pliylrllrGqf (SEQ ID NO:11). Cells were treated at 1 µM concentration for 30 minutes. After incubation the cells were washed once with neuronal medium and 2× with HBSS. One final wash was given with the suggested dilution of NucBlue Live Readyprobe (Life Technologies) in order to visualize the cell nuclei.
Figure 24:
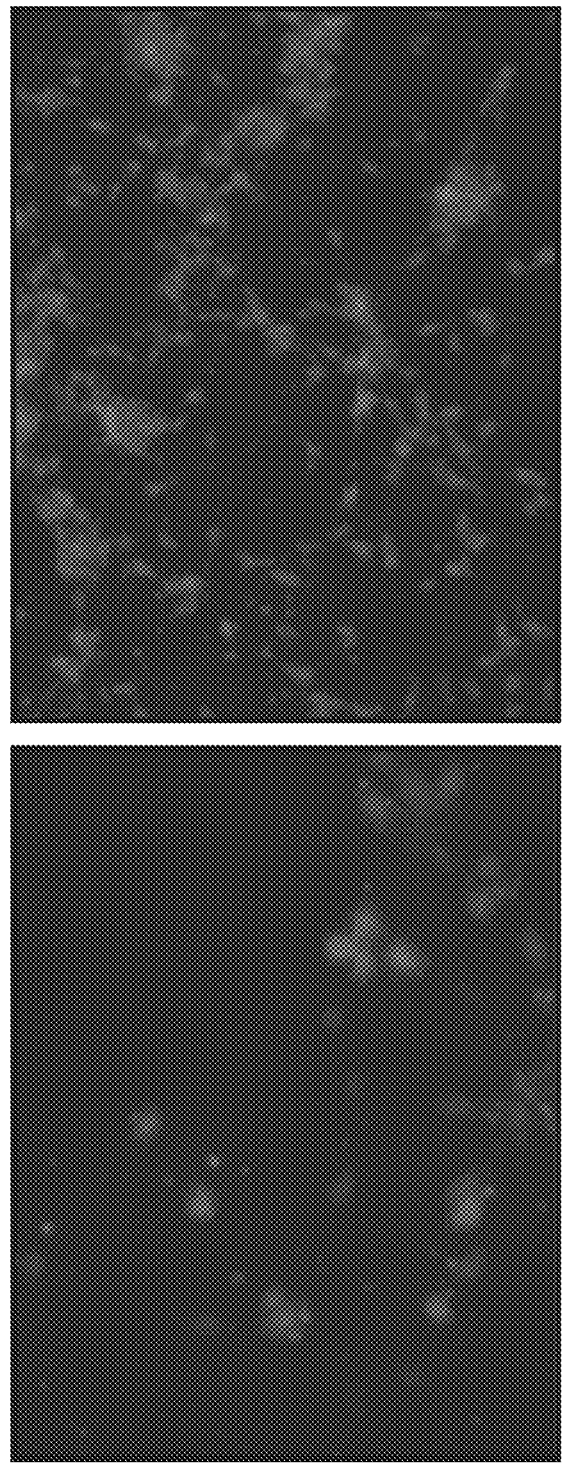

After extended maturation following plating, iCell neurons demonstrate functional synaptic vesicle recycling indicating the development of a presynaptic compartment. Synaptic vesicle recycling was monitored through FM1-43 vesicle staining followed by $Ca^{2+}/K^+$ dependent depolarization (FIGS. 22A-22D). The synaptic vesicles of BoNT intoxicated neurons can be stained, however $Ca^{2+}/K^+$ depolarization does not induce vesicle exocytosis and subsequent turn-off of FM1-43 fluorescence. Synaptic vesicles appearing as puncta in epifluorescent images of the live neurons were quantified on a per cell basis (FIG. 23) after exposure to BoNT pre-incubated with 1 μM of inhibitory ligands. Representative cells following depolarization are shown in FIG. 4B along with the synaptic vesicle counts for each condition quantified over three wells. As observed in the western blot assay, this functional assay shows negligible protection to BoNT intoxication by Inh-1, while Inh-2 provides full protection. These results are consistent with a Trojan horse-like inhibition mechanism in which the non-inhibiting L2 moiety of Inh-2 binds to the BoNT holotoxin, so that Inh-2 is shuttled into the cell by the holotoxin itself during the endocytosis step of BoNT intoxication. Once the belt is released, the Inh-1 moiety clamps down onto the active site, thus inhibiting the protein. To evaluate the effect of passive delivery to the cytosol, ligands were appended with an STP (FIG. 24). The Inh-1-STP compound targeting the active site showed increased protection compared to the membrane impermeable Inh-1, though not the complete protection expected at this concentration for the BoNT LC in vitro.

Figure 3C:
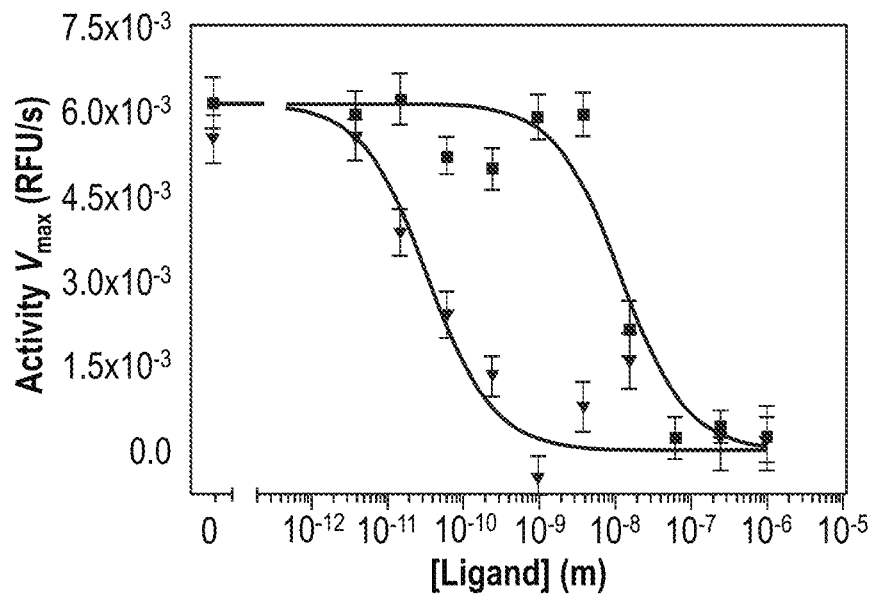
Figure 3D:
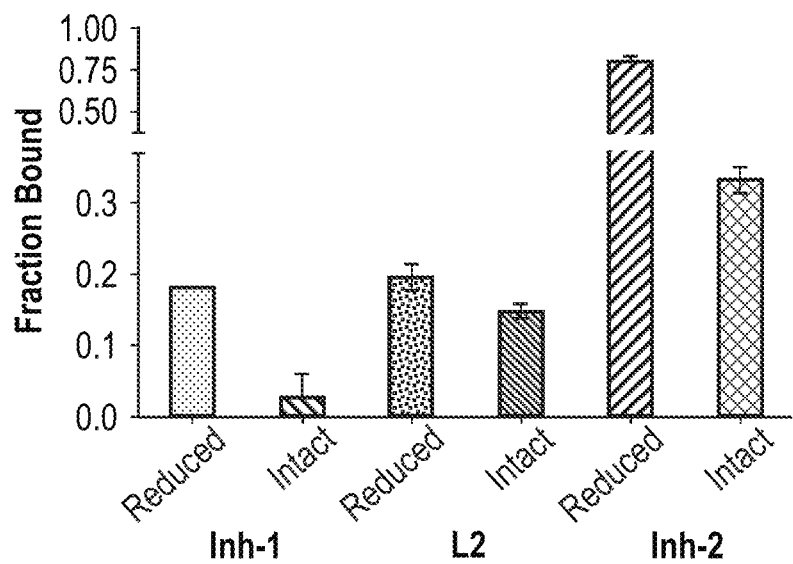
Figure 5A:
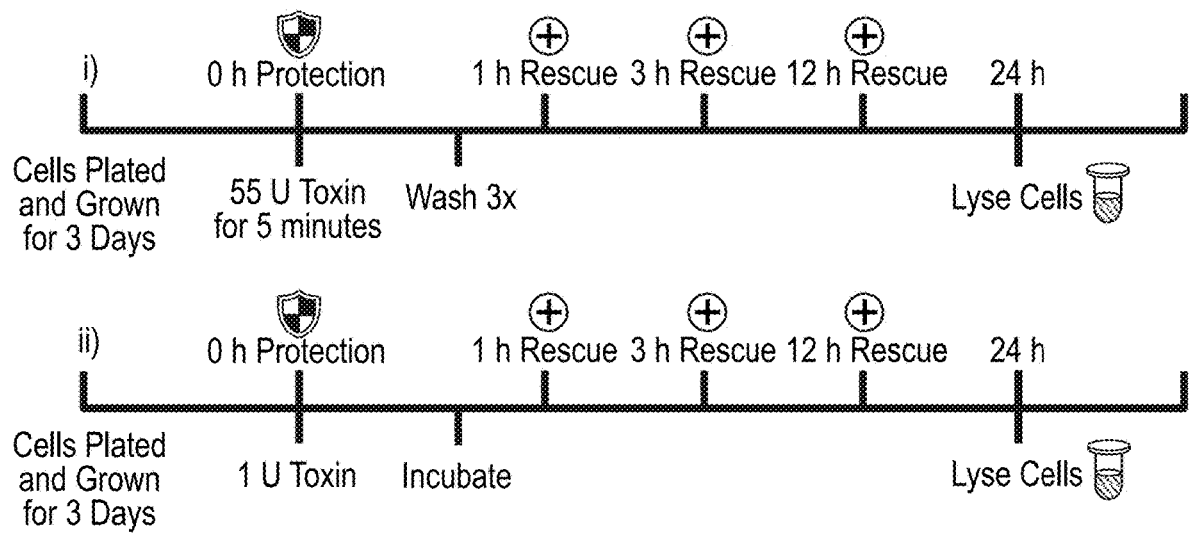
FIGS. 5A-5C: Rescuing hiPSC-derived neurons from BoNT intoxication.
Figure 5B:
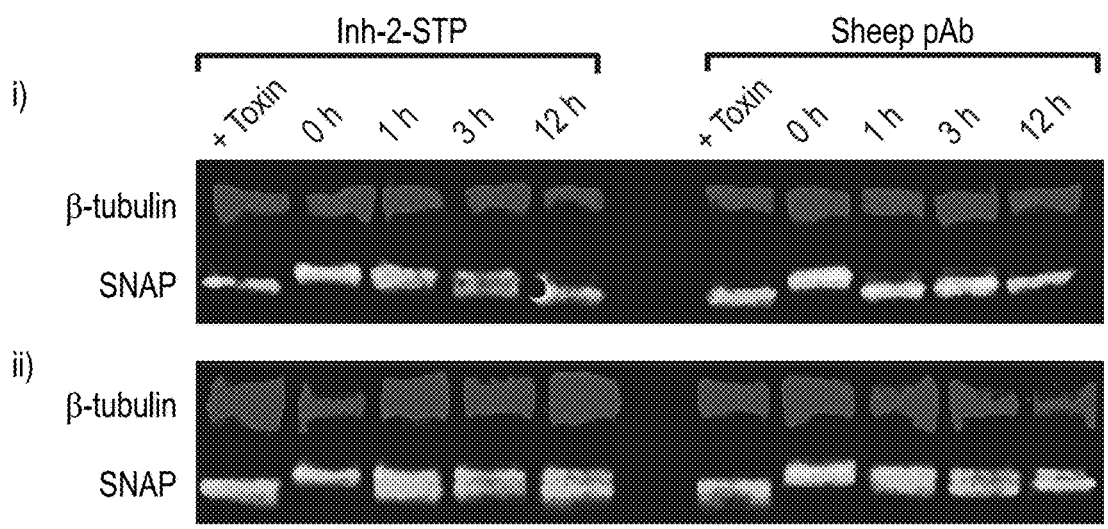
Figure 5C:
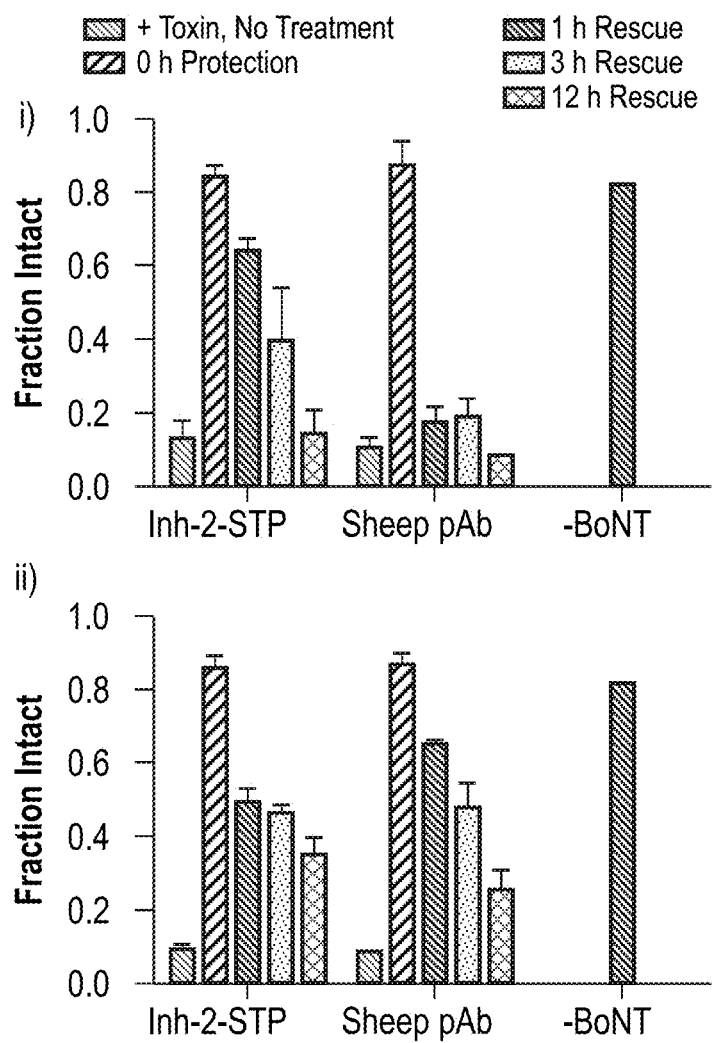

Both the membrane permeable and impermeable Inh-2 variants provided complete functional protection in neurons. Evaluated next was the BoNT-independent cellular entry of Inh-2-STP through rescue assays in which BoNT entry and intoxication begin before the addition of the inhibitor. Rescue was evaluated in iCell neurons in a bolus 55U five-minute exposure in cell-stimulating media followed by washing and an extended 1U exposure with no washing. In both experiments 1 μM inhibitory ligand was added to the cells 1, 3 and 12 hours post-exposure. All cells were lysed 24 hours after exposure and SNAP-25 cleavage was evaluated by western blotting (FIG. 5B). Two blots per condition were quantified and averaged by densitometry (FIG. 3C). In the bolus exposure, Inh-2-STP exhibits partial rescue from internalized BoNT as late as 3 hours after exposure, with later time points indicating the internalized BoNT had completely cleaved SNAP-25 after 12 hours. As expected, the sheep pAb shows no detectable rescue due to its mechanism of action, which is to prevent BoNT endocytosis. In the 1U extended exposure, both the sheep pAb and compound Inh-2-STP showed similar levels of rescue. The process of BoNT endocytosis is slowed significantly at low concentrations and in non-stimulating media, enabling protection through the pAb protective mechanism.

The rational use of the tertiary structure of a protein target was reported as a landscape for the assembly of a highly potent inhibitor. The specific application yielded a ligand, Inh-2 that succeeds as a strong inhibitor in spite of the naturally occluded active site of BoNT holotoxin. Inh-2 effectively acts as a Trojan horse; it is carried into the neuronal cells by the BoNT machinery. Once inside the cytosol, the BoNT LC active site is exposed and Inh-2 performs its inhibitory function. To our knowledge this divalent inhibitory ligand is the most potent in vitro and in cell inhibitor of BoNT/A yet reported and represents the first use of a peripheral binding site to enhance the binding avidity and facilitate BoNTiA holotoxin binding. This basic approach may have general applicability for developing high affinity and high specificity ligands that are designed to alter the function of inter-and intracellular targets.

Standard Materials

All amino acids were purchased from Aapptec as the Fmoc carboxylic acid with standard TFA side-chain protecting groups for solid phase peptide synthesis. HATU (2-(7-Aza-1H-benzotriazole-1-yl)-1,1,3,3-tetramethyluronium hexafluorophosphate) and $PEG_4$ (Fmoc-NH-PEG4-CH-2CH2COOH, Fmoc-18-amino-4,7,10,13,16-pentaoxaoctadecanoic acid) were purchased from Chem Pep. DIEA (diisoproylethylamine), triethylsilane (TES) and TFA (Trifluoroacetic acid) were purchased from Sigma Aldrich. TentaGel beads were purchased as 90 μm S—NH2 beads, 0.29 mmol/g, 2.86×106 beads/g from Rapp Polymere (Germany), Rink Amide resin was purchased from Anaspec and C-terminal biotinylated peptides were synthesized on Biotin NovaTag resin (EMD Millipore).

Cyclic Peptide Library Construction

Cyclic peptide libraries were synthesized on a Titan 357 split-and-mix automated peptide synthesizer (Aapptec) via standard FMOC SPPS coupling chemistry using 90 μm TentaGel S-$NH_2$ beads. All cyclic libraries included a C-terminal Lys(N3) residue, 18 L-stereoisomers of the natural amino acids, minus Cysteine and Methionine, at each of five randomized positions followed by a Propargylglycine residue. Libraries were cyclized overnight at RT after synthesis with 1.5 eq. CuI and 5 eq. L-ascorbic acid in 20% piperidine:NMP. Resin was chelated extensively with 5% w/v sodium diethyldithiocarbamate trihydrate and 5% v/v DIEA in NMP. For the in situ click screen, an azide or alkyne click handle was coupled to the N-terminus following cyclization. At least a five-fold excess of beads is used when synthesizing libraries to ensure oversampling of each sequence. Amino acid side-chains are protected by TFA labile protecting groups that are removed all at once following library synthesis using a 95:5:5 ratio of TFA:$H_2O$:TES.

Scaled Up Peptide Synthesis

Bulk synthesis of peptide sequences was performed using standard FMOC SPPS peptide chemistry on either the Titan 357 automated peptide synthesizer (AAPPTEC) or a Liberty 1 microwave peptide synthesizer (CEM Corporation). The typical scale was 300 mg on Rink Amide Resin, unless otherwise noted. Click cyclized peptides were cyclized overnight at RT after synthesis with 1.5 eq. CuI and 5 eq. L-ascorbic acid in 20% piperidine:NMP. Resin was chelated extensively with 5% w/v sodium diethyldithiocarbamate trihydrate and 5% v/v DIEA in NMP. Peptides were cleaved from the beads with deprotected side-chains using a 95:5:5 ratio of TFA:H2O:TES. The peptides were purified on a prep-scale Dionex U3000 HPLC with a reverse-phase C18 column (Phenomenex). All peptides are checked for correct mass and impurities using MALDI-TOF MS and are lyophilized to a powder for long-term storage at room temperature. Concentrated peptide stocks for assays are made by dissolving powder in small amounts of DMSO and measuring the A280 absorbance via Nanodrop to determine the stock concentration.

$3_{10}$ Helix Click-Stabilized Inhibitor Variant Synthesis

The peptidomimetic inhibitor Dab(Dinitrophenol)-RWT-Dab-ML (SEQ ID NO:8) as reported by Zuniga et al., (2011) was scaled up as outlined above with a C-terminal $PEG_4$ biotin and an N-terminal $PEG_4$ biotin. The N-terminally labeled variant showed no detectable binding in a point ELISA format or inhibition in an in vitro BoNT LC activity assay, this is consistent with the crystal structure indicating a partially buried N-terminus when bound. The C-terminally labeled variant was used as a control during the screening of various cyclic variants (FIG. 17). Sixteen variants were synthesized. All were based on the inhibitor above, with an (i, i+3) substitution of propargylglycine and azidolysine. Both possible arrangements of these residues were tested for each substitution as well as an up to two residue glycine extension on the C-terminus. All compounds were cyclized as detailed above.

Sandwich ELISA Assays for Initial Evaluation of BoNT LC Binding

These assays were conducted to test the binding of the various ligands to the BoNT LC protein. For this assay, all samples were taken in triplicate for statistical purposes. The target protein used was BoNT LC—GST conjugate (List Labs). Peptide ligands were first immobilized onto Neutravidin ELISA plates (Pierce) for one hour at 1 μM concentration. A $PEG_4$-biotin, was used as the no-ligand blank, as the GST proteins has significant background binding to a blank Neutravidin plate. The plates were then blocked with 5% BSA overnight. Protein was incubated at a concentration of 100 nM for samples wells and the blank wells. GST protein alone (Abcam) was also incubated with the ligands and blanks as a control. The proteins were incubated for three hours at room temperature, then washed three times with 1×TBS+0.05% Tween-20. The protein was then detected with 1:10,000 anti-GST mouse mAb (Fisher) for one hour, washed three times with 1×TBS+0.05% Tween-20 and developed with a 1:1 mixture of TMB substrate for ten minutes. The samples were plotted by subtracting the blanks and averaging the sample wells, when included error bars indicate one standard deviation above and below.

FRET-Based In Vitro BoNT-LC Activity Assay

FRET-based BoNT-LC activity assays were carried out as suggested by the manufacturer of the FRET pair labeled BoNT substrate (List Labs, SNAPtide #523). All time-resolved fluorescence assays were performed in a Flexstation 3 fluorescent plate reader at 37 degrees. Briefly, 8 μM of FRET-labeled substrate was prepared in Assay Buffer (50 mM HEPES, pH 7.4, containing 0.3 mM ZnCl2, 1.25 mM DTT and 0.05% Tween-20) in a black fluorescence 96-well plate. BoNT LC-GST conjugate was diluted to the indicated concentration (generally 1 nM unless noted otherwise) and preincubated either with the indicated concentration of inhibitory peptide ligand, or a 0.05% DMSO control. At time=0, the plate reader adds the BoNT-LC to the substrate, and begins monitoring the fluorescence. The excitation wavelength was set to 490 nm, and the emission to 523 nm with a cutoff at 495 nm. Wells were monitored for approximately one hour. Initial velocities of cleavage were plotted against inhibitor concentration.

Fluorescence Polarization Assays

Inh-1 and L2 were synthesized with fluorescein for fluorescence polarization (FP) assays. The BoNT LC binding assays were completed by making a 1 μM starting protein concentration and diluting 3× in Assay Buffer down a series of 10 wells in a black 96 well polystyrene plate. Ligand was added to the wells for a final concentration of 20 nM. The plate was incubated at room temperature for one hour with shaking, and read on a Flexstation 3 plate reader.

The data were fitted by subtracting the average of the low concentration baseline to zero in order to use the Hill fit. Using Graph Pad Prism, the curves were fitted to a Hill function using a common saturation point.

Secondary Binder Epitope-Targeted Screen

Screens were performed using a library with the form Pra-Pra-XXXXX-Lys(N3)-TG (SEQ ID NO:6), with the azido and propargyl amino acids closest to the bead clicked together to form a closed cycle. The peptide library was a comprehensive 5-mer containing 18 L-amino acids, excluding Met and Cys due to stability reasons. The N-terminus contained an alkyne amino acid for in situ click with the Lys(N3) on the target 13-mer-epitope fragment. Screens were performed using 400 mg of dried library beads swelled at least six hours in 1× TBS (25 mM Tris-Cl, 150 mM NaCl, 10 mM MgCl2, pH=7.5) buffer and blocked in Blocking Buffer (1×TBS+1% BSA+0.05% Tween-20) overnight. Screening against the BoNT LC 166-179 epitope was carried out in two main steps: a scrambled epitope pre-clear and a target epitope product screen.

Step 1: Scrambled Epitope Preclear

Swelled library beads were blocked overnight in blocking buffer then washed with 1×TBS three times. The scrambled epitope (Lys(N3)-NGTLFNLSEVRH-PEG$_4$-Biotin) (SEQ ID NO:10), FIG. 15) was added at a concentration of 5 μM in Blocking Buffer and incubated shaking at room temperature for four hours. The beads were washed three times with Blocking Buffer. 1:10 000 Mouse mAb anti-Biotin alkaline phosphatase conjugate (Abcam) was added in Blocking Buffer for one hour, followed by three washes in Blocking Buffer, three washes 1× TBS+0.05% Tween-20, and three 15 minute washes with a high-salt TBS buffer (1× TBS with 750 mM NaCl), then let shake in high salt buffer for one hour. The beads were then washed three times with BCIP buffer (100 mM Tris-Cl, 150 mM NaCl, 1 mM MgCl2, pH=9.0) and developed by adding 15 mL BCIP buffer plus 13 pL BCIP and 26 pL NBT (two part system, Promega). Development proceeded for 30 minutes. After development the beads were quenched with concentrated HCl to 0.1N and washed with MilliQ water ten times to remove substrate. Beads were placed in a plate in 0.05N HCl. The purple beads (typically approximately 1-5%) were removed by micropipette and discarded. The remaining beads were incubated in NMP 4 hours to remove trace purple precipitate from the BCIP/NBT reaction, then were washed five times with methanol, five times with water, five times with 1× TBS and reblocked overnight in Blocking Buffer.

Step 2: Target Epitope Product Screen

Beads remaining from the preclear were washed three times with Blocking Buffer, then incubated with 5 μM of the target epitope (Lys(N3)-SFGHEVLNLTRN (SEQ ID NO:9), FIG. 14) in Blocking Buffer for 12 hours to allow for an in situ click reaction to occur. The beads were then washed three times with 1× TBS and incubated for 1 hr with a 7.5M Guanadine-HCl buffer (pH=2.0) to remove all target epitope not attached covalently to the beads. These beads were then washed ten times with 1× TBS, reblocked overnight in Blocking Buffer, then incubated for one hour with a 1:10 000 Mouse mAb anti-Biotin alkaline phosphatase conjugate (Abcam) in Blocking buffer for 1 hr to detect for the presence of the biotinylated target epitope clicked to the hit beads. Antibody incubation was followed by three washes in Blocking Buffer, three washes 1× TBS+0.05% Tween-20, and three 15 minute washes with a high-salt TBS buffer (1× TBS with 750 mM NaCl), then let shake in high salt buffer for one hour. Afterwards, the beads were again washed three times in BCIP buffer and developed as per the preclear. Purple beads are removed from the screen via pipette as hit beads. These hits were incubated in the guanidine-HCl buffer to remove attached streptavidin, washed ten times with water and sequenced via edman degradation on a Procise CLC system from Applied Biosystems. See Table SX for sequences from product screen.

Kinetic In Situ Click Target-Guided Synthesis of Divalent Inhibitor

This screen was performed using a library with the form Pra-XXXXX-Pra-NYRWL-Lys(N3)-TG (SEQ ID NO:7), with the azido and propargyl amino acids closest to the bead clicked together to form a closed cycle. The peptide library was comprehensive from length zero to length five containing only four possible residues (Glycine, D-Leucine, Aminoisobutyrate and D-Proline, see FIG. 2). The N-terminus contained an alkyne amino acid for in situ click with the Inh-1—Biotin—Lys(N3) anchor inhibitor (FIG. 17). Screens were performed using 50 mg of dried library beads swelled at least six hours in 1× TBS (25 mM Tris-Cl, 150 mM NaCl, 10 mM MgCl2, pH=7.5) buffer and blocked in Blocking Buffer (1× TBS+1% BSA+0.05% Tween-20) overnight. Screening was performed with the Inh-1—Biotin—Lys(N3) anchor inhibitor compound and the BoNT LC protein.

Step 1: Inh-1 Interaction Preclear

Swelled library beads were blocked overnight in blocking buffer then washed with 1× TBS three times. The anchor inhibitor (Inh-1—Biotin—Lys(N3)) FIG. 17) was added at a concentration of 10 μM in Blocking Buffer and incubated shaking at room temperature for four hours. The beads were washed three times with Blocking Buffer. 1:10 000 Mouse mAb anti-Biotin alkaline phosphatase conjugate (Abcam) was added in Blocking Buffer for one hour, followed by three washes in Blocking Buffer, three washes 1× TBS+0.05% Tween-20, and three 15 minute washes with a high-salt TBS buffer (1× TBS with 750 mM NaCl), then let shake in high salt buffer for one hour. The beads were then washed three times with BCIP buffer (100 mM Tris-Cl, 150 mM NaCl, 1 mM MgCl2, pH=9.0) and developed by adding 15 mL BCIP buffer plus 13 pL BCIP and 26 pL NBT (two part system, Promega). Development proceeded for 30 minutes. After development the beads were quenched with concentrated HCl to 0.1N and washed with MilliQ water ten times to remove substrate. Beads were placed in a plate in 0.05N HCl. The purple beads (approximately 1%) were removed by micropipette and discarded. The remaining beads were incubated in NMP 4 hours to remove trace purple precipitate from the BCIP/NBT reaction, then were washed five times with methanol, five times with water, five times with 1× TBS and reblocked overnight in Blocking Buffer.

Step 2: Target-Guided Synthesis Product Screen

Beads remaining from the preclear were washed three times with Blocking Buffer, then incubated with 10 μM of the anchor inhibitor (Inh-1—Biotin—Lys(N3)) FIGS. 17) and 100 nM BoNT LC in Blocking Buffer for either 2 or 12 hours to allow for an in situ click reaction to occur. The beads were then washed three times with 1× TBS and incubated for 1 hr with a 7.5M Guanadine-HCl buffer (pH=2.0) to remove all Inh-1 not attached covalently to the beads. These beads were then washed ten times with 1× TBS, reblocked overnight in Blocking Buffer, then incubated for one hour with a 1:10 000 Mouse mAb anti-Biotin alkaline phosphatase conjugate (Abcam) in Blocking buffer for 1 hr to detect for the presence of the biotinylated Inh-1 clicked to the hit beads. Antibody incubation was followed by three washes in Blocking Buffer, three washes 1× TBS+0.05% Tween-20, and three 15 minute washes with a high-salt TBS buffer (1× TBS with 750 mM NaCl), then let shake in high salt buffer for one hour. Afterwards, the beads were again washed three times in BCIP buffer and developed as per the preclear. Purple beads are removed from the screen via pipette as hit beads. These hits were incubated in the guanidine-HCl buffer to remove attached streptavidin, washed ten times with water and sequenced via edman degradation on a Procise CLC system from Applied Biosystems. See FIG. 16 for sequences from product screen.

iCell Neuron Culture

The cryopreserved hiPSC-derived neurons (iCell Neurons) were supplied by Cellular Dynamics International. The neurons were an ~98% pure (Tuj1+/Nestin-) pan-neuronal population of GABAergic, glutamatergic, and a very small percentage (<1%) of dopaminergic neurons. Neurons were thawed according to the provided instructions, and live cells were counted by the Trypan Blue exclusion method. Cells were seeded at a density of 50,000 cells per well into Poly-D-Lysine Coated 96 Well plates (Corning) and 8.3 µg/cm$^2$ human Laminin (Sigma) unless otherwise indicated and incubated in neuronal medium with supplement as provided by Cellular Dynamics International. 50% of the medium was replaced every 3 days. Neural outgrowth staining (Life Technologies) showed substantial neurite growth and maturation 3 days after plating (Figure S16). Active synaptic vesicle recycling upon $K^+/Ca^{2+}$ depolarization was monitored by FM1-43 (Life Technologies) staining and nearly all neurons showed repeatable staining and destaining by day 15 after plating (FIG. 22A-D).

Neuronal BoNT Toxicity Assays

For all neuronal toxicity assays, 3 day post plating hiPSC-derived neurons were exposed to the indicated concentrations of BoNT/A holotoxin (List Labs) with indicated inhibiting compounds in 50 µL of neuronal medium allowed to pre-incubate for 1 hr at 37 degrees. A negative control without toxin was always included. After 24 hours of exposure time, the toxin solution was removed and cells were lysed in 50 µl of 1× lithium dodecyl sulfate (LDS) loading buffer (Invitrogen). The cell lysates were analyzed by western blot for SNAP-25 cleavage and beta-tubulin as a loading control. SNAP-25 was probed using Ms anti-SNAP-25 SMI-81 (Abcam) as a primary and goat anti-Ms H&L Alexafluor 790 (Life Technologies) as a secondary and imaged using an Odyssey instrument at the 800 nm wavelength. Beta Tubulin was probed using Rb anti-beta Tubulin (Life Technologies) as a primary and goat anti-Rb H&L Alexafluor 680 (Life Technologies) as a secondary and imaged using an Odyssey instrument at the 700 nm wavelength. Cleaved SNAP-25 bands appeared below the intact SNAP-25 band, and each were quantified by densitometry in ImageJ and the relative fraction of intact SNAP-25 indicated in FIGS. 4A-4B and 5A-3C.

For protection assays, neurons were cultured and exposed to toxin as indicated above. At the indicated times, 10 µL of neuronal medium spiked with inhibitory compounds were added at an appropriate concentration to bring the total concentration in the well to 1 µM in a total volume of 60 µL. As above, 24 hours post exposure all cells were lysed with 1× LDS and analyzed by western blot.

Synaptic Vesicle Recycling Assays hiPSC-derived neurons were cultured as indicated above and allowed to mature, with 50% replacement of neuronal medium every three days. After 15 days, the neurons showed synaptic vesicle staining and destaining using FM1-43 dye followed by $K^+/Ca^{2+}$ depolarization. These matured neuron cultures were exposed to the indicated BoNT/A holotoxin pre-incubated with inhibitor as indicated, and were then assayed with FM1-43.

For FM1-43 loading, control and toxin/inhibitor-exposed neurons were washed in Hank's Balanced Salt Solution (HBSS) and depolarized for 5 min at 37 degrees with 56 mM KCl in isosmotic HBSS containing 2 mM CaCl2 and 2 mM FM1-43 (Life Technologies). Cultures were washed twice for 10 minutes in HBSS without $Ca^{2+}$ and containing 0.5 mM EGTA, to wash surface membranes of the dye while preventing neuronal activation and loss of FM1-43 from within already labeled terminals. Labeled neurons were imaged in this rinse solution; some wells underwent a second round of depolarization (in the absence of FM1-43) to destain synaptic terminals and evaluate functional intoxication. Before imaging, all conditions were given a last wash with the suggested dilution of NucRed Live 647 live cell nuclear stain (Life Technologies). FM1-43 labeled cultures were photographed using an EVOS FL microscope. FM1-43 could be monitored on the RFP/GFP channels and the NucRed stained was monitored on the Cy5 channel.

Images were analyzed by ImageB. We used a watershed analysis to find the edges of neuron cell bodies in the transmission channel and allocate a given intercellular area to each cell. These areas were then mapped onto the FM1-43 layer and puncta were counted in each area using the PunctaAnalyzer package while ignoring the previously identified cell bodies to find only synaptic vesicle puncta along neurites. The puncta count for each cell was averaged over two wells with two fields of view per well. A typical analysis is shown in FIG. 23.

Cell Penetration of STP-DBCO-Cy5

The spontaneously translocated peptide (pliylrllrGqf) previously reported was synthesized from D-stereoisomer amino acids with an N-terminal Lys(N3). DBCO-Cy5 was then coupled to the azide with 1.1 eq. using strain-promoted click chemistry in DMF overnight. To verify that this peptide could delivery a sizeable polar cargo to the neuronal cytosol, STP-DBCO-Cy5 was diluted to 1 µM concentration in neuronal media and added to the neurons for 30 minutes. After incubation the cells were washed once with neuronal medium and 2× with HBSS. One final wash was given with the suggested dilution of NucBlue Live Readyprobe (Life Technologies) in order to visualize the cell nuclei. Neurons were imaged live with an EVOS FL microscope system. NucBlue could be monitored on the DAPI channel, STP-DBCO-Cy5 could be monitored on the Cy5 channel. A representative view of cell showing Cy5 in the cytosol is shown in FIG. 24.

Synthesis of Inh-2 and Inh-2-STP Peptide Bicycles

Compound Inh-2 was synthesized on Rink Amide resin beginning with the synthesis of the L-2 cyclic peptide NH2-Pra-NYRWL-Lys(N3) (SEQ ID NO:5) on resin. This peptide was cyclized and chelated as detailed previously. The linker region was then coupled resulting in the compound NH$_2$-G-Aib-L-[Pra-NYRWL-Lys(N3)] (SEQ ID NO:5) where square brackets indicate a closed cycle. The custom "T$_z$4" residue Fmoc-Lys(N3-Boc-Pra-OH)-Otbu was then coupled on resin. After Fmoc deprotection, either Fmoc-Lys(Mtt)-OH or Fmoc-Lys(Biotin)-OH (both Chempep) were then coupled depending on whether an orthogonally addressable amine or a biotin handle is needed (for Inh-2 and Inh-2-STP respectively). After Fmoc deprotection, the Inh-1 peptide is coupled as detailed previously resulting in the compound NH$_2$-Dab(DNP)-R-Lys(N3)-T-Dab(Boc)-Pra-L-Lys (MTT or Biotin)-T$_z$4-G-Aib-L-[Pra-NYRWL-Lys(N3)] ((SEQ ID NO:3)-T$_z$4-G-Aib-L- (SEQ ID NO:5)) where square brackets indicate a closed cycle. This compound is then cyclized and chelated again as detailed above to create the bicyclic compound. For Inh-2-STP synthesis, the MTT protecting group is removed from the Lys(MTT) by 10 washes with 1% TFA in DCM. The protection group removal was monitored by the yellow color of the eluent. DBCO-acid (Sigma) was coupled to the free amine, and STP (see synthesis above) was coupled with 1.1 eq. using strain-promoted click chemistry in DMF overnight. This peptide is cleaved as normal with 95:5:5 TFA:H2O:TES and purified by reverse phase HPLC. The structure and MALDI-TOF spectrum of these compounds can be found in FIGS. 10, 18 and 20.

What is claimed is:

1. A method of synthesizing a capture agent to a target comprising the steps of:
   (a) selecting a linker to connect an anchor ligand to a secondary ligand, wherein the anchor ligand and the secondary ligand were previously determined to bind to the same target at different binding sites representing distinct epitopes, wherein the linker is selected based on the distance between the binding site of the anchor ligand and the binding site of the secondary ligand, wherein the anchor ligand and the secondary ligand bind their respective binding sites on the target in an orientation such that the target can promote 1,3-dipolar cycloaddition between an acetylene group on one of the anchor ligand or secondary ligand and an azide group on the other of the anchor ligand or secondary ligand to form a triazole linkage in the absence of a separate catalyst, wherein for the cycloaddition reaction one of the azide group or the acetylene group is connected to the anchor ligand or secondary ligand via the selected linker; and
   (b) synthesizing a capture agent comprising the anchor ligand, the secondary ligand, and the selected linker, thereby generating the capture agent, wherein the dissociation constant of the capture agent for binding to the target is lower than the dissociation constant of either the anchor ligand or the secondary ligand for binding to the target.

2. The method of claim 1, wherein the linker has a length that is within 10% of the distance between the anchor ligand and the secondary ligand when both ligands are bound to the target.

3. A method of synthesizing a capture agent for inhibiting SNAP-25 cleavage mediated by botulinum neurotoxin serotype A protein in one or more neurons, wherein the botulinum neurotoxin serotype A protein comprises a heavy chain and a light chain, wherein the light chain comprises an enzymatic active site, comprising
   (a) selecting an anchor ligand that specifically binds to the enzymatic active site of the botulinum neurotoxin serotype A protein;
   (b) selecting a secondary ligand that specifically binds at a distinct epitope from the anchor ligand within 5-10 angstroms on the botulinum neurotoxin serotype A protein; and
   (c) linking the anchor ligand and secondary ligand together,
   wherein the secondary ligand must bind to an epitope so that it specifically binds to an occluded conformation of the botulinum neurotoxin serotype A holotoxin, thereby synthesizing the capture agent for inhibiting SNAP-25 cleavage mediated by botulinum neurotoxin serotype A protein in one or more neurons.

4. The method of claim 3, wherein the linking of the anchor ligand and the secondary ligand is performed using a linker.

5. The method of claim 4, wherein the linker has a length that is between 100 and 110% of the distance between the anchor ligand and the secondary ligand when both ligands are bound to the botulinum neurotoxin serotype A protein.

6. A method of targeting adjacent epitopes on a single protein comprising
   (a) identifying an anchor ligand that binds to a first epitope and a secondary ligand that binds to a second epitope, wherein the first and second epitopes are adjacent on the single protein;
   (b) screening the anchor ligand and secondary ligand against a linker library based on affinity of the combined anchor ligand, linker and secondary ligand to bind the single protein; and
   (c) selecting a linker to connect the anchor ligand to the secondary ligand, thereby targeting adjacent epitopes of the single protein by generating a capture agent that targets adjacent epitopes on the single protein, wherein the dissociation constant of the capture agent for binding to the target protein is lower than the dissociation constant of either the anchor ligand or the secondary ligand for binding to the target protein.

7. The method of claim 6, wherein the adjacent epitopes are 5-10 angstroms apart on the single protein when the single protein is folded.

8. The method of claim 4, wherein the linker has a length that is between 100 and 110% of the distance between the anchor ligand and the secondary ligand when both ligands are bound to the first and second epitopes, respectively.

9. The method of claim 4, wherein the linker is a tripeptide.

10. The method of claim 4, wherein the anchor ligand, secondary ligand, or both, are linked to the linker via a 1,4-substituted-1,2,3-triazole residue (Tz4) or via a 1,5-substituted-1,2,3-triazole residue (Tz5).

11. The method of claim 1 further comprising, prior to selecting the linker, the steps of:
    (i) identifying an anchor ligand and a secondary ligand that bind to the same target peptide at distinct epitopes;
    (ii) identifying the binding sites of the anchor ligand and the secondary ligand on the target peptide; and
    (iii) calculating the distance between the binding site of the anchor ligand and the secondary ligand.

12. The method of claim 1, wherein the target is a protein.

13. The method of claim 1, wherein the anchor ligand is identified by binding to an epitope on the target.

14. The method of claim 1, wherein the secondary ligand is identified by binding to an epitope on the target.

15. The method of claim 1 further comprising, prior to selecting the linker, identifying the anchor ligand, the secondary ligand, and the binding sites of the anchor ligand and the secondary ligand on the target.

16. The method of claim 1 further comprising, prior to selecting the linker, calculating the distance between the binding site of the anchor ligand and the binding site of the secondary ligand.

17. The method of claim 1, wherein the capture agent further comprises a tertiary ligand.

* * * * *